(12) United States Patent
Cooks et al.

(10) Patent No.: US 10,204,772 B2
(45) Date of Patent: *Feb. 12, 2019

(54) MASS SPECTROMETRY ANALYSIS OF MICROORGANISMS IN SAMPLES

(71) Applicant: Purdue Research Foundation, West Lafayette, IN (US)

(72) Inventors: Robert Graham Cooks, West Lafayette, IN (US); Ahmed Mohamed Hamid, Cairo (EG); Alan Keith Jarmusch, Lafayette, IN (US); Zheng Ouyang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/902,068

(22) Filed: Feb. 22, 2018

(65) Prior Publication Data

US 2018/0204712 A1 Jul. 19, 2018

Related U.S. Application Data

(63) Continuation of application No. 15/483,132, filed on Apr. 10, 2017, now Pat. No. 9,941,105, which is a
(Continued)

(51) Int. Cl.
| | |
|---|---|
| *H01J 49/04* | (2006.01) |
| *G01N 27/62* | (2006.01) |
| *C12N 13/00* | (2006.01) |
| *C12Q 1/04* | (2006.01) |
| *H01J 49/16* | (2006.01) |

(52) U.S. Cl.
CPC .......... *H01J 49/0445* (2013.01); *C12N 13/00* (2013.01); *C12Q 1/04* (2013.01); *G01N 2560/00* (2013.01); *H01J 49/16* (2013.01)

(58) Field of Classification Search
CPC ........ H01J 49/04; H01J 49/16; H01J 49/0404; H01J 49/0027; H01J 49/0031; H01J 49/0431; H01J 49/14; H01J 49/168; H01J 49/0459; H01J 49/0036; H01J 49/0045; H01J 49/0436; H01J 49/10; H01J 49/165; H01J 49/26; H01J 49/0004; H01J 49/0022; H01J 49/0418; H01J 49/0472; H01J 49/061; H01J 49/142; H01J 49/167; H01J 49/24; H01J 49/40; H01J 49/4215; G01N 1/00; G01N 33/6848; G01N 21/6428; G01N 21/648; G01N 21/7703; G01N 27/4473; G01N 27/62; G01N 27/624; G01N 2800/20; G01N 30/02; G01N 30/20; G01N 30/603; G01N 30/6095; G01N 30/7266; G01N 30/78; A61B 5/097; A61B 5/411;
(Continued)

(56) References Cited

U.S. PATENT DOCUMENTS

| | | | | |
|---|---|---|---|---|
| 4,757,198 A | * | 7/1988 | Korte | ............. H01J 49/0022 250/282 |
| 5,583,281 A | * | 12/1996 | Yu | .................... G01N 30/20 73/23.42 |

(Continued)

*Primary Examiner* — David A Vanore
(74) *Attorney, Agent, or Firm* — Brown Rudnick LLP; Adam M. Schoen

(57) ABSTRACT

The invention generally relates to systems and methods for mass spectrometry analysis of microorganisms in samples.

20 Claims, 80 Drawing Sheets

Specification includes a Sequence Listing.

Related U.S. Application Data continuation of application No. 14/900,827, filed as application No. PCT/US2014/034767 on Apr. 21, 2014, now Pat. No. 9,620,344, which is a continuation of application No. 13/926,645, filed on Jun. 25, 2013, now Pat. No. 8,704,167.

(58) Field of Classification Search
CPC ... A61B 5/0045; A61B 5/0051; A61B 5/0064; A61B 5/02
USPC ... 250/281, 282, 288, 287, 423 R, 292, 286, 250/396 R, 424, 290, 284, 289, 341, 250/341.1, 341.2, 425; 436/172, 164, 436/173, 174, 518, 525, 86
See application file for complete search history.

(56) References Cited

U.S. PATENT DOCUMENTS

| | | | | |
|---|---|---|---|---|
| 6,297,499 B1* | 10/2001 | Fenn | ............ | H01J 49/167 250/288 |
| 6,627,881 B1* | 9/2003 | Bertrand | ............ | H01J 49/0472 250/288 |
| 6,992,284 B2* | 1/2006 | Schultz | ............ | H01J 49/0045 250/287 |
| 7,223,969 B2* | 5/2007 | Schultz | ............ | H01J 49/0045 250/281 |
| 7,384,793 B2* | 6/2008 | McCash | ............ | A61B 5/097 436/172 |
| 7,544,933 B2* | 6/2009 | Cooks | ............ | H01J 49/14 250/281 |
| 7,564,027 B2* | 7/2009 | Finch | ............ | G01N 1/2214 250/281 |
| 7,714,281 B2* | 5/2010 | Musselman | ............ | H01J 49/0404 250/281 |
| 7,930,924 B2* | 4/2011 | Krogh | ............ | G01N 1/4005 73/23.4 |
| 8,030,088 B2* | 10/2011 | McCash | ............ | A61B 5/097 436/164 |
| 8,076,639 B2* | 12/2011 | Cooks | ............ | H01J 49/14 250/281 |
| 8,421,005 B2* | 4/2013 | Musselman | ............ | H01J 49/0404 250/281 |
| 8,481,922 B2* | 7/2013 | Musselman | ............ | H01J 49/0404 250/281 |
| 8,704,167 B2* | 4/2014 | Cooks | ............ | C12Q 1/04 250/281 |
| 8,859,986 B2* | 10/2014 | Cooks | ............ | C12Q 1/04 250/281 |
| 8,937,288 B1* | 1/2015 | Cooks | ............ | C12Q 1/04 250/281 |
| 9,620,344 B2* | 4/2017 | Cooks | ............ | H01J 49/0445 |
| 9,733,228 B2* | 8/2017 | Cooks | ............ | G01N 33/2823 |
| 9,941,105 B2* | 4/2018 | Cooks | ............ | H01J 49/0445 |
| 2004/0245457 A1* | 12/2004 | Granger | ............ | H01J 49/0436 250/288 |
| 2007/0187589 A1* | 8/2007 | Cooks | ............ | H01J 49/14 250/288 |
| 2009/0309020 A1* | 12/2009 | Cooks | ............ | H01J 49/14 250/282 |
| 2010/0001181 A1* | 1/2010 | Moini | ............ | G01N 27/4473 250/282 |
| 2011/0108724 A1* | 5/2011 | Ewing | ............ | G01N 1/2214 250/282 |
| 2012/0119079 A1* | 5/2012 | Ouyang | ............ | H01J 49/0431 250/282 |
| 2013/0112866 A1* | 5/2013 | Ouyang | ............ | H01J 49/0431 250/282 |
| 2013/0112867 A1* | 5/2013 | Ouyang | ............ | H01J 49/0431 250/282 |
| 2013/0273560 A1* | 10/2013 | Cooks | ............ | G01N 27/62 435/7.1 |
| 2013/0299694 A1* | 11/2013 | Sato | ............ | A61B 10/0045 250/288 |
| 2014/0008532 A1* | 1/2014 | Ouyang | ............ | H01J 49/0431 250/287 |
| 2014/0048697 A1* | 2/2014 | Cooks | ............ | C12Q 1/04 250/281 |
| 2015/0017712 A1* | 1/2015 | Cooks | ............ | C12Q 1/04 435/287.1 |
| 2016/0254131 A1* | 9/2016 | Cooks | ............ | C12N 13/00 435/287.1 |

* cited by examiner

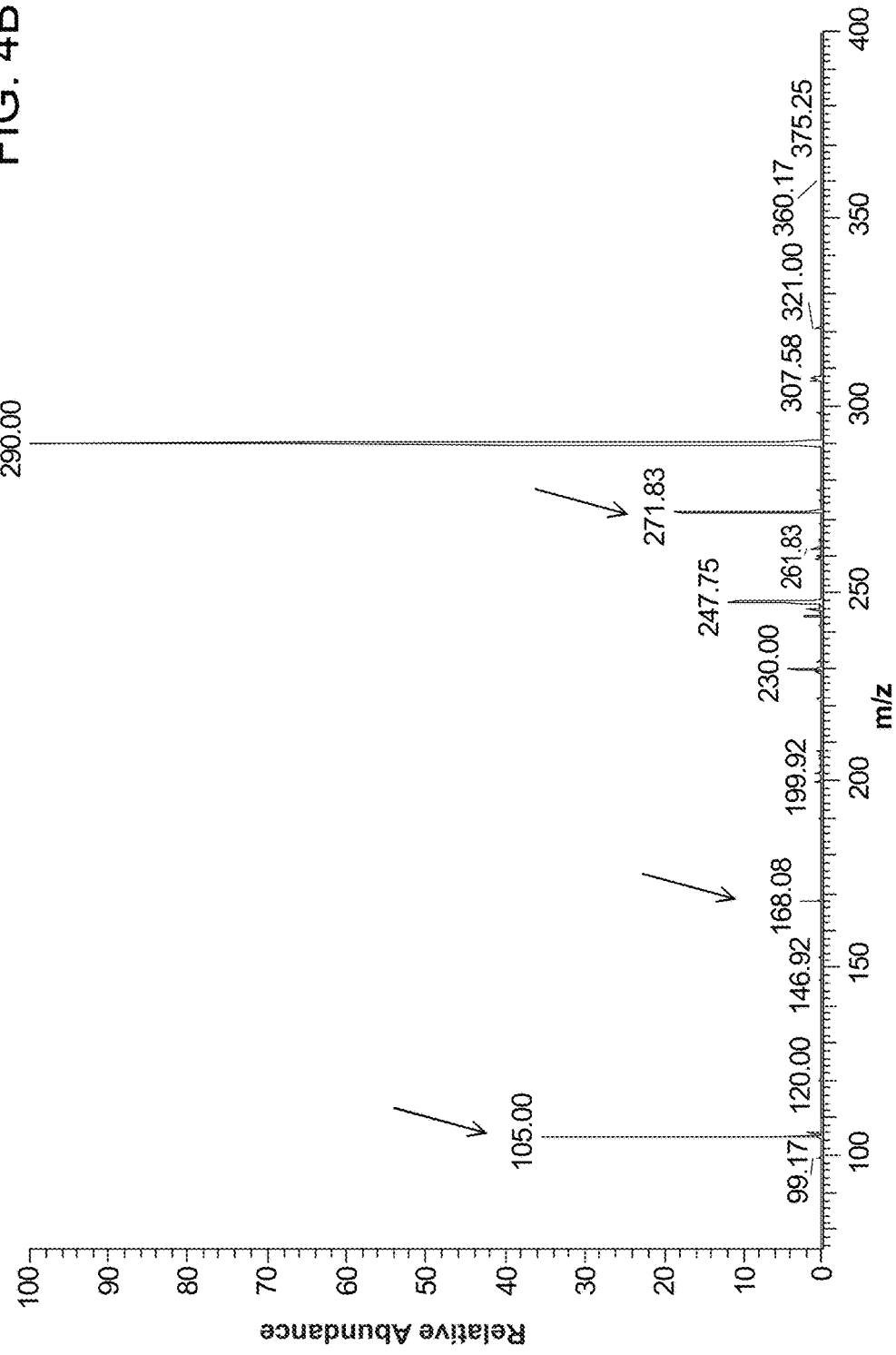

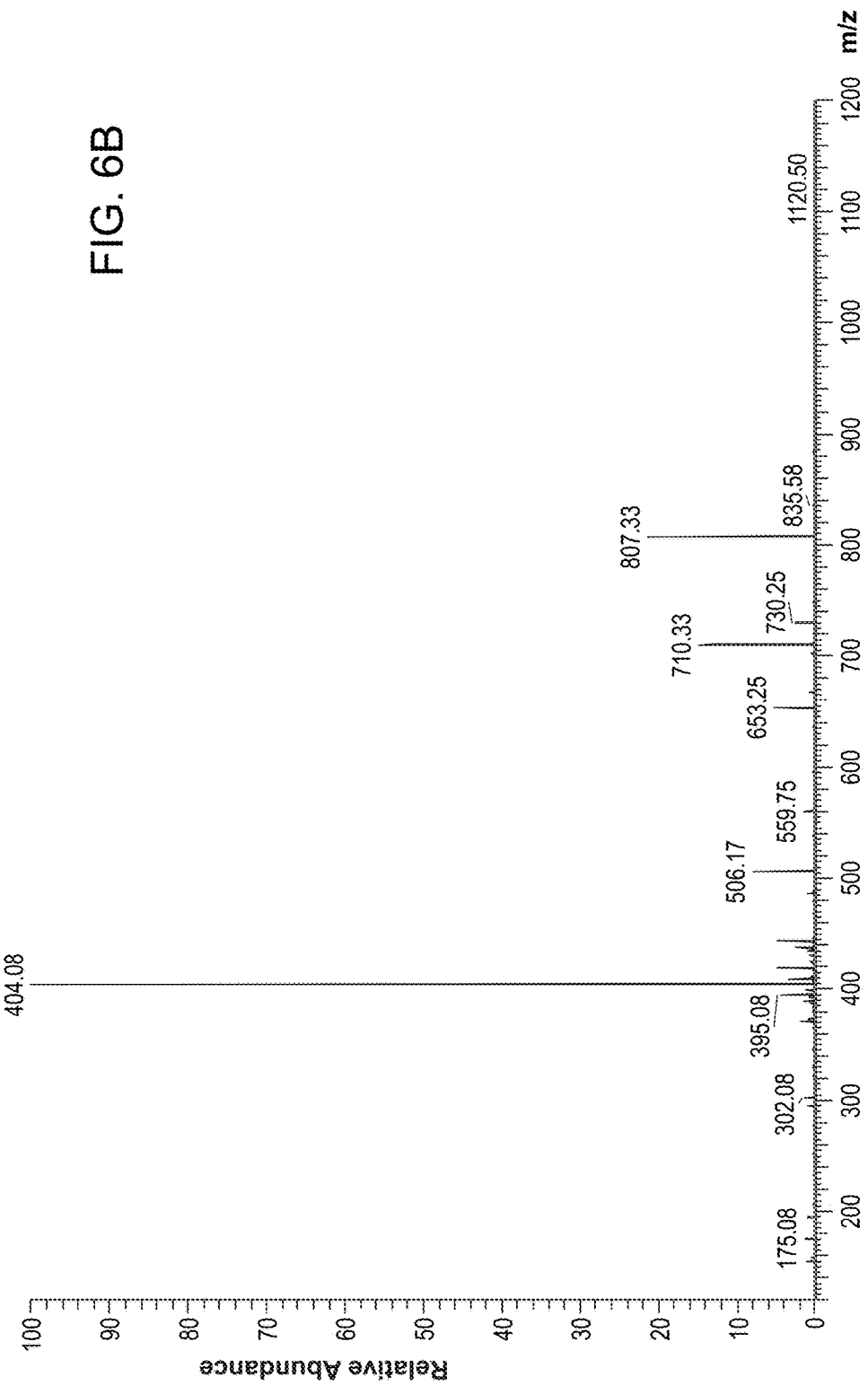

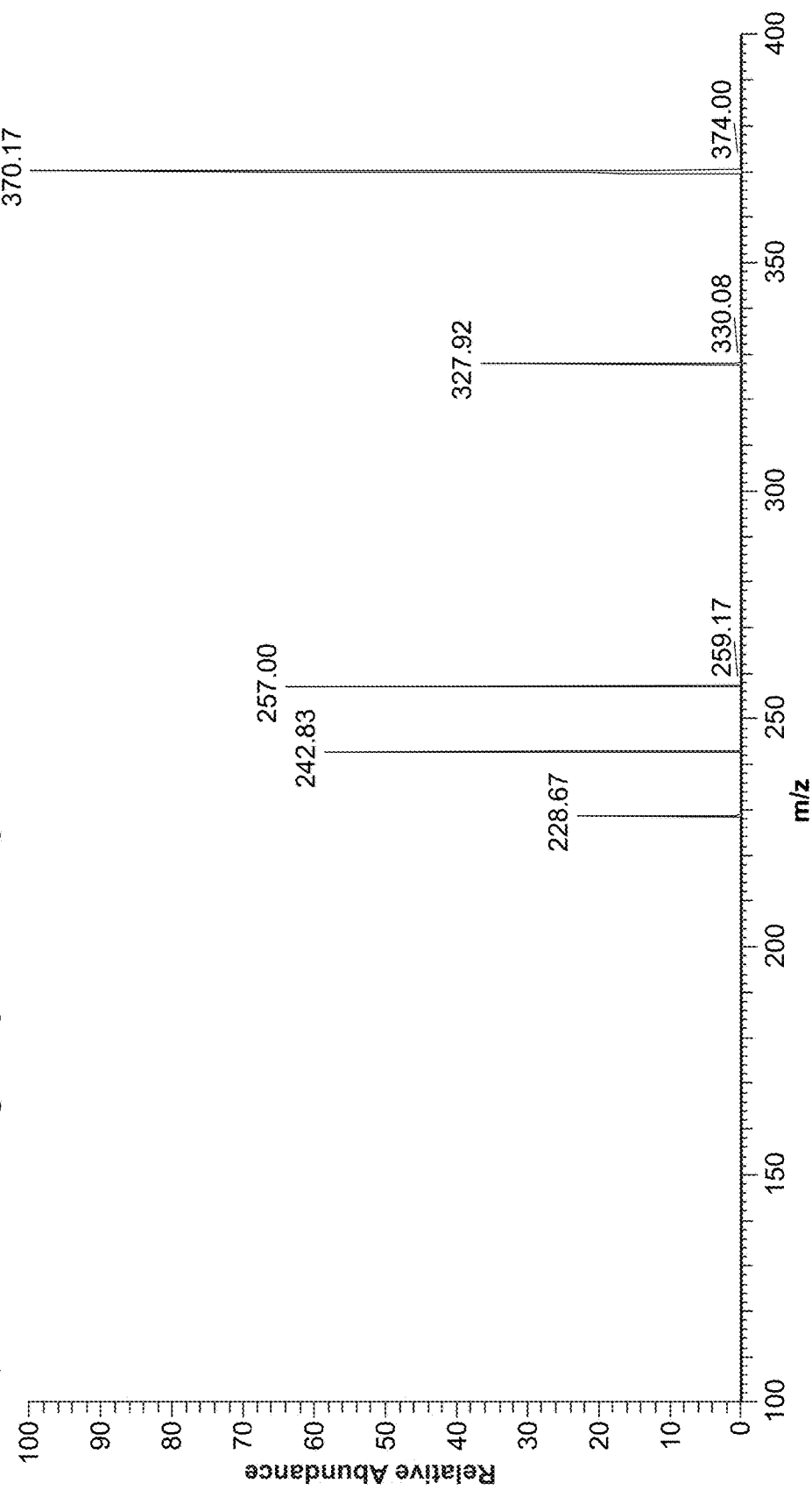

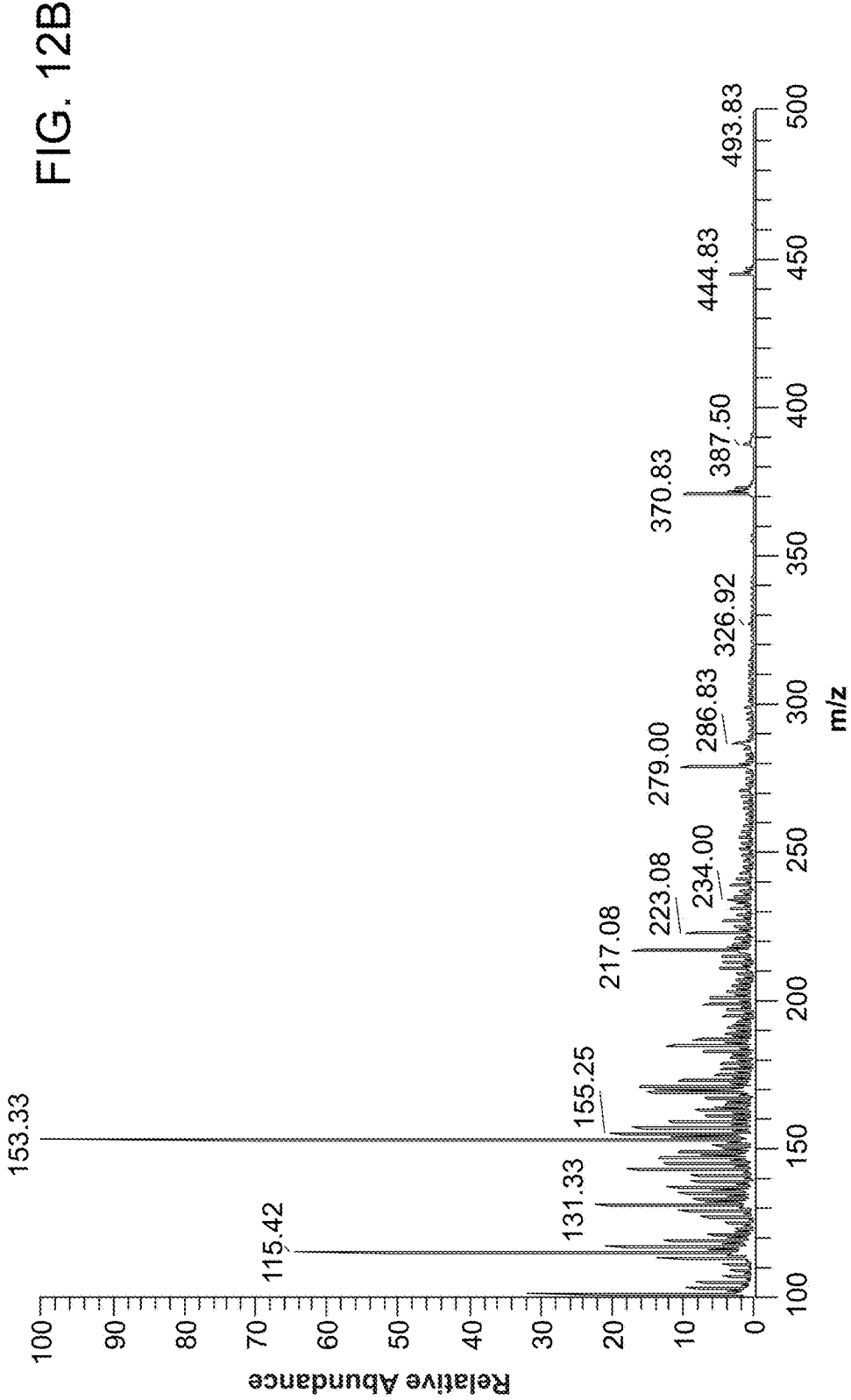

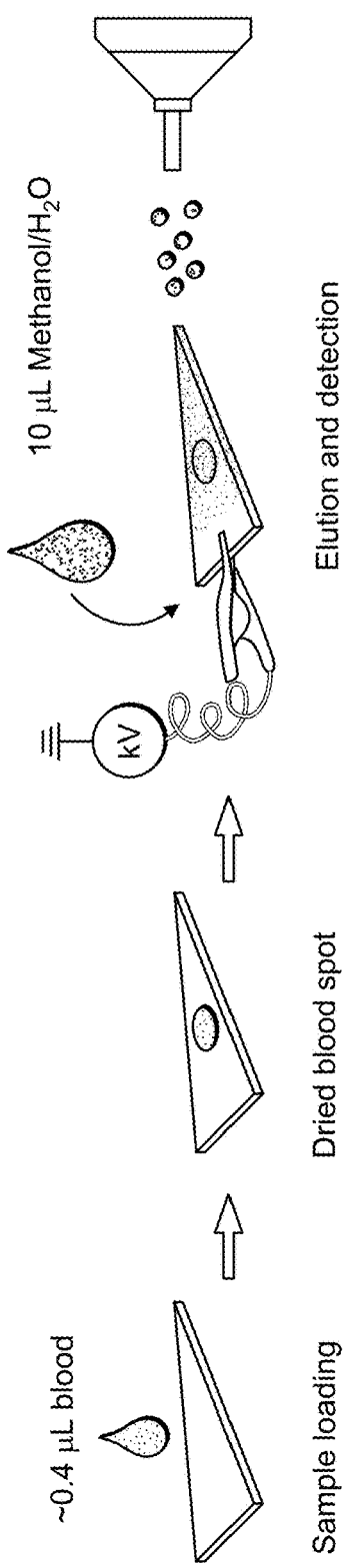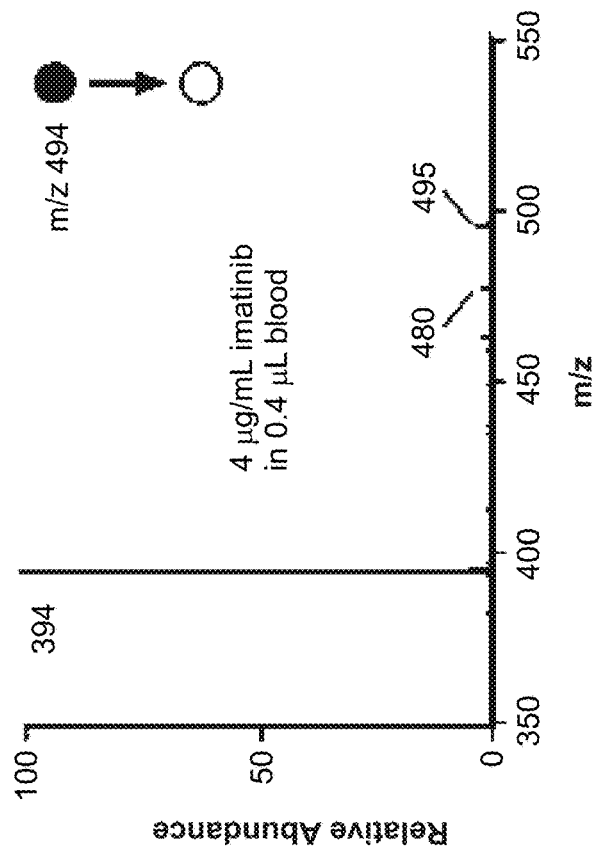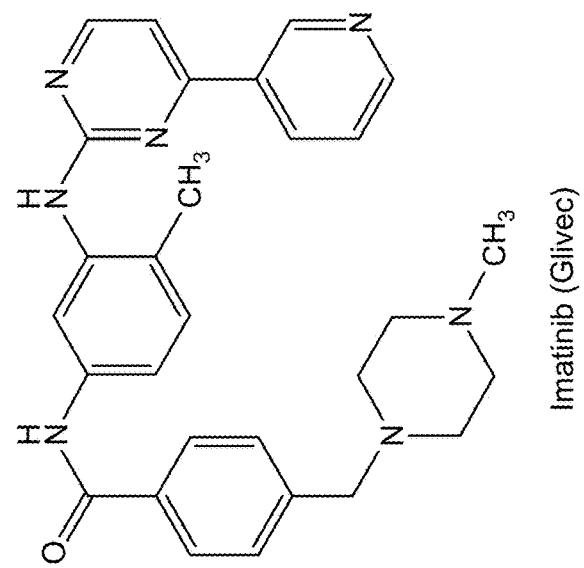
FIG. 14A
FIG. 14B

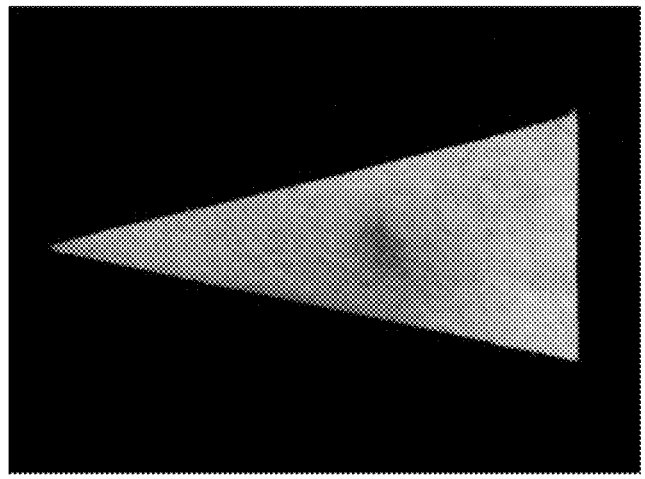
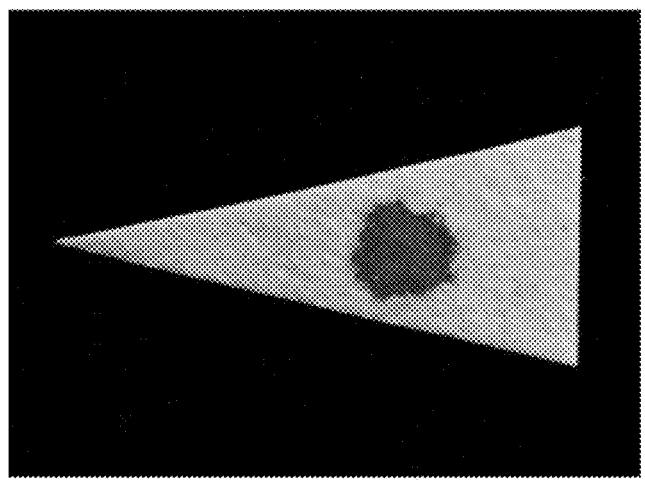
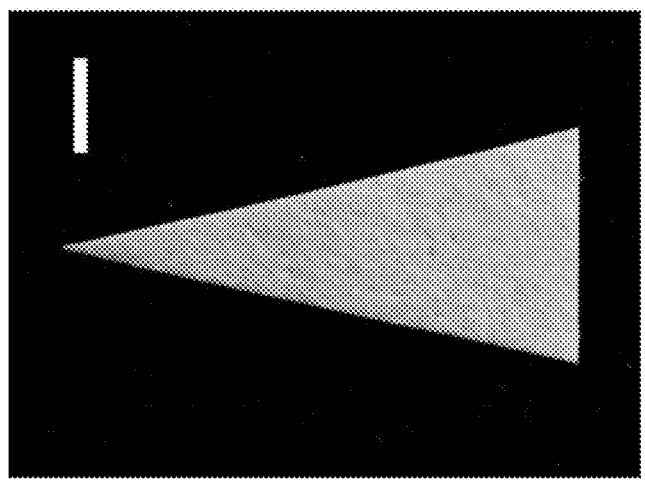
FIG. 23A

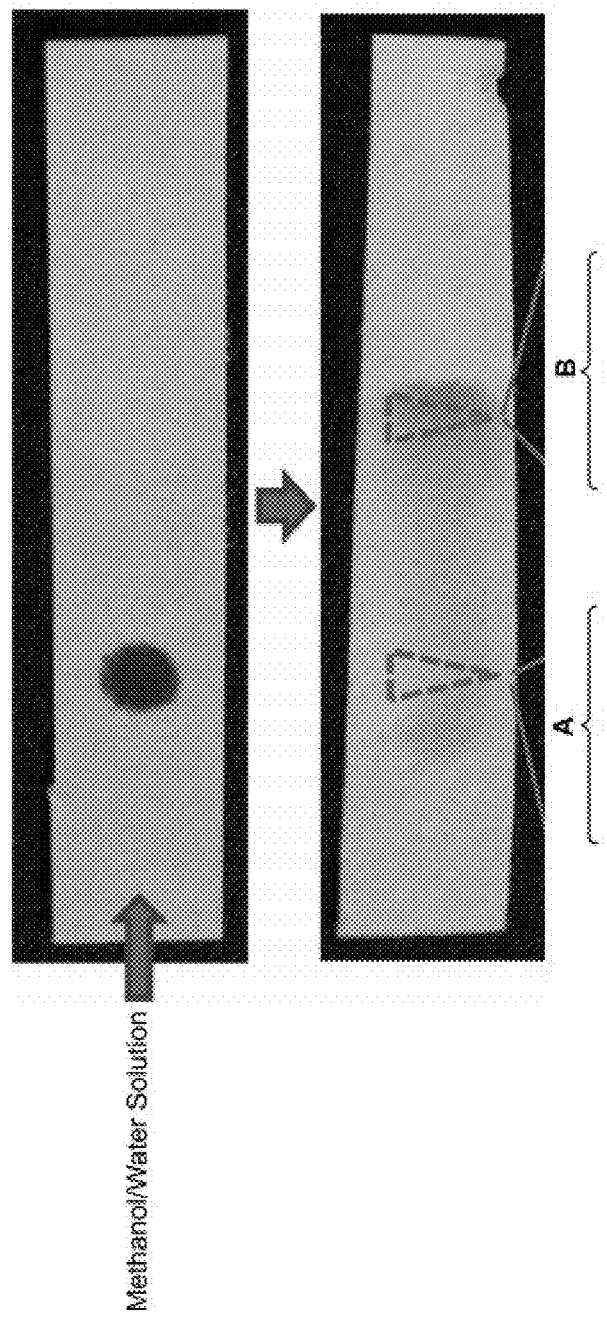

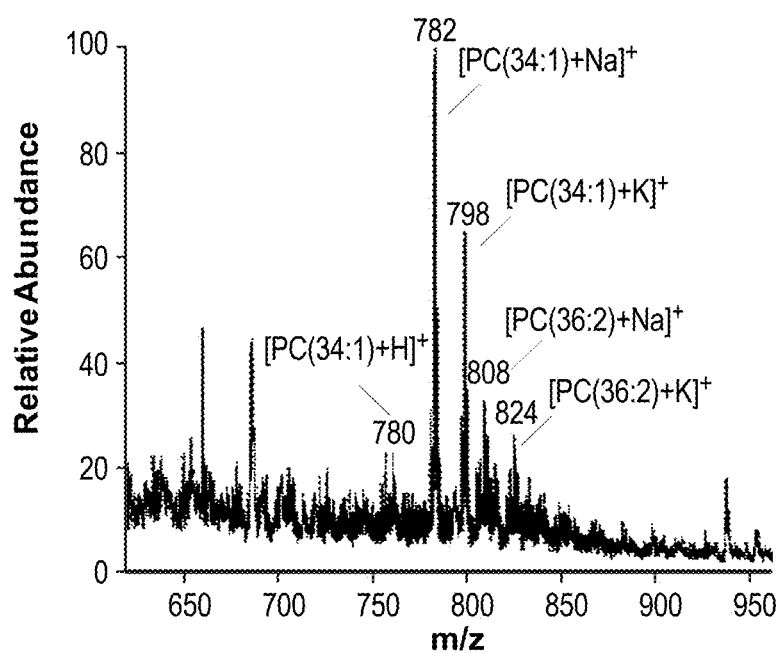
FIG. 29C    Lipids on tumor section
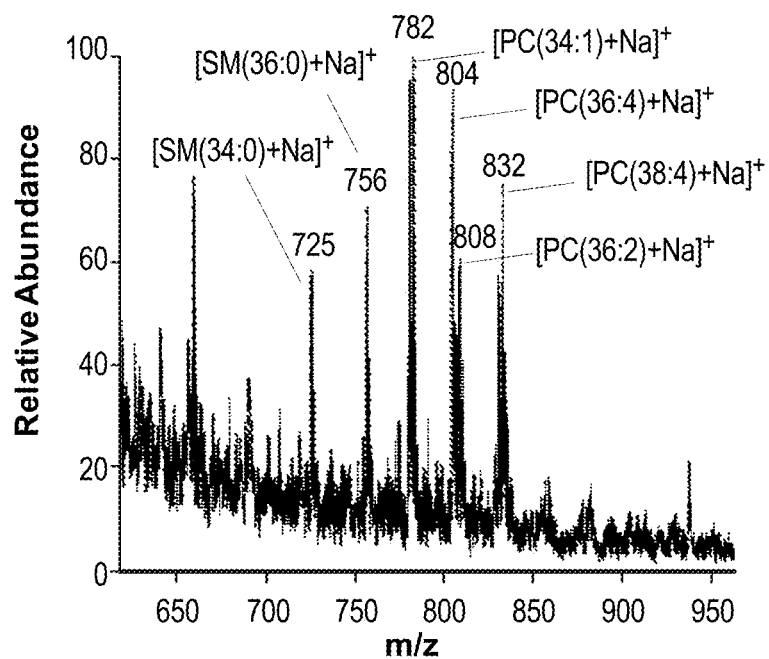
FIG. 29D    Lipids on non-tumor section Collection of Aerosols Air Flow →

Consumable Sample Cartridge With Paper Substrate

Paper Spray MS Analisis

Spray Solvent

DC 4 kV

MS Inlet

FIG. 37

MASS SPECTROMETRY ANALYSIS OF MICROORGANISMS IN SAMPLES

RELATED APPLICATIONS

The present application is a continuation of U.S. nonprovisional application Ser. No. 15/483,132, filed Apr. 10, 2017, which is a continuation of U.S. nonprovisional application Ser. No. 14/900,827, filed Dec. 22, 2015, which is a 35 U.S.C. § 371 national phase application of PCT/US14/34767, filed Apr. 21, 2014, which claims the benefit of and priority to U.S. nonprovisional application Ser. No. 13/926,645, filed Jun. 25, 2013, the content of each of which is incorporated by reference herein in its entirety.

TECHNICAL FIELD

The invention generally relates to systems and methods for mass spectrometry analysis of microorganisms in samples.

BACKGROUND

Mass spectrometry is a very sensitive analytical method used for important research and for applications of analytical chemistry, particularly life science. Electrospray ionization (ESI) is generally regarded as the best-characterized and most efficient method for ionization of molecules in solution phase. The process can be conveniently divided into three stages: droplet formation, droplet evaporation and ion formation (Gaskell, S. J. *Journal of Mass Spectrometry* 1997, 32, 677-688). When a strong electric field is applied to a solution flowing through a mass spectrometer probe, a Taylor cone is formed at the tip of the probe, resulting in a mist of small droplets being emitted from the tip of this cone. Due to the evaporation of the free droplets and Coulombic forces, ions of sample analyte are produced. The ions enter a mass spectrometer and are subsequently analyzed.

A problem with ESI is that sample preparation is still a necessary step before ESI can be used for analysis of many types of samples. Prior to analyzing a sample by ESI mass spectrometry, the sample will undergo extraction and filtration protocols to purify the sample, for example to remove salts and detergents. Such protocols are complex, time-consuming, and expensive. Further, reagents used during the purification process can interfere with subsequent analysis of a target analyte in the purified sample. Additionally, samples that are not in solution must be dissolved as well as purified prior to ESI analysis.

More recently, the concept of ambient ionization has been developed, and now this family of ambient ionization has more than twenty members, such as desorption electrospray ionization (DESI) and direct analysis in real time (DART). Ambient ionization by mass spectrometry allows the ionization of analytes under an ambient environment from condensed-phase samples without much or even any sample preparation and/or pre-separation, offering a solution for real time and in situ analysis for complex mixtures and biological samples. These ambient ionization methods are leading are extending the mass spectrometry revolution in life science, environment monitoring, forensic applications and therapeutic analysis. However, the above described ambient ionization techniques still require pneumatic assistance, a continuous flow of solvent, and a high voltage power supply for the analysis of samples.

There is an unmet need for systems and methods that can combine sample preparation and pre-treatment and the ionization process for mass analysis of samples that do not require pneumatic assistance or a continuous flow of solvent for the analysis of the samples.

SUMMARY

The invention generally relates to new systems and methods of generating ions from fluids and solid samples for mass spectrometric analysis. Porous materials, such as filter paper or similar materials are used to hold and transfer liquids, and ions are generated directly from the edges of the materials when a high electric voltage is applied to the materials. The porous material is kept discrete (i.e., separate or disconnected from) from a flow of solvent. Instead, a sample is either spotted onto the porous material or the porous material is wetted and used to swab a surface containing the sample. The porous material with spotted or swabbed sample is then wetted and connected to a high voltage source to produce ions of the sample which are subsequently analyzed. The sample is transported through the porous material without the need of a separate solvent flow.

Devices and methods of the invention combine sample preparation and pre-treatment with the ionization process needed for mass analysis of samples. Device and methods of the invention allow for rapid and direct analysis of chemicals in raw biological samples of complex matrices, such as biofluids and tissues, without sample preparation. In particular embodiments, devices and methods of the invention allow for the analysis of a dried spots of blood or urine.

An aspect of the invention provides a mass spectrometry probe including a porous material connected to a high voltage source, in which the porous material is discrete from a flow of solvent. Exemplary porous materials include paper, e.g., filter paper, or PVDF membrane. The porous material can be of any shape. In certain embodiments, the porous material is provided as a triangular piece.

In certain embodiments, the probe further includes a discrete amount of a solvent, e.g., a droplet or droplets, applied to the porous material. The solvent is applied as a droplet or droplets, and in an amount sufficient to wet the porous material. Once applied to the porous material, the solvent can assist transport of the sample through the porous material. The solvent can contain an internal standard. The solvent/substrate combination can allow for differential retention of sample components with different chemical properties. In certain embodiments, the solvent minimizes salt and matrix effects. In other embodiments, the solvent includes chemical reagents that allow for on-line chemical derivatization of selected analytes.

Another aspect of the invention provides a system for analyzing a sample material including, a probe including a porous material connected to a high voltage source, in which the porous material is kept separate from a flow of solvent, and a mass analyzer. The mass analyzer can be that of a benchtop mass spectrometer or a handheld mass spectrometer. Exemplary mass analyzers include a quadrupole ion trap, a rectilinear ion trap, a cylindrical ion trap, a ion cyclotron resonance trap, and an orbitrap.

Another aspect of the invention includes a method for analyzing a sample including, contacting a sample to a porous material, in which the porous material is kept separate from a flow of solvent, applying a high voltage to the porous material to generate ions of an analyte in the sample that are expelled from the porous material, and analyzing the expelled ions. The method can further include applying a discrete amount, e.g., a droplet or droplets, of a solvent to the porous material. In certain embodiments, analyzing involves providing a mass analyzer to generate a mass spectrum of analytes in the sample.

In certain embodiments, the sample is a liquid. In other embodiments, the sample is a solid. In embodiments in which the sample is a solid, the porous material can be used to swab the sample from a surface. A solvent can be applied to the porous material prior to or after the solid has been swabbed. Exemplary samples include chemical species or biological species.

Another aspect of the invention provides a method of ionizing a sample including applying a high voltage to a porous material to generate ions of an analyte in the sample, in which the porous material remains separate from a solvent flow. Exemplary porous materials include paper or PVDF membrane.

BRIEF DESCRIPTION OF THE FIGURES

FIG. 4B is a MS/MS spectrum of benzoylecgonine (concentration: 10 ppb, volume: 10 µl, solvent: MeOH/$H_2O$/HOAc (50:49:1, v/v/v)).

FIG. 6B is a MS/MS spectrum of bradykinin2-9 (concentration: 1 ppm, volume: 10 µl, solvent: MeOH/$H_2O$/HOAc (50:49:1, v/v/v)).

FIG. 7B shows the MS/MS spectrum of the blood spot without heroin.

FIG. 10A is a MS spectrum showing that caffeine was detected in urine from a person who consumed coffee. FIG. 10B is a MS spectrum showing that caffeine was not detected in urine from a person who had not consumed any coffee.

FIGS. 12A-D show direct MS spectra of plant tissues using sliced tissues of four kinds of plants. (FIG. 12A) Onion, (FIG. 12B) Spring onion, and two different leaves (FIG. 12C) and (FIG. 12D).

FIG. 13A direct analysis of onion without sample preparation. FIG. 13B using standard solution.

FIG. 14A is a picture showing dried blood spot analysis on paper; 0.4 µL of whole blood is applied directly to a triangular section of chromatography paper (typically height 10 mm, base 5 mm). A copper clip holds the paper section in front of the inlet of an LTQ mass spectrometer (Thermo Fisher Scientific, San Jose, Calif.) and a DC voltage (4.5 kV) is applied to the paper wetted with 10 µL methanol/water (1:1 v/v). FIG. 14B shows the molecular structure of imatinib (GLEEVEC) and paper spray tandem mass spectrum of 0.4 µL whole blood containing 4 µg/mL imatinib. Imatinib is identified and quantified (inset) by the MS/MS transition m/z 494→m/z 394 (inset).

(FIG. 19A) 3 µm, (FIG. 19B) 4-7 µm, (FIG. 19C) 8 µm, and (FIG. 19D) 11 µm, (FIG. 19E) glass fiber paper and (FIG. 19F) chromatography paper). The spray voltage was 4.5 kV.

FIGS. 22A-B are mass spectra of COCA-COLA (cola drink), which was directly analyzed on paper in both of (FIG. 22A) positive and (FIG. 22B) negative mode. FIG. 22C is a mass spectrum of caffeine. FIG. 22D is a mass spectrum of potassium benzoate. FIG. 22E is a mass spectrum of acesulfame potassium. FIG. 22F is a mass spectrum of caffeine detected from urine. FIG. 22G is a mass spectrum of heroin detected directly from a desktop surface after swabbing of the surface by probes of then invention.

FIG. 23A shows images of a probe of the invention used for blood analysis. In this embodiment, the porous material is paper. The panel on the left is prior to spotting with whole blood. The panel in the middle is after spotting with whole blood and allowing the spot to dry. The panel on the right is after methanol was added to the paper and allowed to travel through the paper. The panel on the right shows that the methanol interacts with the blood spot, causing analytes to travel to the tip of the paper for ionization and analysis.

FIGS. 24A-C show analysis of two dyes, methylene blue (m/z 284) and methyl violet (m/z 358.5), separated by TLC. Dye mixture solution (0.1 µl of a 1 mg/mL solution) was applied onto the chromatography paper (4 cm×0.5 cm) and dried before TLC and paper spray MS analysis.

FIG. 25A shows sharpness. FIG. 25B shows angle of the tip. FIG. 25C shows thickness of the paper. FIG. 25D shows a device with multiple spray tips. FIG. 25E shows a DBS card with micro spray tips fabricated with sharp needles.

FIG. 26A shows a MS spectrum for 5 µg/mL. FIG. 26B shows a MS/MS spectrum for 5 ng/mL.

FIGS. 29B-D are mass spectra showing different chemicals detected in the tissue.

FIG. 37 shows an exemplary method of collecting microorganisms onto probes of the invention when the sample is a gas/aerosol.

FIG. 39A is negative ion mode and FIG. 39B is positive ion mode.

DETAILED DESCRIPTION

Figure 1A:
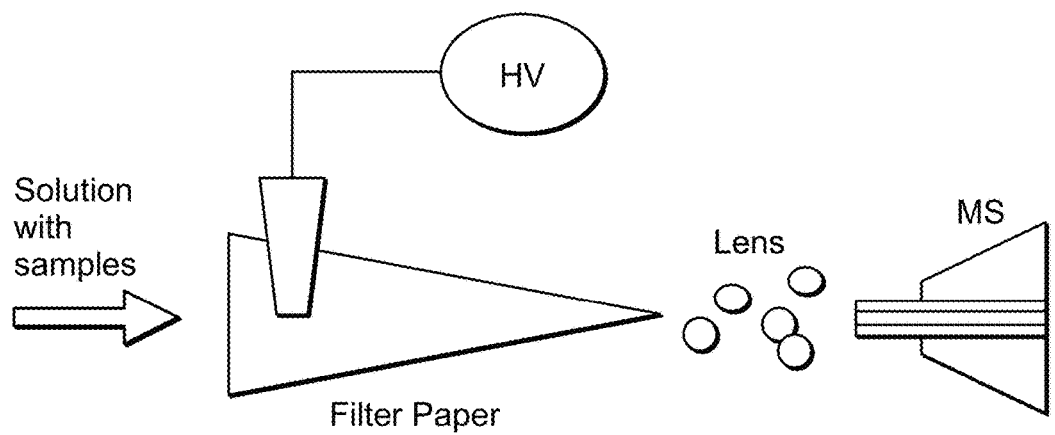
FIG. 1A is a drawing of a sample solution being fed to a piece of paper for electrospray ionization.

A new method of generating ions from fluids and solids for mass spectrometry analysis is described. Porous materials, such as paper (e.g. filter paper or chromatographic paper) or other similar materials are used to hold and transfer liquids and solids, and ions are generated directly from the edges of the material when a high electric voltage is applied to the material (FIG. 1). The porous material is kept discrete (i.e., separate or disconnected) from a flow of solvent, such as a continuous flow of solvent. Instead, sample is either spotted onto the porous material or swabbed onto it from a surface including the sample. The spotted or swabbed sample is then connected to a high voltage source to produce ions of the sample which are subsequently mass analyzed. The sample is transported through the porous material without the need of a separate solvent flow. Pneumatic assistance is not required to transport the analyte; rather, a voltage is simply applied to the porous material that is held in front of a mass spectrometer.

In certain embodiments, the porous material is any cellulose-based material. In other embodiments, the porous material is a non-metallic porous material, such as cotton, linen wool, synthetic textiles, or plant tissue. In still other embodiments, the porous material is paper. Advantages of paper include: cost (paper is inexpensive); it is fully commercialized and its physical and chemical properties can be adjusted; it can filter particulates (cells and dusts) from liquid samples; it is easily shaped (e.g., easy to cut, tear, or fold); liquids flow in it under capillary action (e.g., without external pumping and/or a power supply); and it is disposable.

In certain embodiments, the porous material is integrated with a solid tip having a macroscopic angle that is optimized for spray. In these embodiments, the porous material is used for filtration, pre-concentration, and wicking of the solvent containing the analytes for spray at the solid type.

In particular embodiments, the porous material is filter paper. Exemplary filter papers include cellulose filter paper, ashless filter paper, nitrocellulose paper, glass microfiber filter paper, and polyethylene paper. Filter paper having any pore size may be used. Exemplary pore sizes include Grade 1 (11 μm), Grade 2 (8 μm), Grade 595 (4-7 μm), and Grade 6 (3 μm), Pore size will not only influence the transport of liquid inside the spray materials, but could also affect the formation of the Taylor cone at the tip. The optimum pore size will generate a stable Taylor cone and reduce liquid evaporation. The pore size of the filter paper is also an important parameter in filtration, i.e., the paper acts as an online pretreatment device. Commercially available ultra filtration membranes of regenerated cellulose, with pore sizes in the low nm range, are designed to retain particles as small as 1000 Da. Ultra filtration membranes can be commercially obtained with molecular weight cutoffs ranging from 1000 Da to 100,000 Da.

Probes of the invention work well for the generation of micron scale droplets simply based on using the high electric field generated at an edge of the porous material. In particular embodiments, the porous material is shaped to have a macroscopically sharp point, such as a point of a triangle, for ion generation. Probes of the invention may have different tip widths. In certain embodiments, the probe tip width is at least about 5 μm or wider, at least about 10 μm or wider, at least about 50 μm or wider, at least about 150 μm or wider, at least about 250 μm or wider, at least about 350 μm or wider, at least about 400μ or wider, at least about 450 μm or wider, etc. In particular embodiments, the tip width is at least 350 μm or wider. In other embodiments, the probe tip width is about 400 μm. In other embodiments, probes of the invention have a three dimensional shape, such as a conical shape.

As mentioned above, no pneumatic assistance is required to transport the droplets. Ambient ionization of analytes is realized on the basis of these charged droplets, offering a simple and convenient approach for mass analysis of solution-phase samples.

Sample solution is directly applied on the porous material held in front of an inlet of a mass spectrometer without any pretreatment. Then the ambient ionization is performed by applying a high potential on the wetted porous material. In certain embodiments, the porous material is paper, which is a type of porous material that contains numerical pores and microchannels for liquid transport. The pores and microchannels also allow the paper to act as a filter device, which is beneficial for analyzing physically dirty or contaminated samples.

In other embodiments, the porous material is treated to produce microchannels in the porous material or to enhance the properties of the material for use as a probe of the invention. For example, paper may undergo a patterned silanization process to produce microchannels or structures on the paper. Such processes involve, for example, exposing the surface of the paper to tridecafluoro-1,1,2,2-tetrahydrooctyl-1-trichlorosilane to result in silanization of the paper. In other embodiments, a soft lithography process is used to produce microchannels in the porous material or to enhance the properties of the material for use as a probe of the invention. In other embodiments, hydrophobic trapping regions are created in the paper to pre-concentrate less hydrophilic compounds.

Hydrophobic regions may be patterned onto paper by using photolithography, printing methods or plasma treatment to define hydrophilic channels with lateral features of 200~1000 μm. See Martinez et al. (*Angew. Chem. Int. Ed.* 2007, 46, 1318-1320); Martinez et al. (*Proc. Natl Acad. Sci. USA* 2008, 105, 19606-19611); Abe et al. (*Anal. Chem.* 2008, 80, 6928-6934); Bruzewicz et al. (*Anal. Chem.* 2008, 80, 3387-3392); Martinez et al. (*Lab Chip* 2008, 8, 2146-2150); and Li et al. (*Anal. Chem.* 2008, 80, 9131-9134), the content of each of which is incorporated by reference herein in its entirety. Liquid samples loaded onto such a paper-based device can travel along the hydrophilic channels driven by capillary action.

Another application of the modified surface is to separate or concentrate compounds according to their different affinities with the surface and with the solution. Some compounds are preferably absorbed on the surface while other chemicals in the matrix prefer to stay within the aqueous phase. Through washing, sample matrix can be removed while compounds of interest remain on the surface. The compounds of interest can be removed from the surface at a later point in time by other high-affinity solvents. Repeating the process helps desalt and also concentrate the original sample.

Methods and systems of the invention use a porous material, e.g., paper, to hold and transport analytes for mass spectral analysis. Analytes in samples are pre-concentrated, enriched and purified in the porous material in an integrated fashion for generation of ions with application of a high voltage to the porous material. In certain embodiments, a discrete amount of transport solution (e.g., a droplet or a few droplets) is applied to assist movement of the analytes through the porous material. In certain embodiments, the analyte is already in a solution that is applied to the porous material. In such embodiments, no additional solvent need be added to the porous material. In other embodiments, the analyte is in a powdered sample that can be easily collected by swabbing a surface. Systems and methods of the invention allow for analysis of plant or animal tissues, or tissues in living organisms.

Methods and systems of the invention can be used for analysis of a wide variety of small molecules, including epinephrine, serine, atrazine, methadone, roxithromycin, cocaine and angiotensin I. All display high quality mass and MS/MS product ion spectra (see Examples below) from a variety of porous surfaces. Methods and systems of the invention allow for use of small volumes of solution, typically a few μL, with analyte concentrations on the order of 0.1 to 10 μg/mL (total amount analyte 50 pg to 5 ng) and give signals that last from one to several minutes.

Methods and systems of the invention can be used also for analysis of a wide variety of biomolecules, including proteins and peptides. Methods of the invention can also be used to analyze oligonucleotides from gels. After electrophoretic separation of oligonucleotides in the gel, the band or bands of interest are blotted with porous material using methods known in the art. The blotting results in transfer of at least some of the oligonucleotides in the band in the gel to the porous material. The porous material is then connected to a high voltage source and the oligonucleotides are ionized and sprayed into a mass spectrometer for mass spectral analysis.

Methods and systems of the invention can be used for analysis of complex mixtures, such as whole blood or urine.

The typical procedure for the analysis of pharmaceuticals or other compounds in blood is a multistep process designed to remove as many interferences as possible prior to analysis. First, the blood cells are separated from the liquid portion of blood via centrifugation at approximately 1000×g for 15 minutes (Mustard, J. F.; Kinlough-Rathbone, R. L.; Packham, M. A. *Methods in Enzymology*; Academic Press, 1989). Next, the internal standard is spiked into the resulting plasma and a liquid-liquid or solid-phase extraction is performed with the purpose of removing as many matrix chemicals as possible while recovering nearly all of the analyte (Buhrman, D. L.; Price, P. I.; Rudewicz, P. J. *Journal of the American Society for Mass Spectrometry* 1996, 7, 1099-1105). The extracted phase is typically dried by evaporating the solvent and then resuspended in the a solvent used as the high performance liquid chromatography (HPLC) mobile phase (Matuszewski, B. K.; Constanzer, M. L.; Chavez-Eng, C. M., Ithaca, N.Y., Jul. 23-25 1997; 882-889). Finally, the sample is separated in the course of an HPLC run for approximately 5-10 minutes, and the eluent is analyzed by electrospray ionization-tandem mass spectrometry (Hopfgartner, G.; Bourgogne, E. *Mass Spectrometry Reviews* 2003, 22, 195-214).

Methods and systems of the invention avoid the above sample work-up steps. Methods and systems of the invention analyze a dried blood spots in a similar fashion, with a slight modification to the extraction procedure. First, a specialized device is used to punch out identically sized discs from each dried blood spot. The material on these discs is then extracted in an organic solvent containing the internal standard (Chace, D. H.; Kalas, T. A.; Naylor, E. W. *Clinical Chemistry* 2003, 49, 1797-1817). The extracted sample is dried on the paper substrate, and the analysis proceeds as described herein.

Examples below show that methods and systems of the invention can directly detect individual components of complex mixtures, such as caffeine in urine, 50 pg of cocaine on a human finger, 100 pg of heroin on a desktop surface, and hormones and phospholipids in intact adrenal tissue, without the need for sample preparation prior to analysis (See Examples below). Methods and systems of the invention allow for simple imaging experiments to be performed by examining, in rapid succession, needle biopsy tissue sections transferred directly to paper.

Analytes from a solution are applied to the porous material for examination and the solvent component of the solution can serve as the electrospray solvent. In certain embodiments, analytes (e.g., solid or solution) are pre-spotted onto the porous material, e.g., paper, and a solvent is applied to the material to dissolve and transport the analyte into a spray for mass spectral analysis.

In certain embodiments, a solvent is applied to the porous material to assist in separation/extraction and ionization. Any solvents may be used that are compatible with mass spectrometry analysis. In particular embodiments, favorable solvents will be those that are also used for electrospray ionization. Exemplary solvents include combinations of water, methanol, acetonitrile, and THF. The organic content (proportion of methanol, acetonitrile, etc. to water), the pH, and volatile salt (e.g. ammonium acetate) may be varied depending on the sample to be analyzed. For example, basic molecules like the drug imatinib are extracted and ionized more efficiently at a lower pH. Molecules without an ionizable group but with a number of carbonyl groups, like sirolimus, ionize better with an ammonium salt in the solvent due to adduct formation.

In certain embodiments, a multi-dimensional approach is undertaken. For example, the sample is separated along one dimension, followed by ionization in another dimension. In these embodiments, separation and ionization can be individually optimized, and different solvents can be used for each phase.

In other embodiments, transporting the analytes on the paper is accomplished by a solvent in combination with an electric field. When a high electric potential is applied, the direction of the movement of the analytes on paper is found to be related to the polarity of their charged forms in solution. Pre-concentration of the analyte before the spray can also be achieved on paper by placing an electrode at a point on the wetted paper. By placing a ground electrode near the paper tip, a strong electric field is produced through the wetted porous material when a DC voltage is applied, and charged analytes are driven forward under this electric field. Particular analytes may also be concentrated at certain parts of the paper before the spray is initiated.

In certain embodiments, chemicals are applied to the porous material to modify the chemical properties of the porous material. For example, chemicals can be applied that allow differential retention of sample components with different chemical properties. Additionally, chemicals can be applied that minimize salt and matrix effects. In other embodiments, acidic or basic compounds are added to the porous material to adjust the pH of the sample upon spotting. Adjusting the pH may be particularly useful for improved analysis of biological fluids, such as blood. Additionally, chemicals can be applied that allow for on-line chemical derivatization of selected analytes, for example to convert a non-polar compound to a salt for efficient electrospray ionization.

In certain embodiments, the chemical applied to modify the porous material is an internal standard. The internal standard can be incorporated into the material and released at known rates during solvent flow in order to provide an internal standard for quantitative analysis. In other embodiments, the porous material is modified with a chemical that allows for pre-separation and pre-concentration of analytes of interest prior to mass spectrum analysis.

The spray droplets can be visualized under strong illumination in the positive ion mode and are comparable in size to the droplets emitted from a nano-electrospray ion sources (nESI). In the negative ion mode, electrons are emitted and can be captured using vapor phase electron capture agents like benzoquinone. Without being limited by any particular theory or mechanism of action, it is believed that the high electric field at a tip of the porous material, not the fields in the individual fluid channels, is responsible for ionization.

The methodology described here has desirable features for clinical applications, including neotal screening, therapeutic drug monitoring and tissue biopsy analysis. The procedures are simple and rapid. The porous material serves a secondary role as a filter, e.g., retaining blood cells during analysis of whole blood. Significantly, samples can be stored on the porous material and then analyzed directly from the stored porous material at a later date without the need transfer from the porous material before analysis. Systems of the invention allow for laboratory experiments to be performed in an open laboratory environment.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The following examples are intended to further illustrate certain embodiments of the invention, and are not to be construed to limit the scope of the invention. Examples herein show that mass spectrometry probes of the invention can ionize chemical and biological samples, allowing for subsequent mass analysis and detection. An exemplary probe was constructed as a paper triangle, which was used to generate micron scale droplets by applying a high potential on the paper. The analytes were ionized from these electrically charged droplets and transported into a conventional mass spectrometer.

Examples below show that a wide range of samples could be directly analyzed in the ambient environment by probes of the invention in both of pure state and complex mixtures. The results showed that paper-based spray has the following benefits: it operated without sheath gas, i.e., few accessories were required for in situ analysis; biological samples (dried blood, urine) could be stored on the precut filter papers for months before analysis; filter paper minimized matrix effects seen with electrospray or nano electrospray in many samples (blood cells, salt and proteins) and enhanced the MS signal of chemicals in complex samples; powdered samples were easily collected by swabbing surfaces using paper pieces and then directly analyzed; the paper could be pretreated to contain internal standards that were released at known rates during solvent flow in quantitative analysis; and the paper could be pretreated to contain matrix suppression or absorption sites or to perform ion exchange or to allow on-line chemical derivatization of selected analytes.

Detection of most analytes was achieved as low as ppb levels (when examined as solutions) or in the low ng to pg range (when solids were examined) and the detection time was less than one minute. Certain Examples below provide a protocol for analyzing a dried blood spot, which can also be used for in situ analysis of whole blood samples. The dried blood spot method is also demonstrated to be compatible with the storage and transport of blood sample for blood screening and other clinical tests.

Devices of the invention integrated the capabilities of sampling, pre-separation, pre-concentration and ionization. Methods and systems of the invention simplify the problem of sample introduction in mass analyzers.

Example 1: Construction of an MS Probe

Figure 1B:
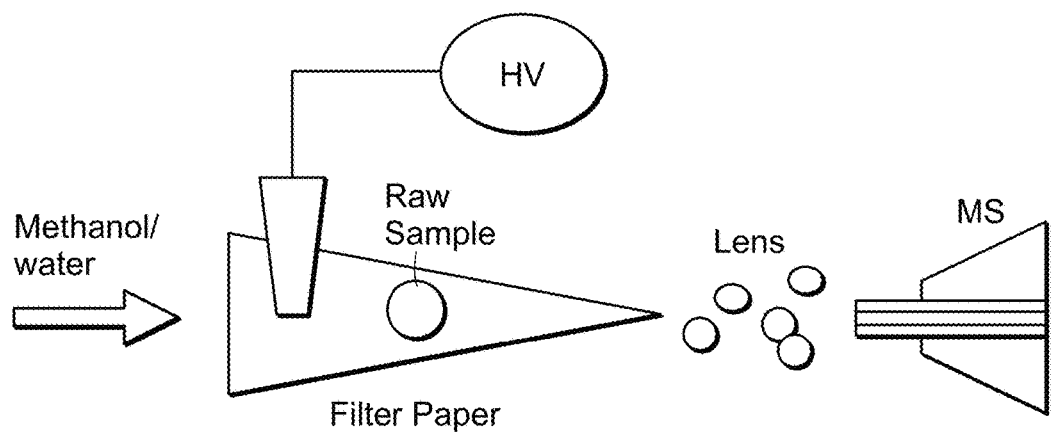
FIG. 1B is a drawing of a sample solution pre-spotted onto the paper and a droplet of solvent being subsequently supplied to the paper for electrospray ionization.

Filter paper was cut into triangular pieces with dimensions of 10 mm long and 5 mm wide and used as a sprayer (FIGS. 1A-B). A copper clip was attached to the paper, and the paper was oriented to face an inlet of a mass spectrometer (FIGS. 1A-B). The copper clip was mounted on a 3D moving stage to accurately adjust its position. A high voltage was applied to the copper clip and controlled by a mass spectrometer to generate analyte ions for mass detection.

Samples were directly applied to the paper surface that served as a sample purification and pre-concentration device. Filter paper allowed liquid samples to move through the hydrophilic network driven by capillary action and electric effects and to transport them to the tip of the paper. Separation could take place during this transport process. Sample solution was sprayed from the tip and resulted in ionization and MS detection when a high voltage (~4.5 kV) was applied to the paper surface.

All experiments were carried out with a Finnigan LTQ mass spectrometer (Thermo Electron, San Jose, Calif.). The typical temperature of the capillary inlet was set at 150° C. while 30° C. for heroin detection. The lens voltage was set at 65 V for sample analysis and 240 V for survival yield experiment. Tandem mass spectra were collected using collision-induced dissociation (CID) to identify analytes in tested samples, especially for complex mixtures and blood samples.

Example 2: Spray Generation

Spray was produced by applying a high potential on the wetted paper triangle. One paper triangle was placed in front of the inlet of LTQ with its sharp tip facing to the inlet, separated by 3 mm or more. Typically, 10 uL sample solution was applied to wet the paper triangle. The solution can wet or saturate the paper or form a thin layer of liquid film on the surface of the paper. A high potential (3-5 kV) was applied between the paper triangle and mass inlet to generate an electric field, which induced a charge accumulation on the liquid at the tip of paper triangle. The increasing coulombic force breaks the liquid to form charged droplets and then the solvent evaporated during the flight of droplets from the paper tip to the mass analyzer. Paper spray required no sheath gas, heating or any other assistance to remove the solvent.

When liquid accumulated on the paper triangle, a Taylor cone was observed at the tip when examined with a microscope. The droplets formed were clearly visible under strong illumination. The Taylor cone and visible spray disappeared after a short time of evaporation and spray. However, the mass signal lasted for a much longer period (several minutes). This revealed that the paper triangle could work in two modes for mass analysis. In a first mode, the liquid was transported inside the paper at a rate faster than the liquid could be consumed as spray at the paper tip, resulting in a large cone being formed at the paper tip and droplets being generated. In a second mode, the liquid transport inside the paper was not able to move at a rate fast enough to keep up with the spray consumption, and droplets were not visible. However, it was observed that ionization of analytes did take place. The first mode provided ESI like mass spectra and the second mode provided spectra with some of the features APCI spectra. In the latter case, the paper triangle played a role analogous to a conductive needle to generate a high electric field to ionize the molecules in the atmosphere. It was observed that the mass signal in the first mode was stronger than the mass signal in the second mode by approximately two orders of magnitude under the conditions and for the samples tested.

Example 3: Probe Considerations

Probe Materials

A number of porous materials were tested to generate charged droplets for mass spectrometry. The materials were shaped into triangles having sharp tips and sample solution was then applied to the constructed probes. Data herein show that any hydrophilic and porous substrate could be used successfully, including cotton swab, textile, plant tissues as well as different papers. The porous network or microchannels of these materials offered enough space to hold liquid and the hydrophilic environment made it possible for liquid transport by capillary action. Hydrophobic and porous substrates could also be used successfully with properly selected hydrophobic solvents.

For further investigation, six kinds of commercialized papers were selected and qualitatively tested to evaluate their capabilities in analyte detection. Filter papers and chromatography paper were made from cellulose, while glass microfiber filter paper was made from glass microfiber. FIGS. 19A-F show the mass spectra of cocaine detection on those papers. The spectrum of glass fiber paper (FIG. 19E) was unique because the intensity of background was two orders of magnitude lower than other papers and the cocaine peak (m/z, 304) could not be identified.

Figure 19A:
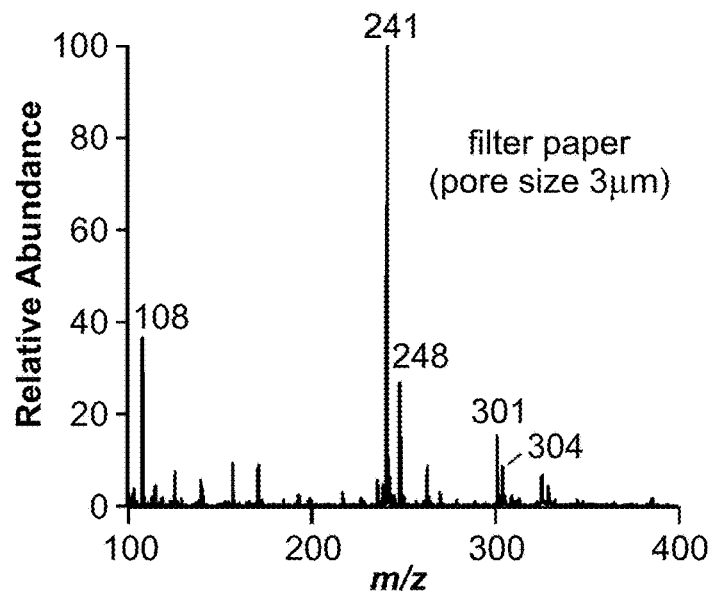
FIGS. 19A-F show mass spectra of cocaine sprayed from six different types of paper (Whatman filter paper with different pore sizes.
Figure 19B:
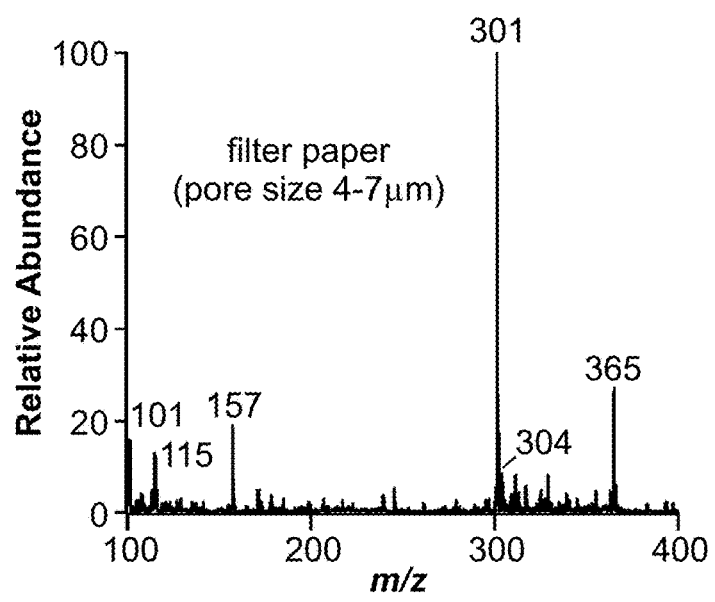
Figure 19C:
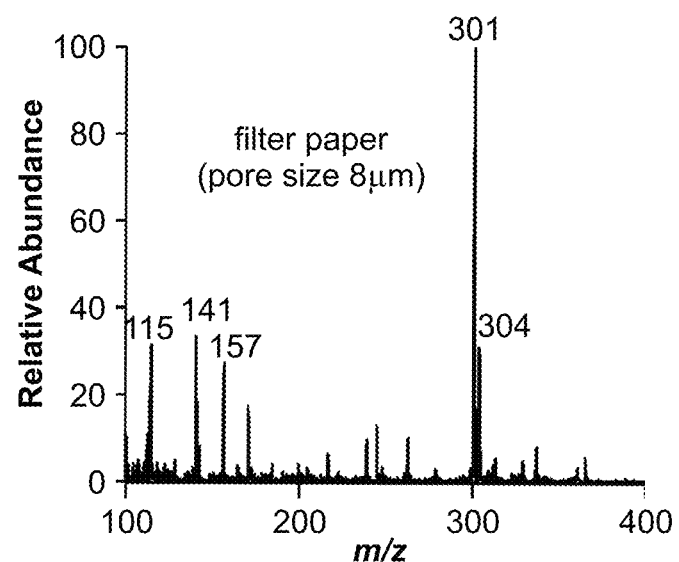
Figure 19D:
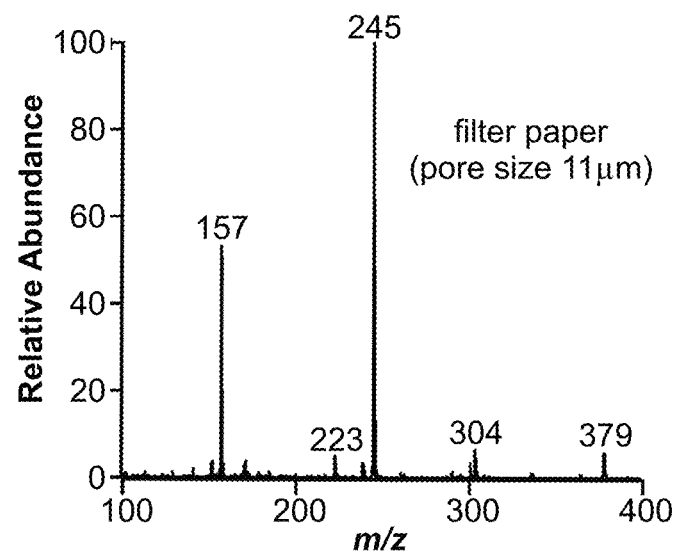
Figure 19E:
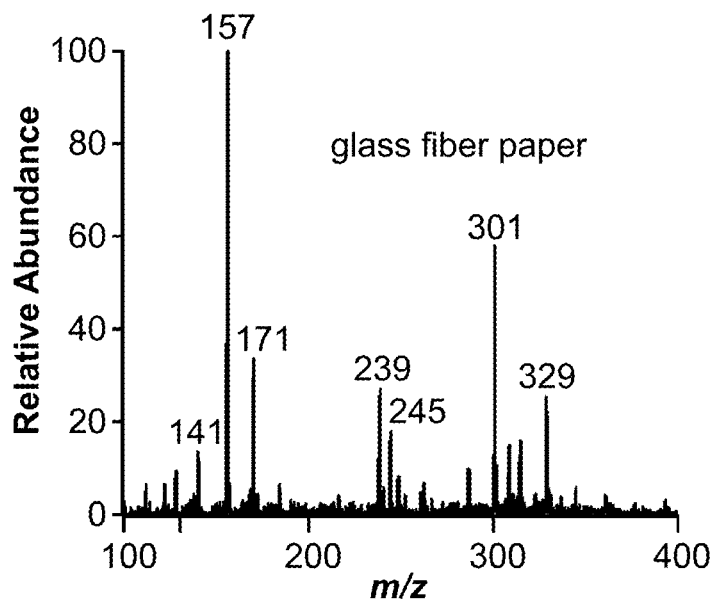
Figure 19F:
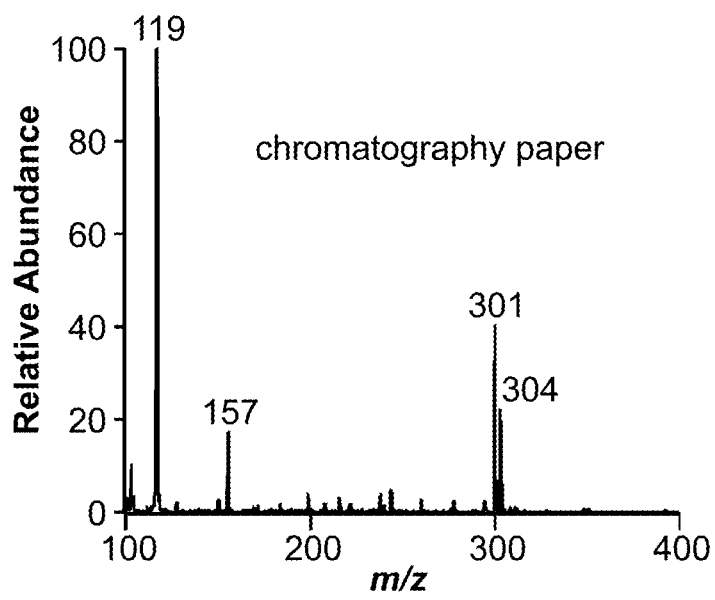

It was hypothesized that the glass fiber paper was working on mode II and prohibiting efficient droplet generation, due to the relative large thickness (~2 mm). This hypothesis was proved by using a thin layer peeled from glass fiber paper for cocaine detection. In that case, the intensity of the background increased and a cocaine peak was observed. All filter papers worked well for cocaine detection, (FIGS. 19A-D). Chromatography paper showed the cleanest spectrum and relative high intensity of cocaine (FIG. 19F).

Probe Shape and Tip Angle

Figure 25C:
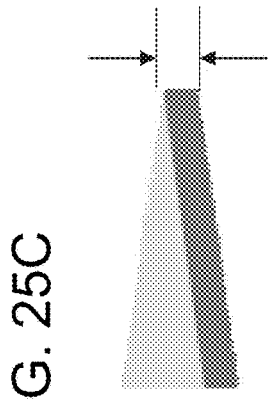
FIGS. 25A-E show different shapes, thicknesses, and angles for probes of the invention.
Figure 25B:
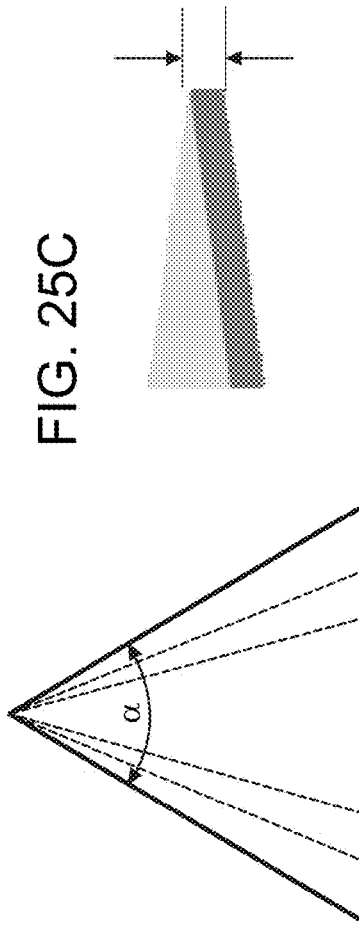
Figure 25A:
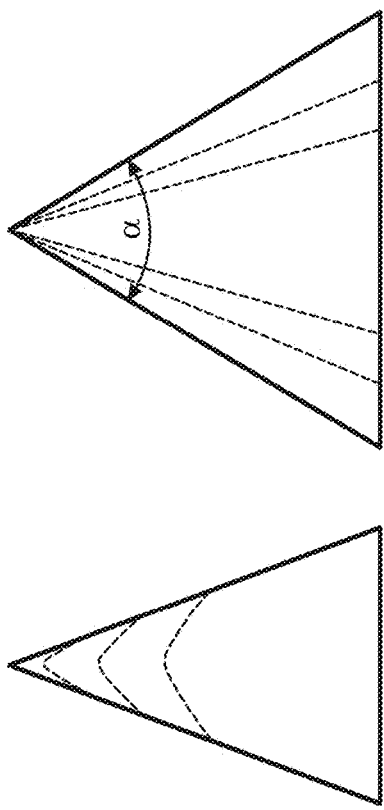
Figure 25E:
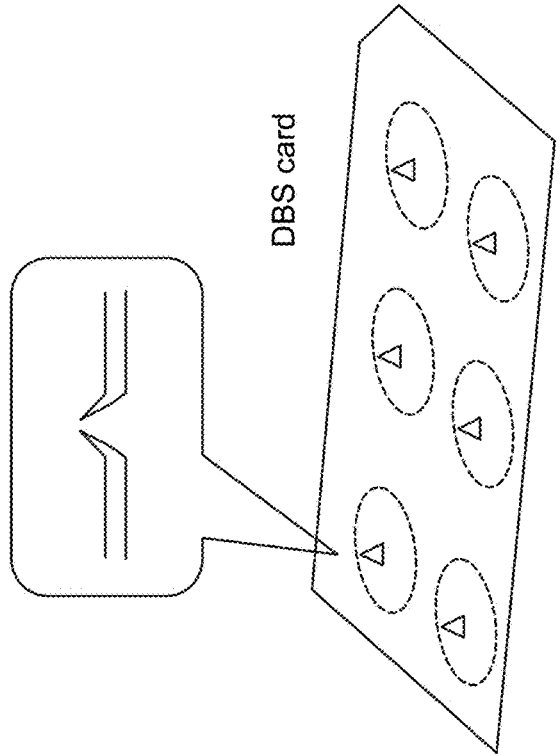
Figure 25D:
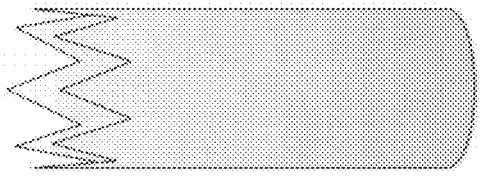
Figure 26A:
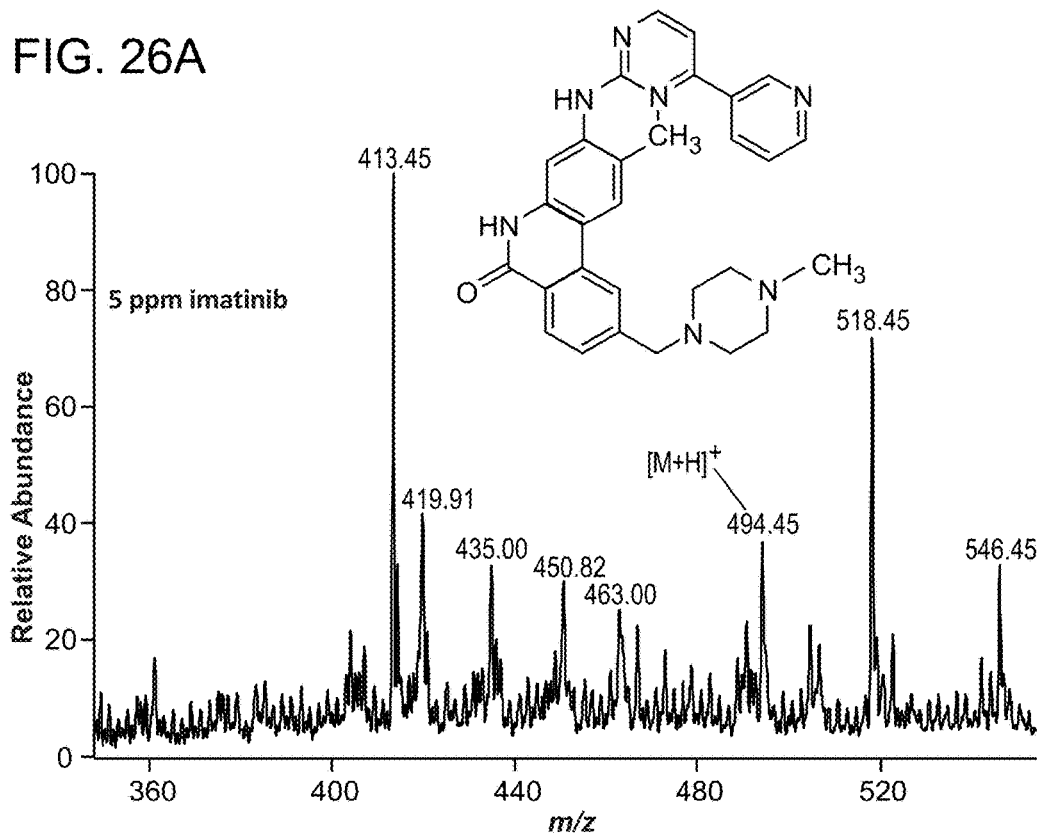
FIGS. 26A-B are a set of mass spectra of imatinib from human serum using direct spray from a C4 zip-tip of conical shape. Human serum samples (1.5 µL each) containing imatinib were passed through the porous C4 extraction material three times and then 3 µL methanol was added onto the zip-tip with 4 kV positive DC voltage applied to produce the spray.
Figure 26B:
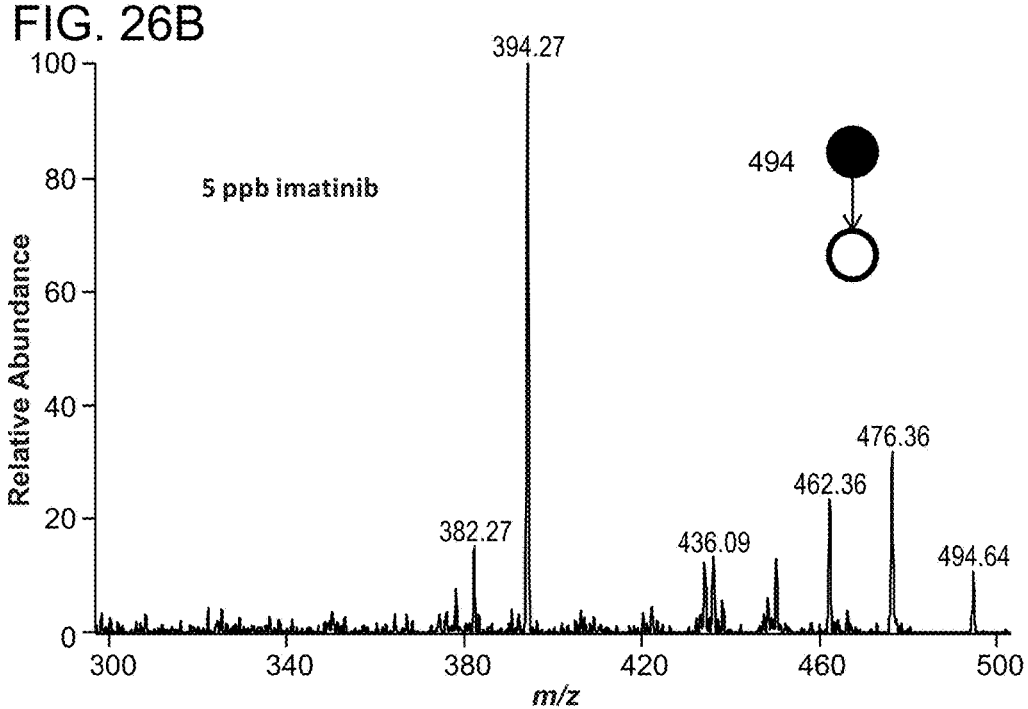
Figure 27A:
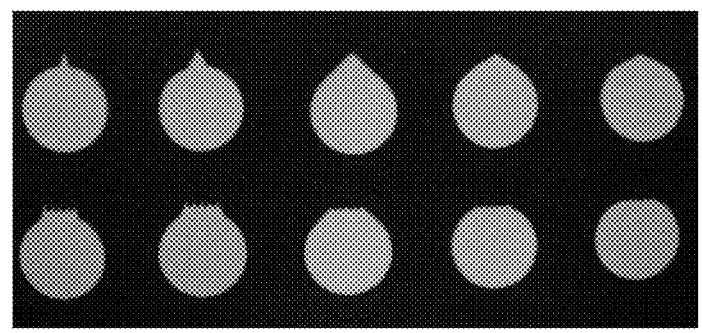
FIG. 27A is a picture showing different tip angles for probes of the invention. From left to right, the angles are 30, 45, 90, 112, 126 degree, respectively.
Figure 27B:
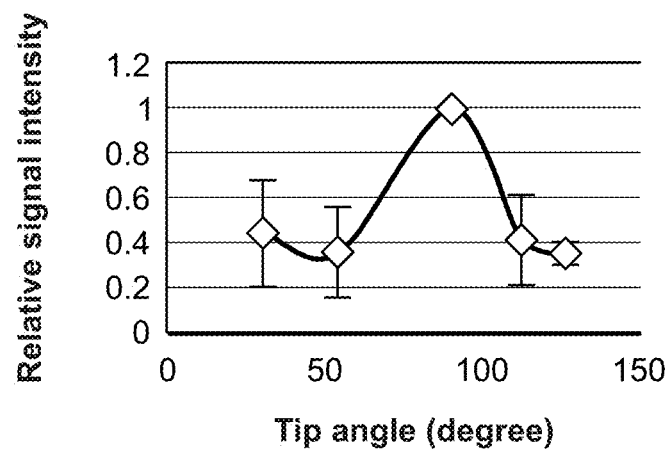
FIG. 27B is a graph showing the effect of angle on MS signal intensity. All MS signals were normalized to the MS signal using the 90 degree tip.

Many different probe shapes were investigated with respect to generating droplets. A preferred shape of the porous material included at least one tip. It was observed that the tip allowed ready formation of a Taylor cone. A probe shape of a triangle was used most often. As shown in FIGS. 25A-C, the sharpness of the tip, the angle of the tip (FIGS. 27A-B), and the thickness of the paper substrate could effect the spray characteristics. The device of a tube shape with multiple tips (FIG. 25D) is expected to act as a multiple-tip sprayer, which should have improved spray efficiency. An array of micro sprayers can also be fabricated on a DBS card using sharp needles to puncture the surface (FIG. 25E).

Example 4: Configuration of Probe with Inlet of a Mass Spectrometer

Figure 20A:
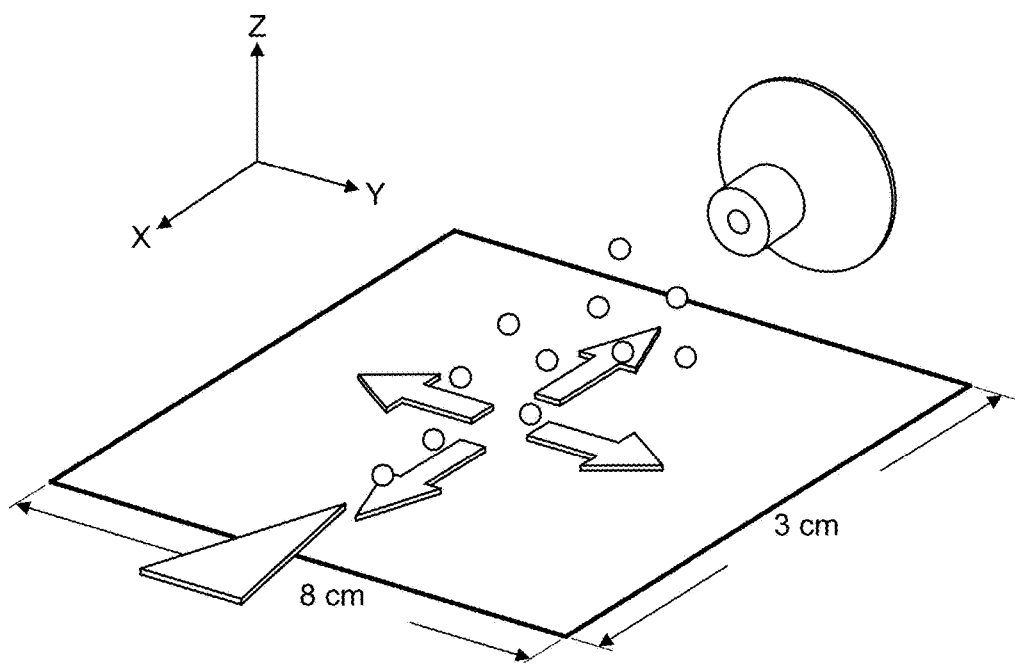
FIG. 20A shows a schematic setup for characterizing the spatial distribution of paper spray.
Figure 20B:
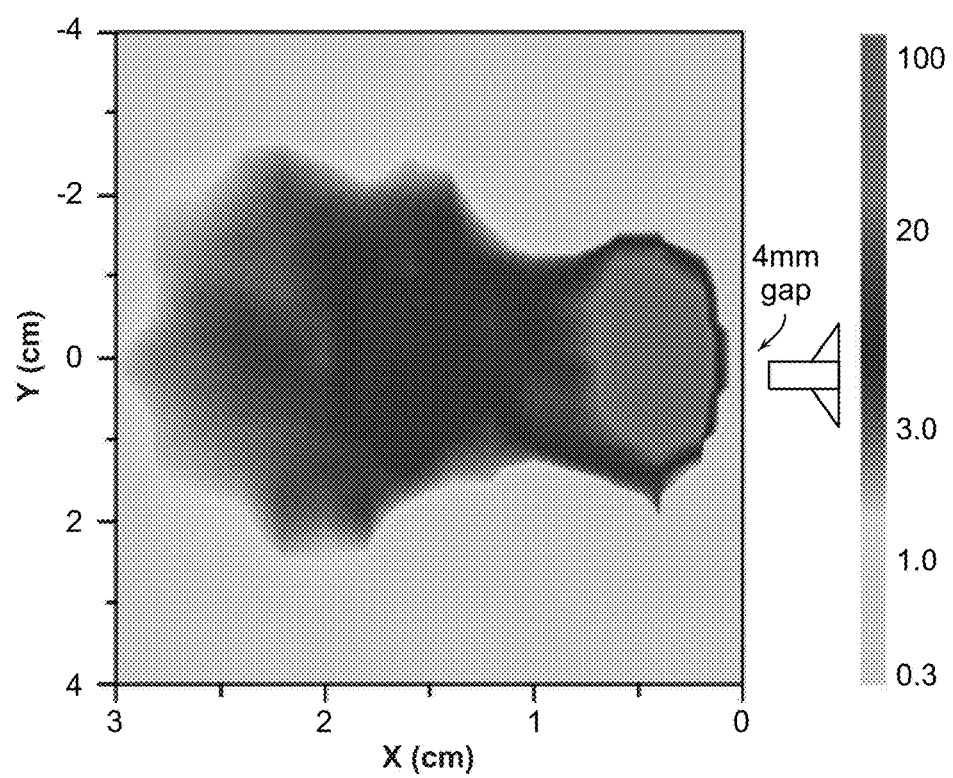
FIG. 20B is a 2D contour plot showing the relative intensity of m/z 304 when the probe is moved in the x-y plane with respect to the inlet of the mass spectrometer.

A paper triangle was mounted on a 2D moving stage to determine how the mass signal was affected by the relative positions of the paper triangle and the mass spectrometer inlet. The paper triangle was moved 8 cm in the y-direction in a continuous manner and 3 cm in the x-direction with a 2 mm increment for each step (FIG. 20A). Cocaine solution (1 ug/mL, methanol/water, 1:1 v/v) was continuously fed onto the paper surface. The mass spectrum was continuously recorded during the entire scan. A contour plot of the peak intensity of protonated cocaine (m/z, 304) was created from the normalized data extracted from the mass spectrum (FIG. 20B). The contour plot shows that it was not necessary for the paper triangle to be placed directly in-line with the inlet of the mass spectrometer to generate droplets.

Figure 20C:
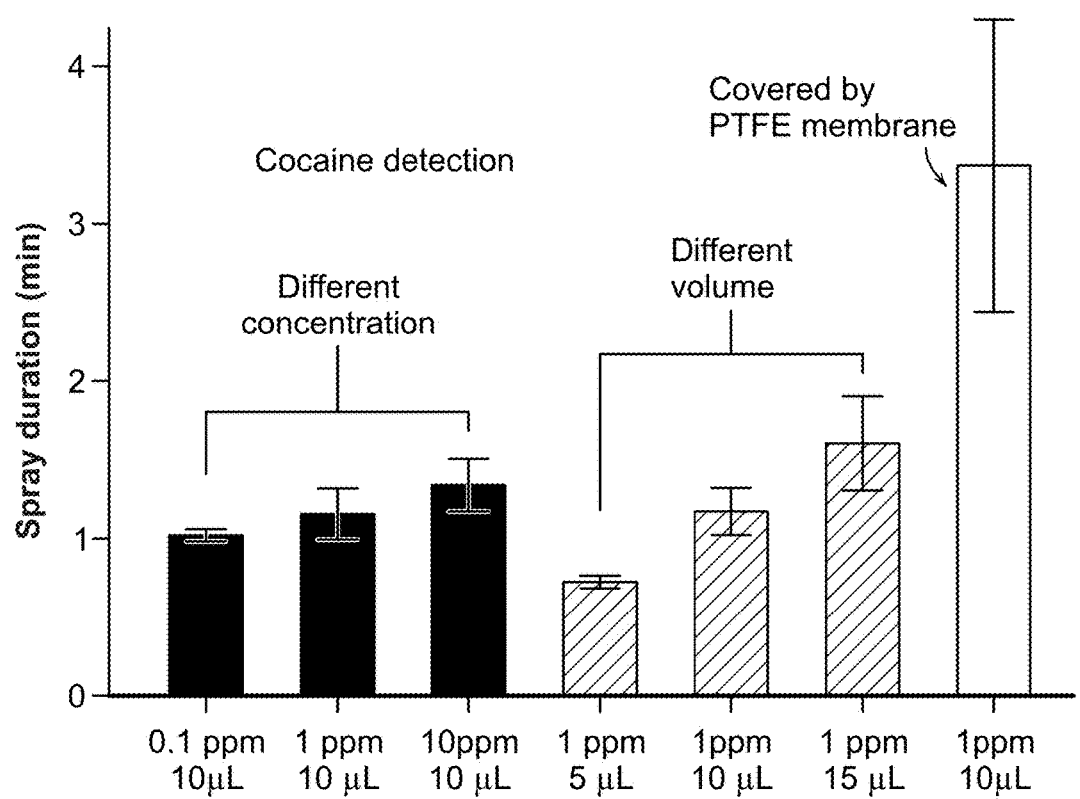
FIG. 20C is a graph showing signal duration of m/z 304 when loading cocaine solution on paper with different concentrations or volumes, or sealed by Teflon membrane.

Spray duration was also tested (FIG. 20C). Paper triangles (size 10 mm, 5 mm) were prepared. First, 10 uL solutions were applied on the paper triangles with different concentration of 0.1, 1 and 10 ug/mL. The spray time for each paper was just slightly varied by the difference of concentration. After that, 1 ug/mL cocaine solutions were applied on the paper triangles with different volumes of 5 uL, 10 uL and 15 uL. The spray times showed a linear response followed by the increasing sample volumes.

In another test, the paper was sealed with a PTFE membrane to prevent evaporation of solution, which prolonged the spray time by about three times. These results indicate that paper spray offers long enough time of spray for data acquisition even using 5 uL solution, and the intensity of signal is stable during the entire spray period.

Example 5: Separation and Detection

Figure 24B:
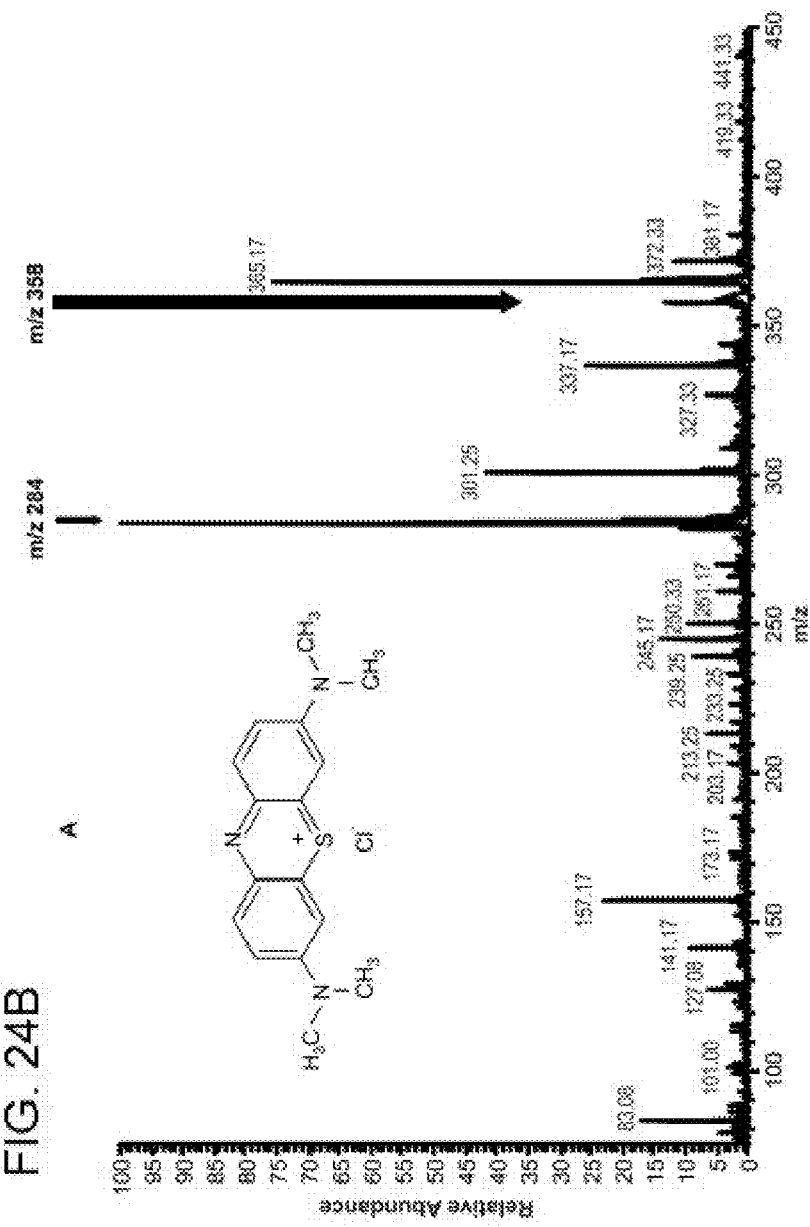
Figure 24C:
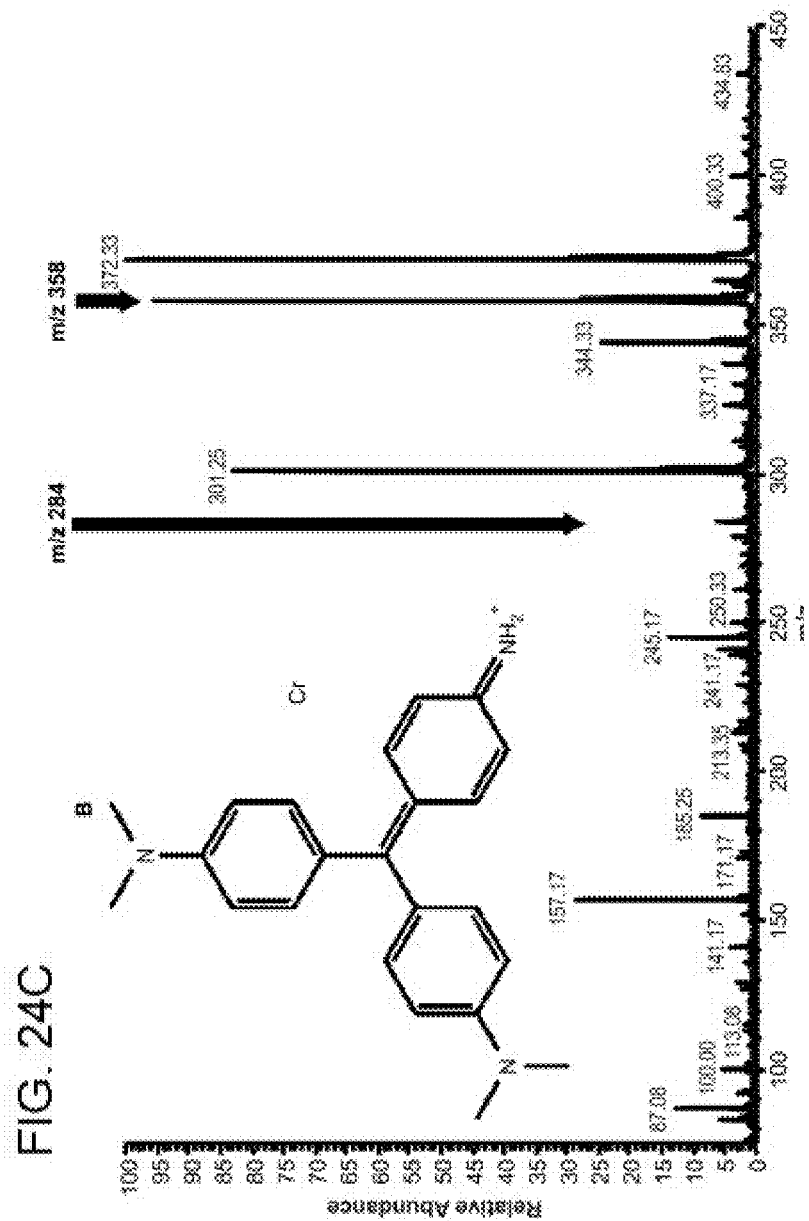

Probes of the invention include a porous material, such as paper, that can function to both separate chemicals in biological fluids before in situ ionization by mass spectrometry. In this Example, the porous material for the probe was chromatography paper. As shown in FIG. 24A-C, a mixture of two dyes was applied to the paper as a single spot. The dyes were first separated on the paper by TLC (thin layer chromatograph) and the separated dyes were examined using MS analysis by methods of the invention with the paper pieces cut from the paper media (FIGS. 24A-C). Data show the separate dyes were detected by MS analysis (FIGS. 24A-C).

The chromatography paper thus allowed for sample collection, analyte separation and analyte ionization. This represents a significant simplification of coupling chromatography with MS analysis. Chromatography paper is a good material for probes of the invention because such material has the advantage that solvent movement is driven by capillary action and there is no need for a syringe pump. Another advantage is that clogging, a serious problem for conventional nanoelectrospray sources, is unlikely due to its multi-porous characteristics. Therefore, chromatography paper, a multi-porous material, can be used as a microporous electrospray ionization source.

Example 6: Pure Compounds: Organic Drugs, Amino Acids, and Peptides

As already described, probes and methods of the invention offer a simple and convenient ionization method for mass spectrometry. Paper triangles were spotted with different compounds and connected to a high voltage source to produce ions. All experiments were carried out with a Finnigan LTQ mass spectrometer (Thermo Electron, San Jose, Calif.). Data herein show that a variety of chemicals could be ionized in solution phase, including amino acid, therapeutic drugs, illegal drugs and peptides.

Figure 2A:
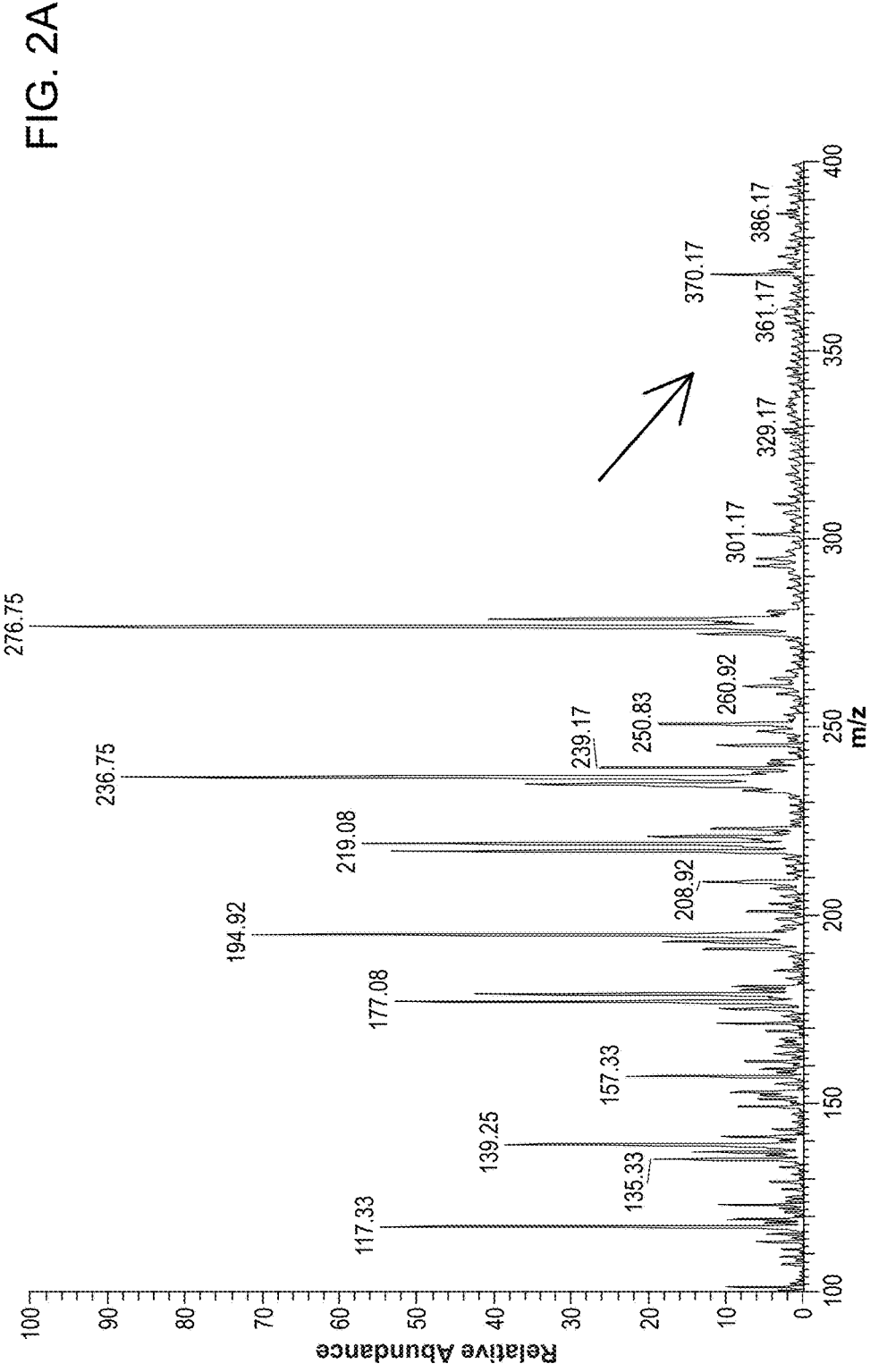
FIG. 2A is a MS spectrum of heroin (concentration: 1 ppm, volume: 10 µl, solvent: MeOH/$H_2O$/HOAc (50:49:1, v/v/v)) using probes of the invention.
Figure 2B:
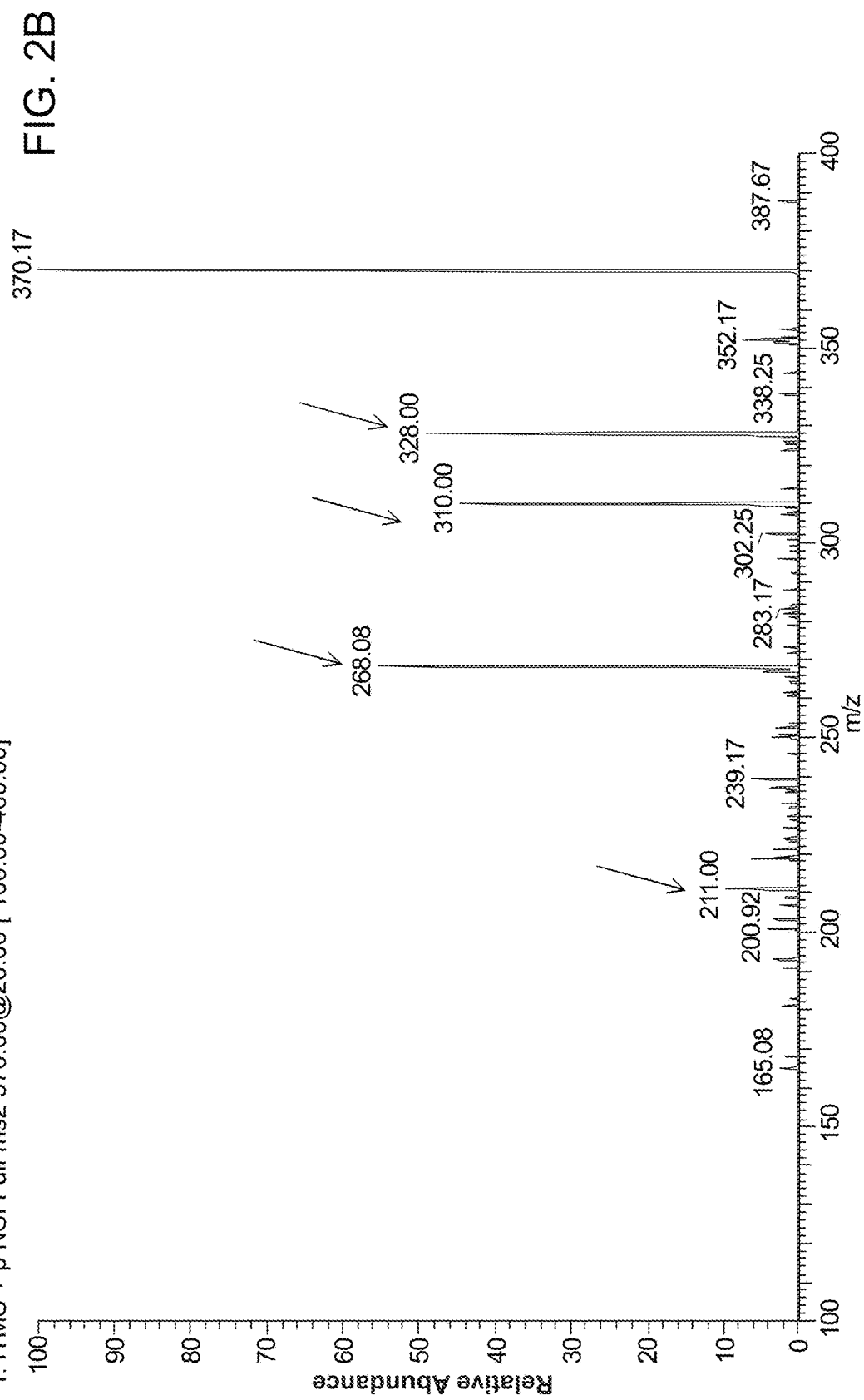
FIG. 2B is a MS/MS spectrum of heroin (concentration: 1 ppb, volume: 10 µl, solvent: MeOH/$H_2O$/HOAc (50:49:1, v/v/v)).

FIG. 2A shows an MS spectrum of heroin (concentration: 1 ppm, volume: 10 µl, solvent: MeOH/$H_2O$/HOAc (50:49:1, v/v/v)) using probes of the invention. FIG. 2B shows MS/MS spectrum of heroin (concentration: 1 ppb, volume: 10 µl, solvent: MeOH/$H_2O$/HOAc (50:49:1, v/v/v)).

Figure 3A:
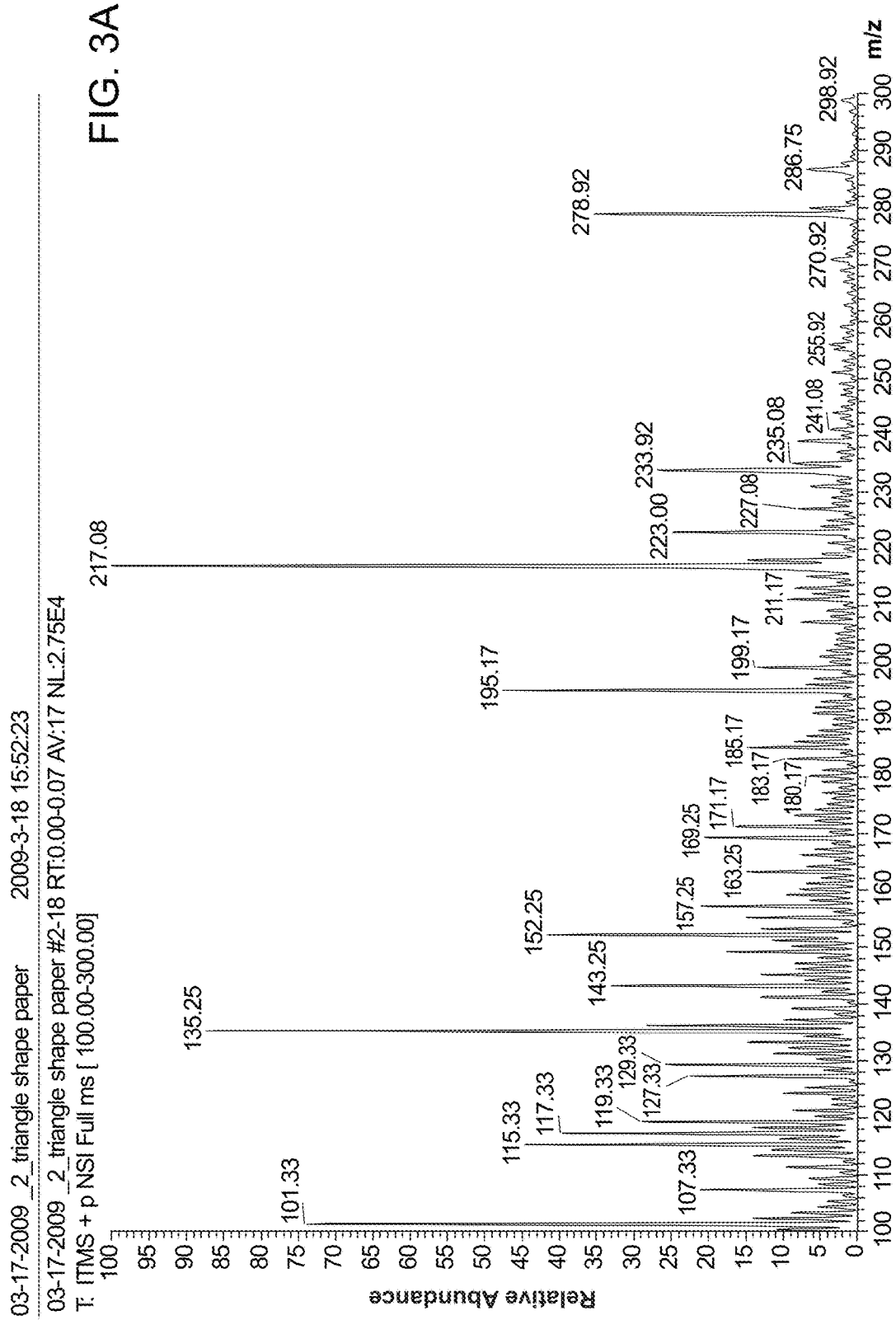
FIG. 3A is a MS spectrum of caffeine (concentration: 10 ppm, volume: 10 µl, solvent: MeOH/$H_2O$/HOAc (50:49:1, v/v/v)) using probes of the invention.
Figure 3B:
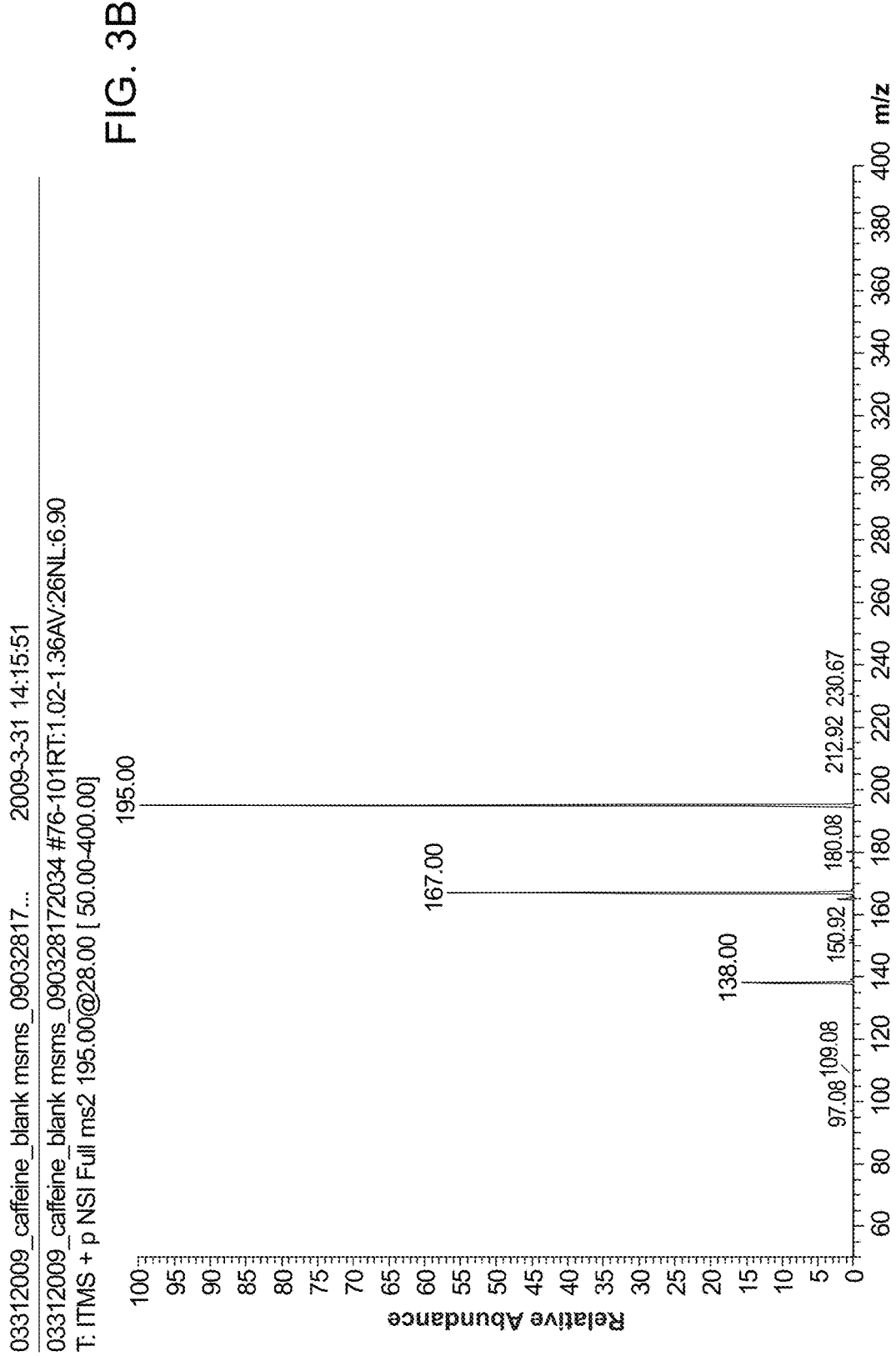
FIG. 3B is a MS/MS spectrum of caffeine (concentration: 10 ppb, volume: 10 µl, solvent: MeOH/$H_2O$/HOAc (50:49:1, v/v/v)).

FIG. 3A shows MS spectrum of caffeine (concentration: 10 ppm, volume: 10 µl, solvent: MeOH/$H_2O$/HOAc (50:49:1, v/v/v)) using probes of the invention. FIG. 3B shows MS/MS spectrum of caffeine (concentration: 10 ppb, volume: 10 µl, solvent: MeOH/$H_2O$/HOAc (50:49:1, v/v/v)). Peak 167 also exists in the blank spectrum with solvent and without caffeine.

Figure 4A:
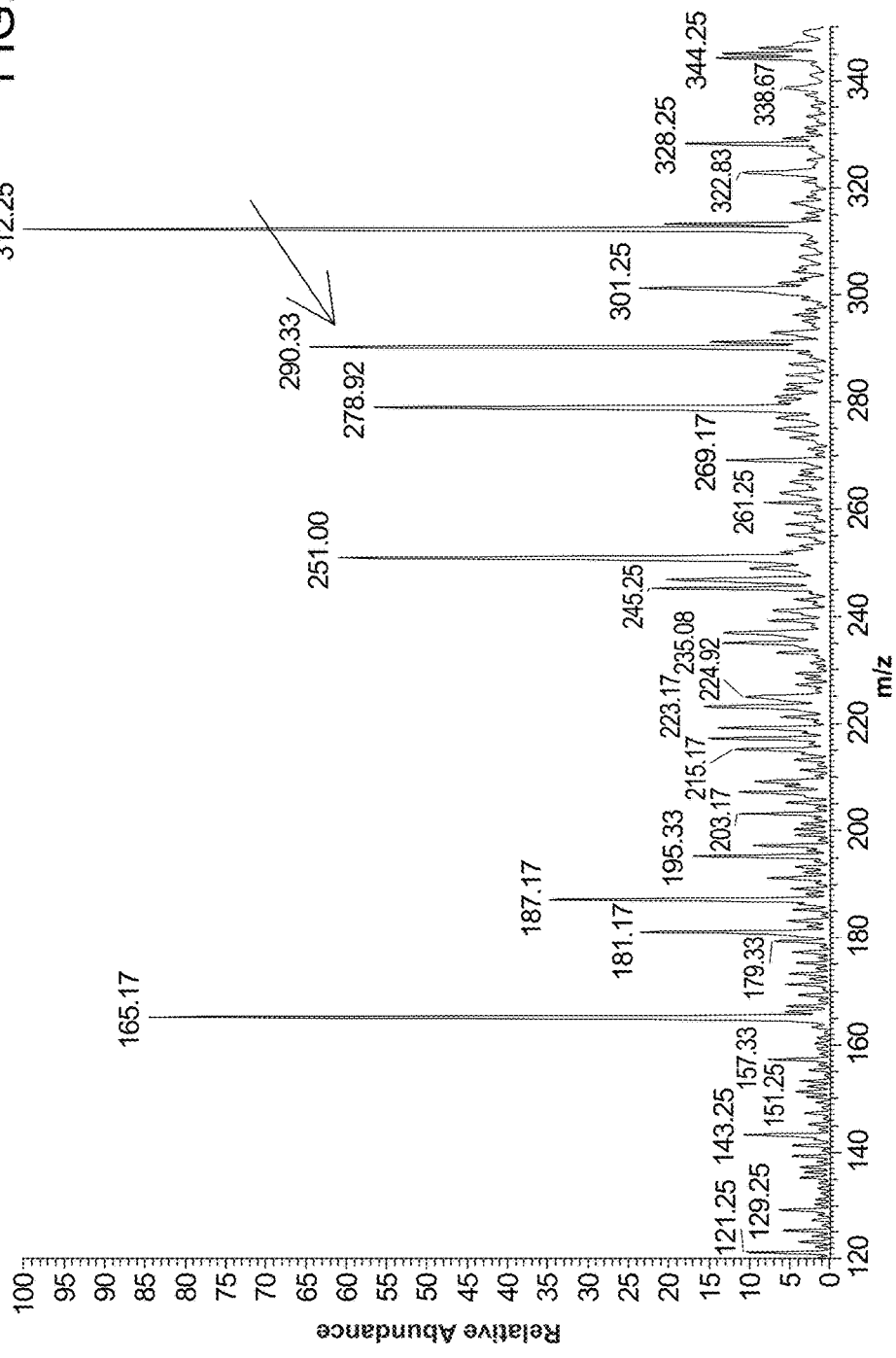
FIG. 4A is a MS spectrum of benzoylecgonine (concentration: 10 ppm, volume: 10 µl, solvent: MeOH/$H_2O$/HOAc (50:49:1, v/v/v)) using probes of the invention.

FIG. 4A shows MS spectrum of benzoylecgonine (concentration: 10 ppm, volume: 10 µl, solvent: MeOH/$H_2O$/HOAc (50:49:1, v/v/v)) using probes of the invention. FIG.

4B shows MS/MS spectrum of benzoylecgonine (concentration: 10 ppb, volume: 10 μl, solvent: MeOH/H$_2$O/HOAc (50:49:1, v/v/v)).

Figure 5A:
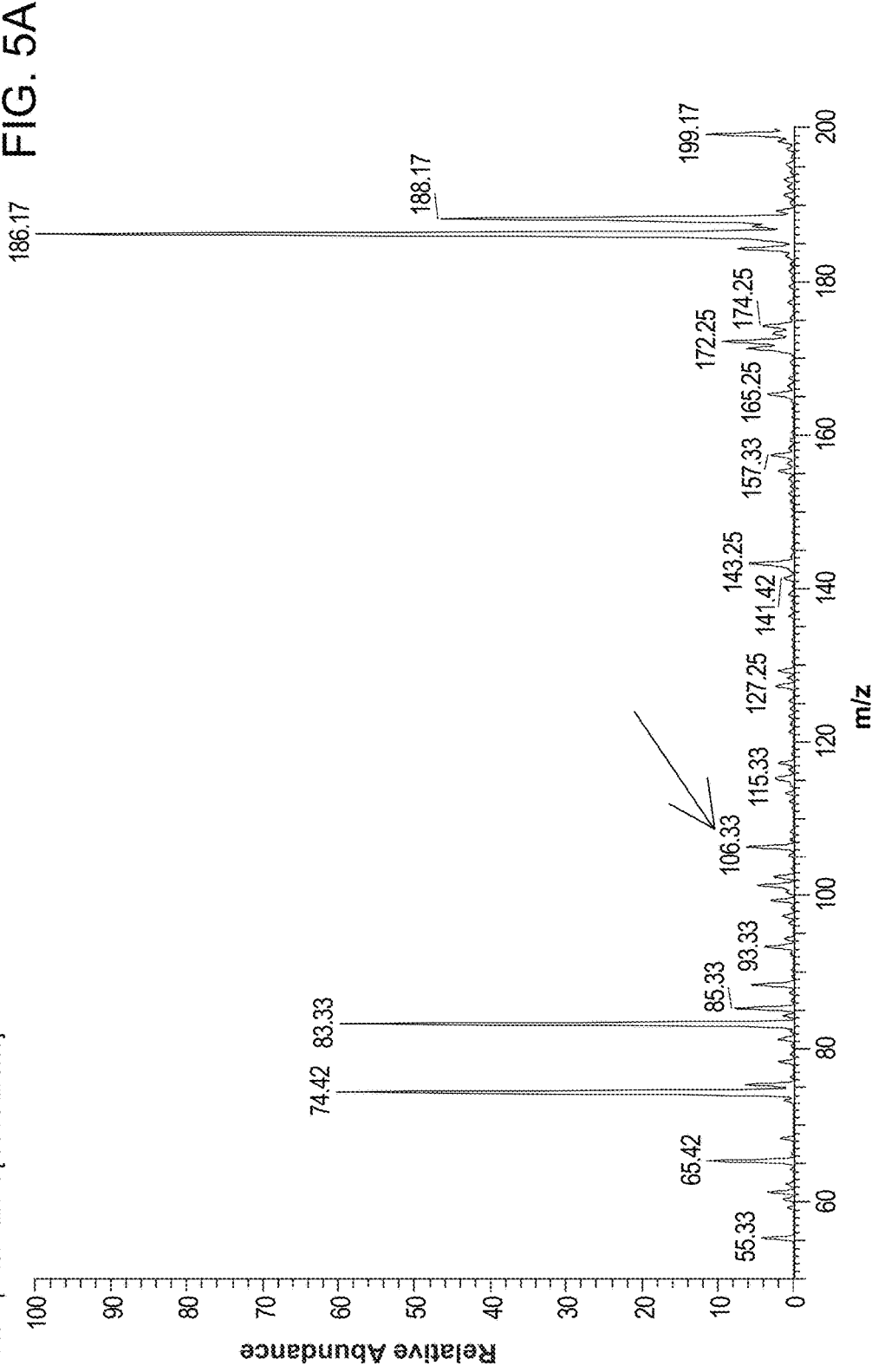
FIG. 5A is a MS spectrum of serine (concentration: 1 ppm, volume: 10 µl, solvent: MeOH/$H_2O$/HOAc (50:49:1, v/v/v)) using probes of the invention.
Figure 5B:
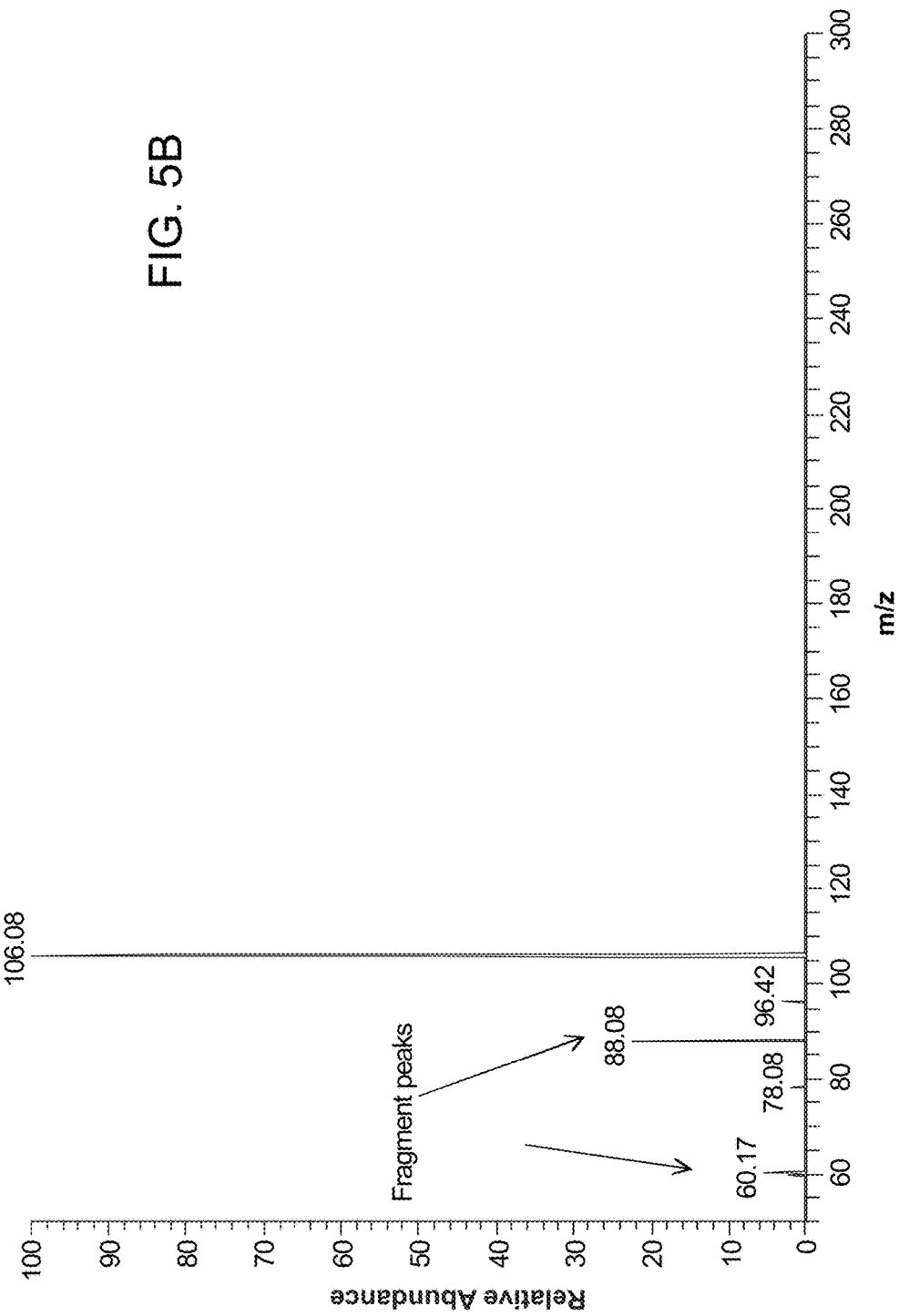
FIG. 5B is a MS/MS spectrum of serine (concentration: 100 ppb, volume: 10 µl, solvent: MeOH/$H_2O$/HOAc (50:49:1, v/v/v)).
Figure 21A:
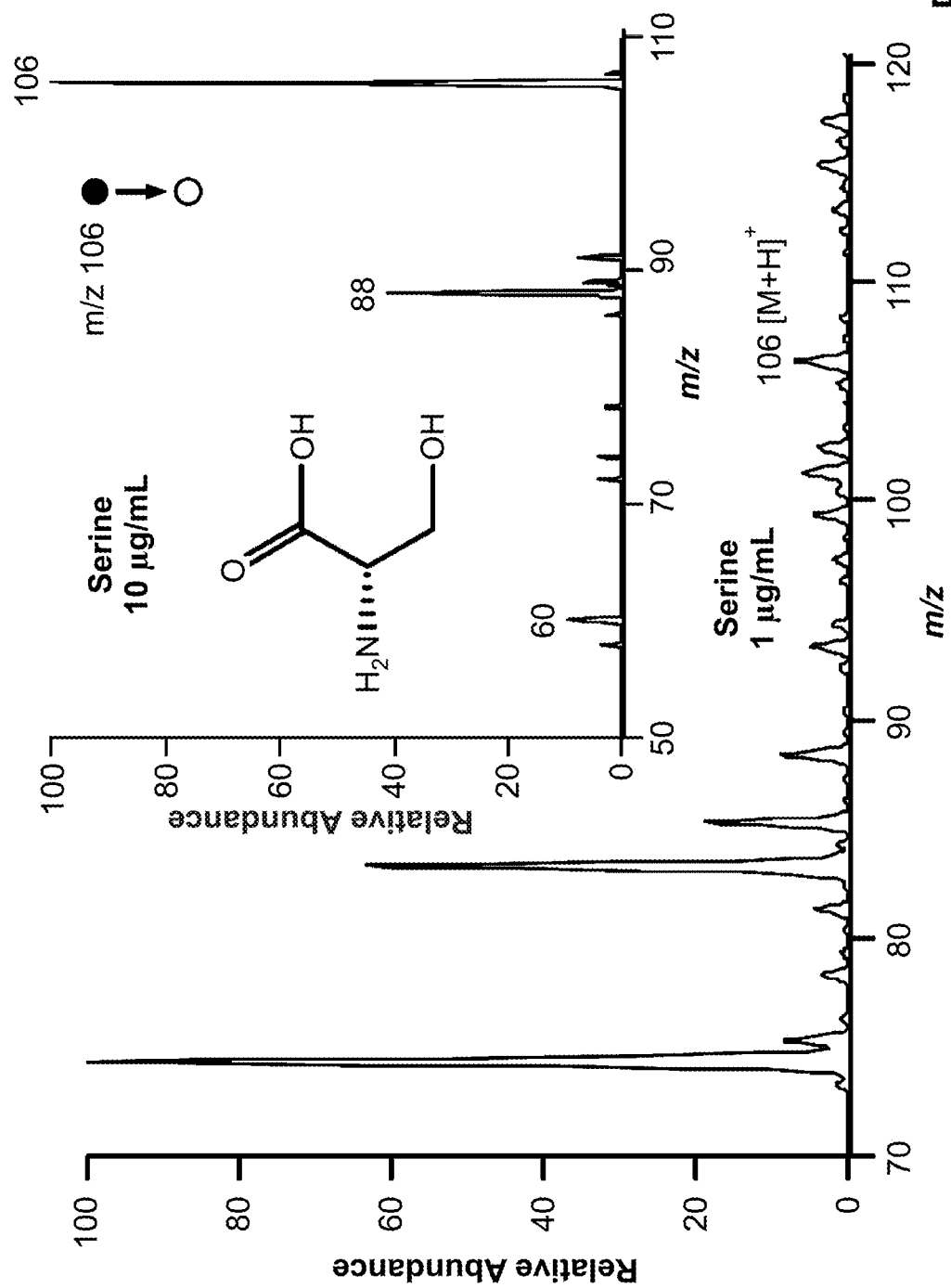
FIGS. 21A-D are a set of MS spectra of pure chemical solutions and their corresponding MS/MS spectra. Spectra were obtained for (FIG. 21A) serine, (FIG. 21B) methadone, (FIG. 21C) roxithromycin, and (FIG. 21D) bradykinin 2-9.

FIG. 5A shows MS spectrum of serine (concentration: 1 ppm, volume: 10 μl, solvent: MeOH/H$_2$O/HOAc (50:49:1, v/v/v)) using probes of the invention. FIG. 5B shows MS/MS spectrum of serine (concentration: 100 ppb, volume: 10 μl, solvent: MeOH/H$_2$O/HOAc (50:49:1, v/v/v)). Peak 74 and 83 also exist in the blank spectrum with solvent and without serine. FIG. 21A shows MS spectrum of serine (m/z, 106) using probes of the invention. FIG. 21A also shows MS/MS spectrum of serine (m/z, 106).

Figure 21B:
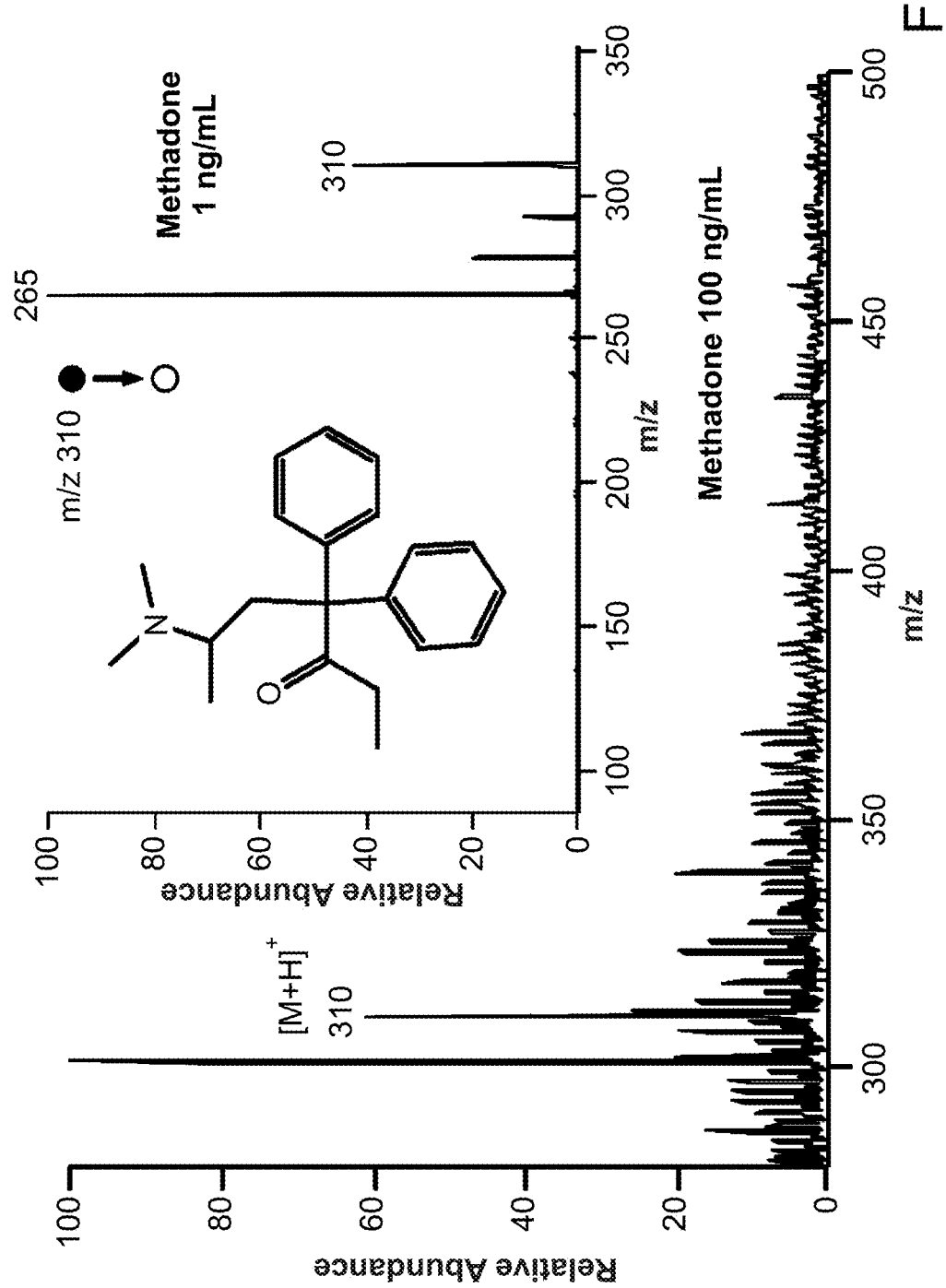
Figure 21C:
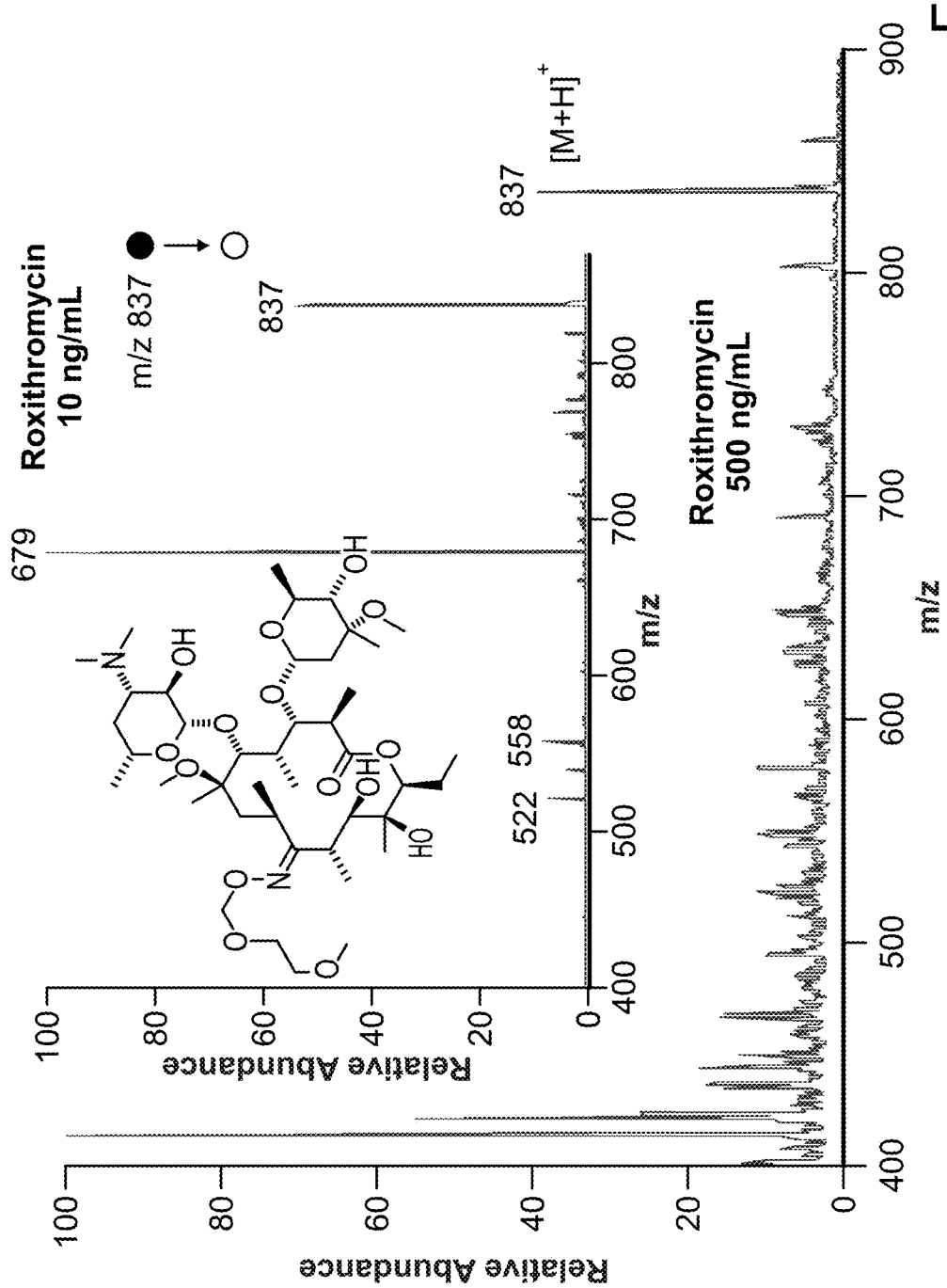

FIG. 21B shows MS spectrum of methadone (m/z, 310) using probes of the invention. FIG. 21B also shows MS/MS spectrum of methadone (m/z, 310). FIG. 21C shows MS spectrum of roxithromycin (m/z, 837) using probes of the invention. FIG. 21B also shows MS/MS spectrum of roxithromycin (m/z, 837).

Figure 6A:
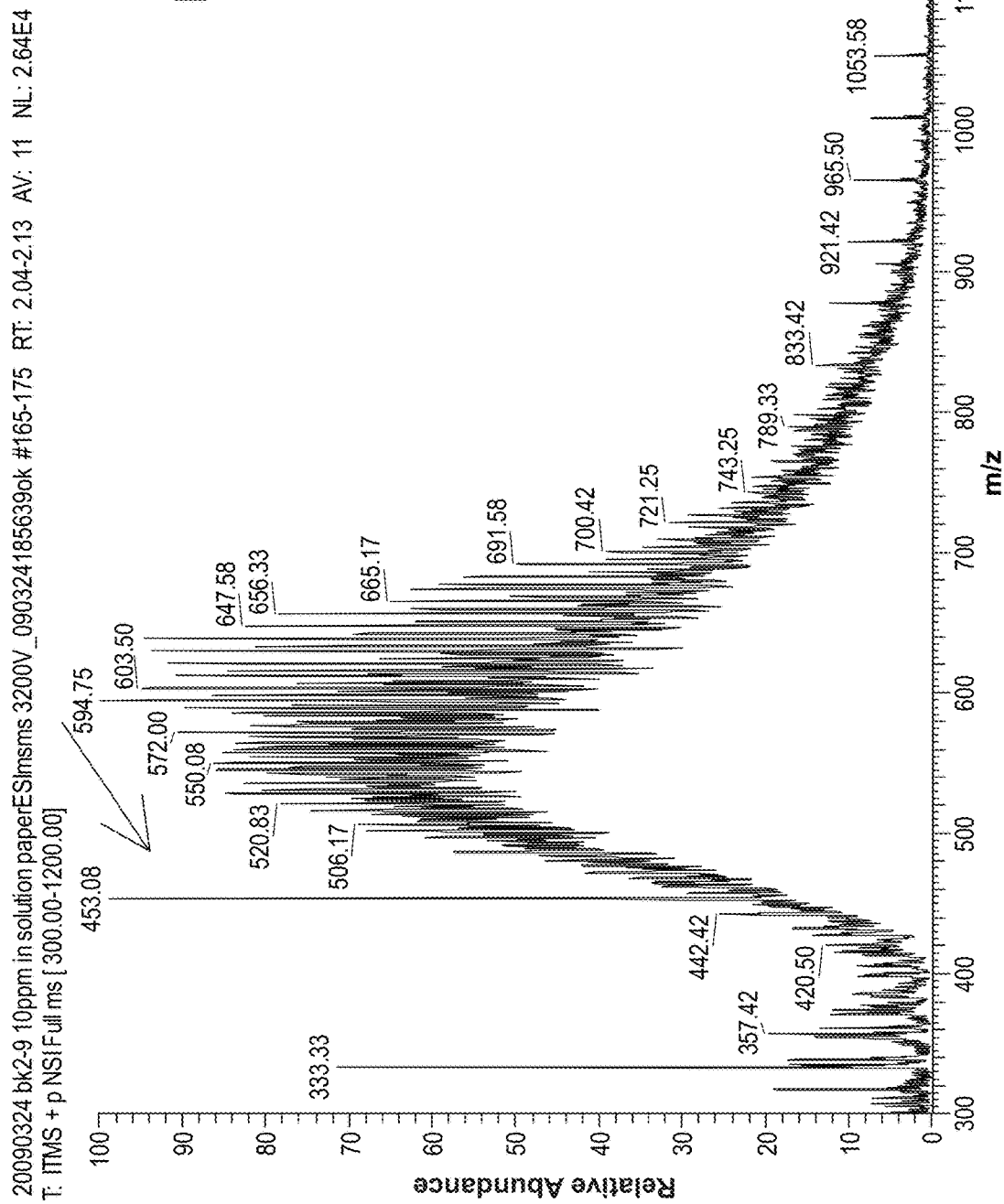
FIG. 6A is a MS spectrum of peptide bradykinin2-9 (concentration: 10 ppm, volume: 10 µl, solvent: MeOH/$H_2O$/HOAc (50:49:1, v/v/v)) using probes of the invention.
Figure 21D:
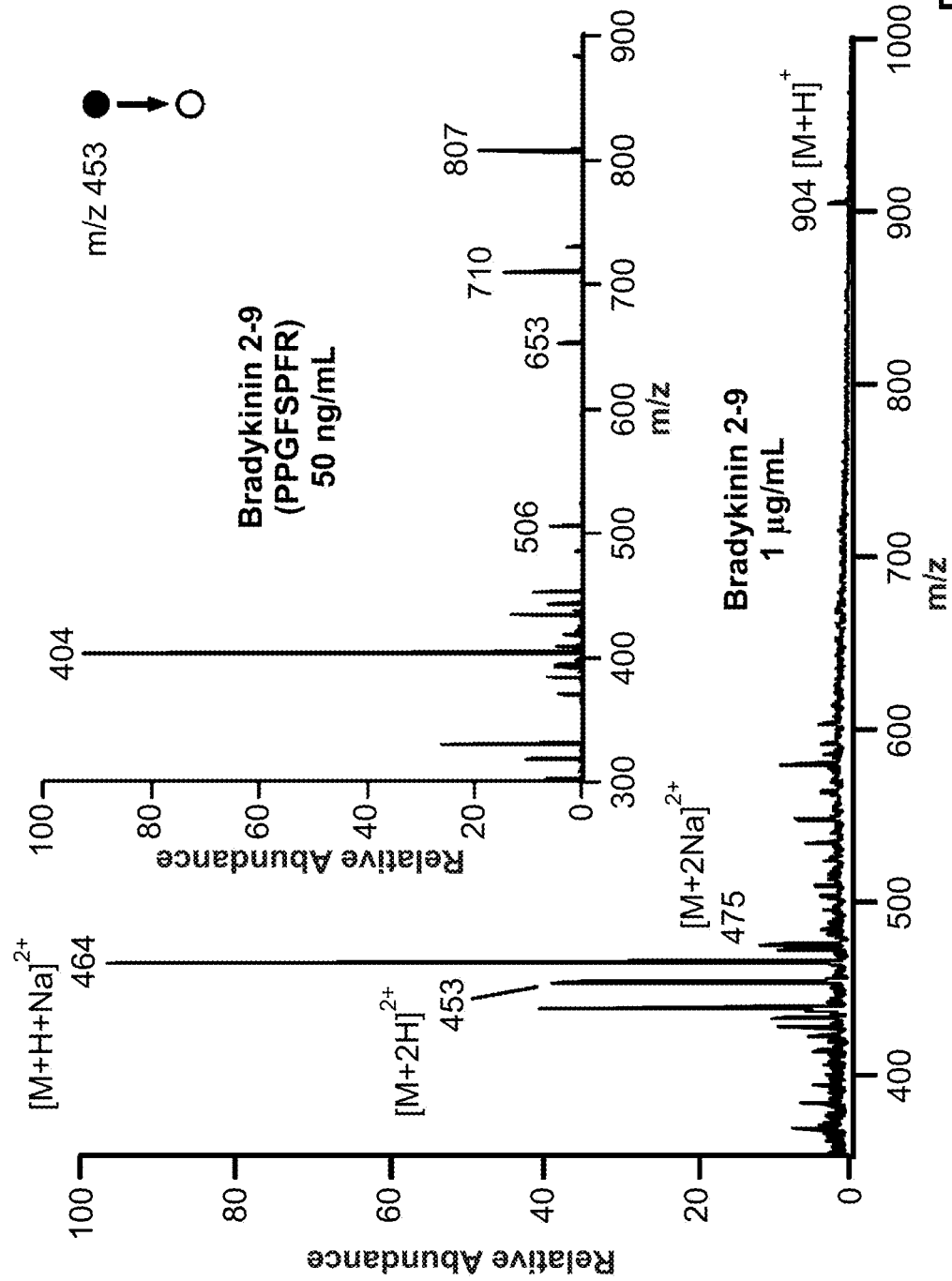

FIG. 6A shows MS spectrum of peptide bradykinin2-9 (concentration: 10 ppm, volume: 10 μl, solvent: MeOH/H$_2$O/HOAc (50:49:1, v/v/v)) using probes of the invention. FIG. 6B shows MS/MS spectrum of bradykinin2-9 (concentration: 1 ppm, volume: 10 μl, solvent: MeOH/H$_2$O/HOAc (50:49:1, v/v/v)). The hump in the spectrum is assumed to be caused by polymers, such as polyethylene glycol (PEG), which are frequently added to materials in industry. FIG. 21D shows MS spectrum of bradykinin 2-9 (m/z, 453) using probes of the invention. FIG. 21D also shows MS/MS spectrum of bradykinin 2-9 (m/z, 453). FIG. 21D further shows adduct ions [M+H] (m/z, 904), [M+2H]$^{2+}$ (m/z, 453), [M+H+Na]$^{2+}$ (m/z, 464) and [M+2Na]$^{2+}$ (m/z, 475). The m/z 453 peak was double charged adduct ion confirmed by the MS/MS spectrum.

Figure 11A:
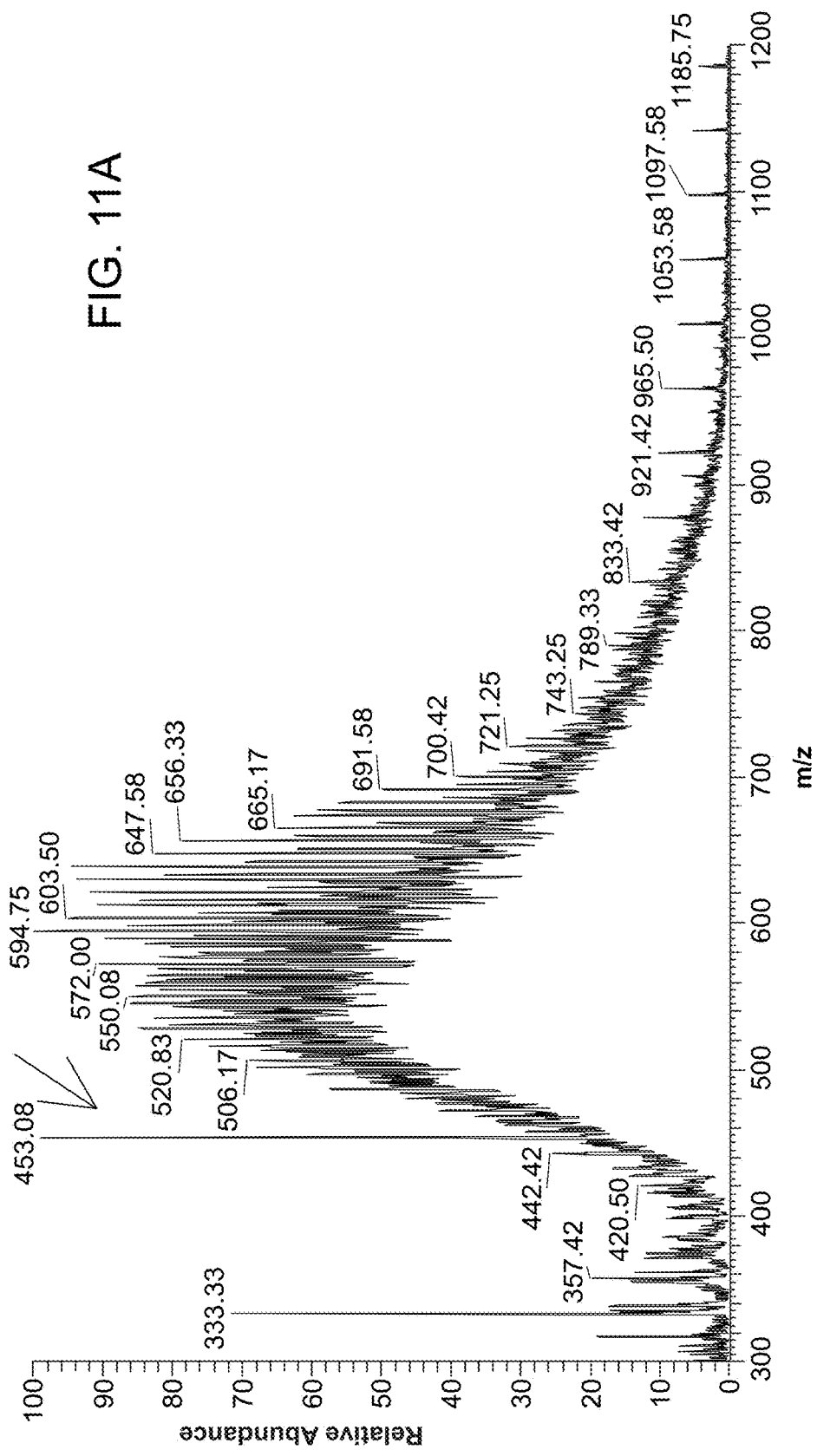
FIGS. 11A-B are MS spectra showing the difference between peptide analysis (10 ppm of bradykinin 2-9) on (FIG. 11A) paper triangle and (FIG. 11B) PVDF membrane using the same parameters (~2 kV, Solvent: MeOH:$H_2O$=1:1).
Figure 11B:
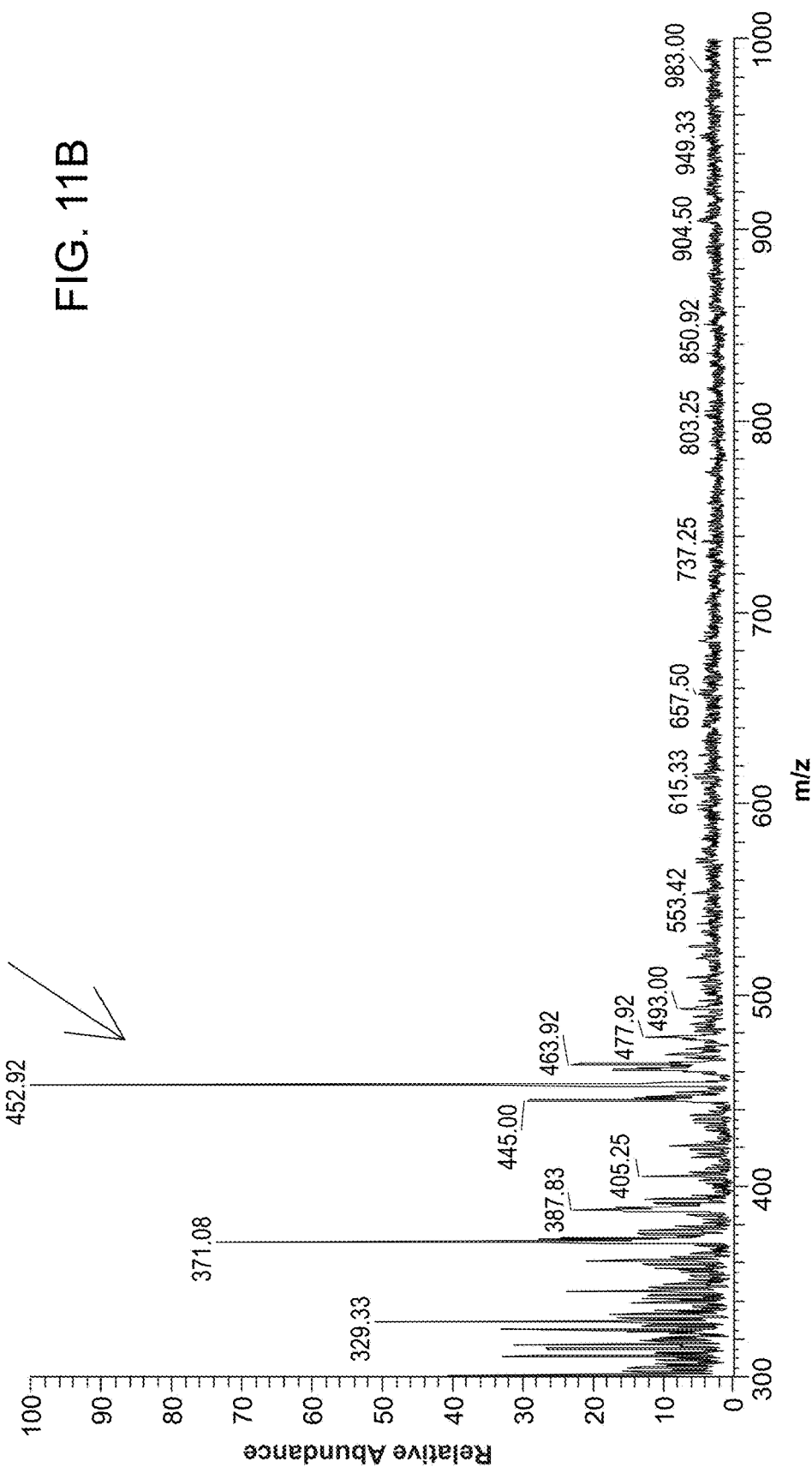

FIGS. 11A-B are MS spectra showing the difference between peptide analysis (10 ppm of bradykinin 2-9) on (FIG. 11A) paper slice and (FIG. 11B) PVDF membrane using the same parameters (~2 kV, Solvent: MeOH:H$_2$O=1:1).

Data herein show that probes of the invention work well over the mass/charge range from 50 to over 1000 for detection of pure compounds. Data further shows that detection was achieved down to as low as 1 ng/mL for most chemicals, including illegal drugs, such as heroin, cocaine and methadone.

Example 7: Complex Mixtures

Complex mixtures such as urine, blood, and cola drink were examined using methods, devices, and systems of the invention. All experiments were carried out with a Finnigan LTQ mass spectrometer (Thermo Electron, San Jose, Calif.).

Figure 7A:
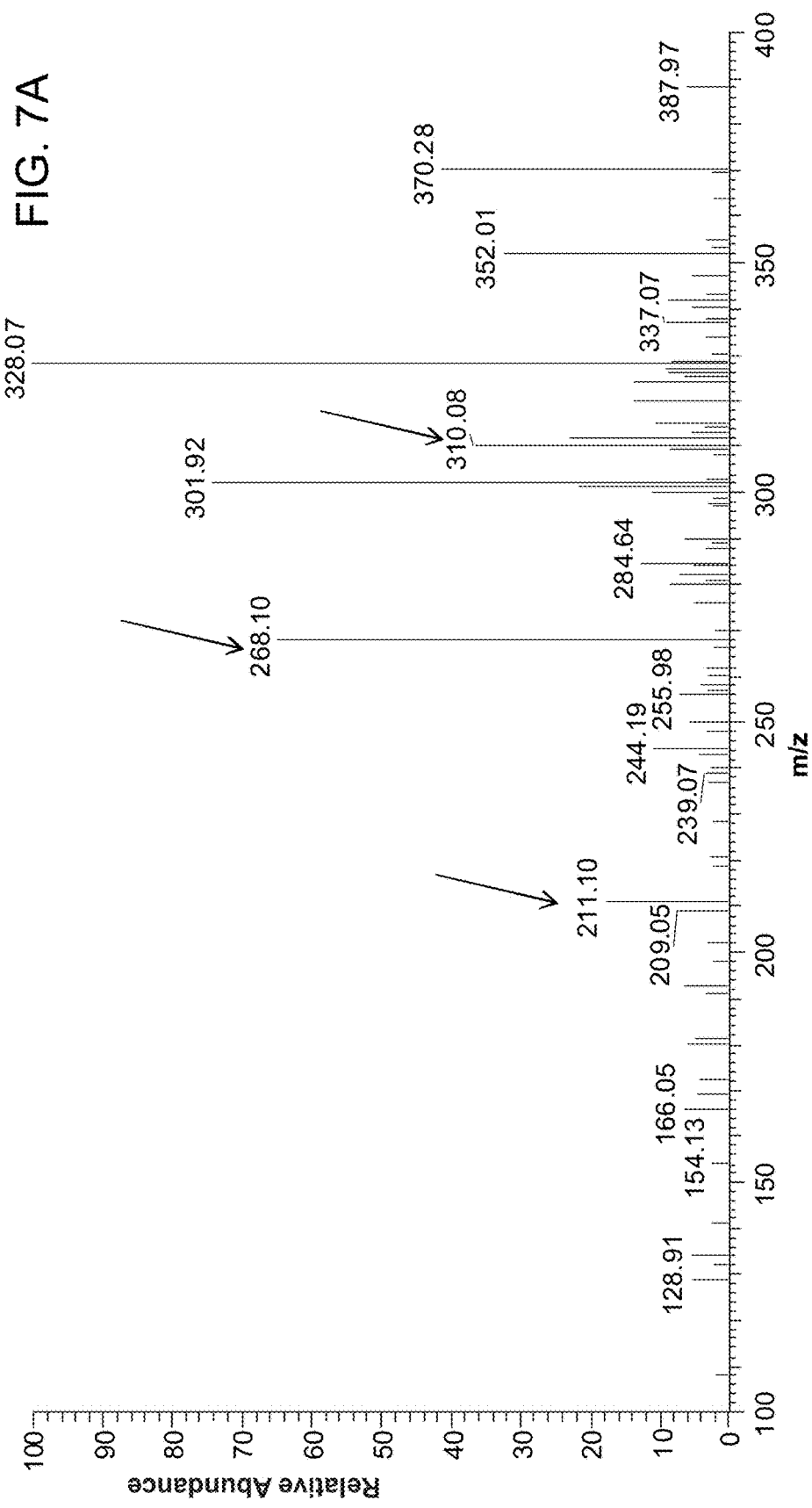
FIG. 7A is a MS/MS spectrum showing that heroin can be detected from whole blood sample by a "spot" method.

FIG. 7A shows an MS/MS spectrum that shows that heroin was detected from whole blood sample by a "spot" method. 0.4 μl of whole blood sample containing 200 ppb heroin was applied on the center of the triangle paper to form a 1 mm$^2$ blood spot. After the spot was dry, 10 μl of solvent (MeOH/H$_2$O/HOAc (50:49:1, v/v/v)) was applied to the rear end of the triangle paper. Due to the capillary effect, the solvent moved forward and dissolved the chemicals in the blood spot. Finally, electrospray occurred when the solvent reached the tip of the paper. To demonstrate the effectiveness of the "blood spot" method mentioned above, the whole blood was added on the paper for electrospray directly. MS/MS spectrum showed that heroin was not detected from 10 μl of whole blood sample, even when the concentration was as high as 20 ppm (FIG. 7B).

Figure 8A:
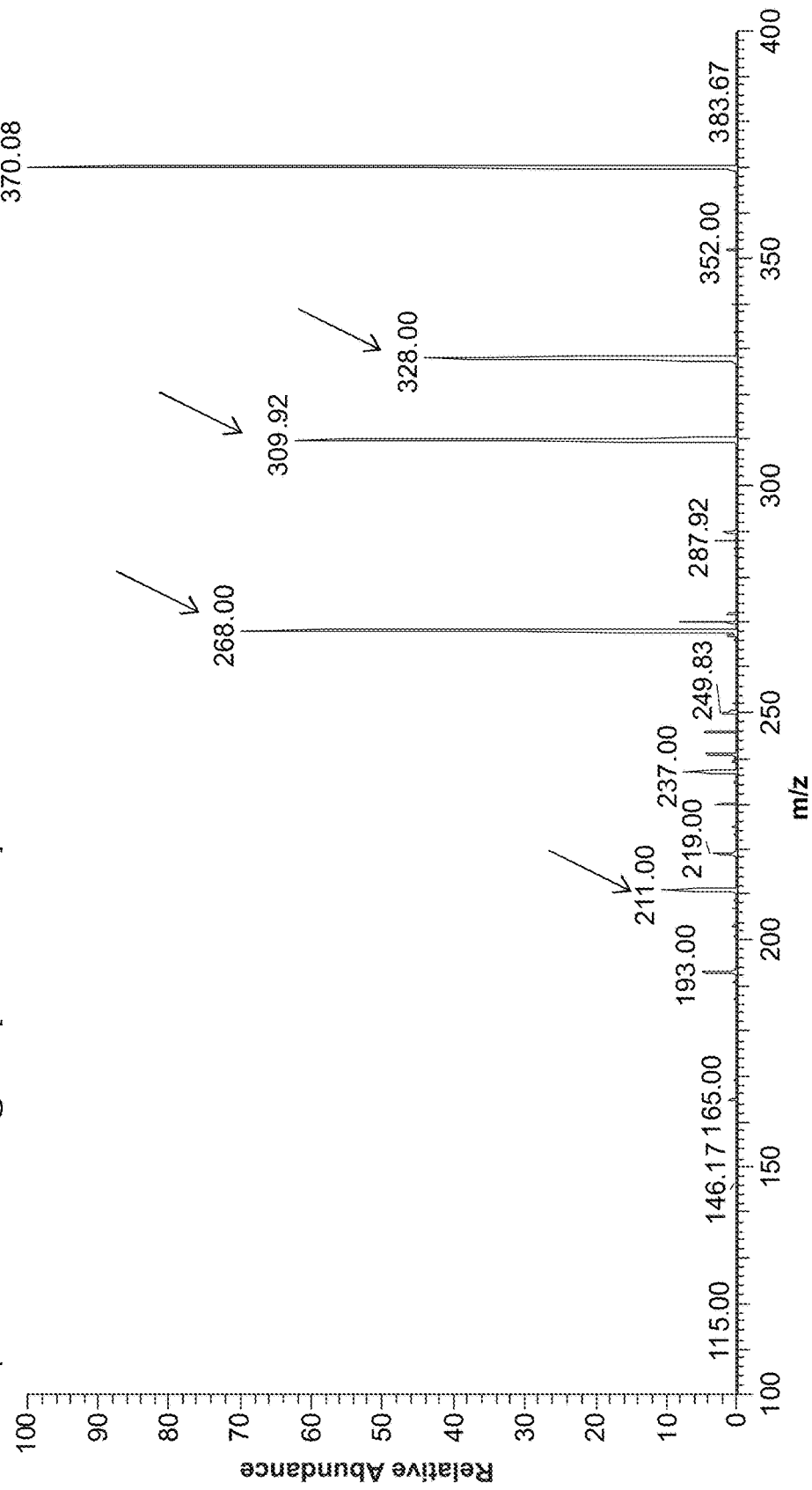
FIG. 8A MS/MS spectrum shows heroin can be detected from raw urine sample by a "spot" method.
Figure 8B:
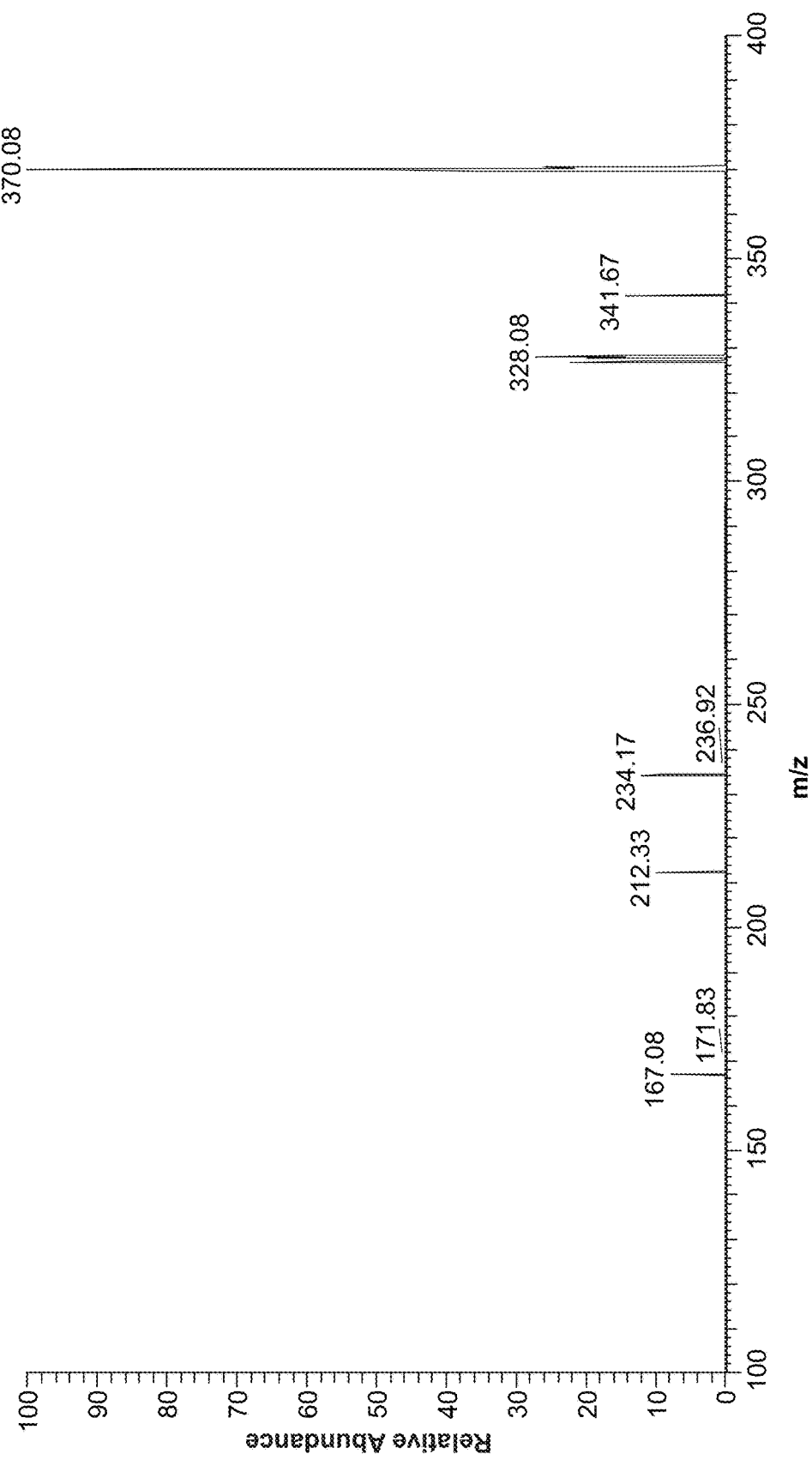
FIG. 8B shows the MS/MS spectrum of the urine spot without heroin.

FIG. 8A shows an MS/MS spectrum that shows that heroin can be detected from raw urine sample by a "spot" method. 0.4 μl of raw urine sample containing 100 ppb heroin was applied on the center of the triangle paper to form a 1 mm$^2$ urine spot. After the spot was dry, 10 μl of solvent (MeOH/H$_2$O/HOAc (50:49:1, v/v/v)) was applied to the rear end of the triangle paper. Due to the capillary effect, the solvent moved forward and dissolved the chemicals in the blood spot. Finally, electrospray occurred when the solvent reached the tip of the paper. To demonstrate the effectiveness of the "spot" method mentioned above, the raw urine was added on the paper for electrospray directly. MS/MS spectrum showed heroin was not detected from 10 μl of raw urine sample when concentration was 100 ppb (FIG. 8B).

Figure 9A:
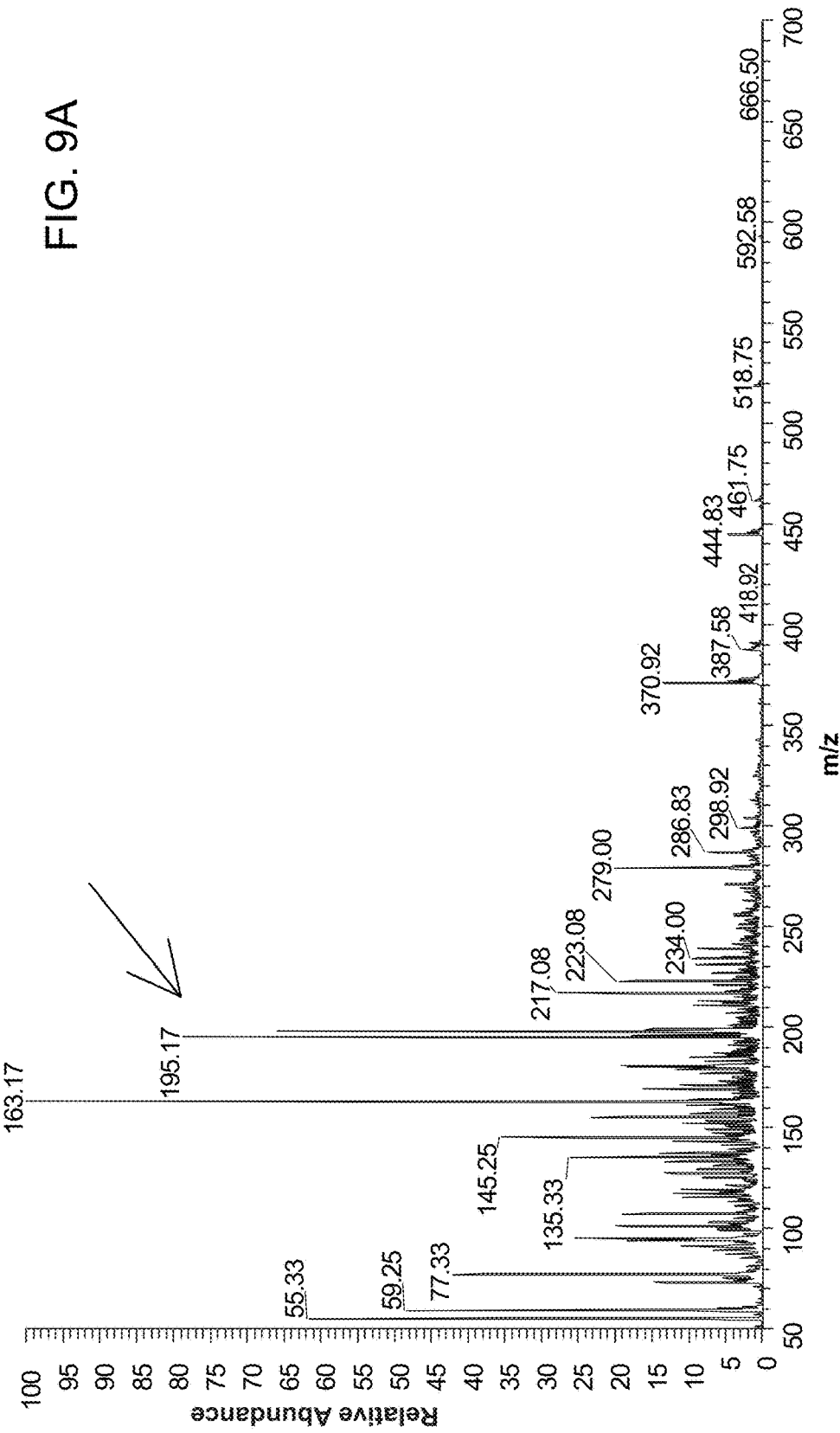
FIG. 9A is a MS spectrum showing the caffeine detected from a cola drink without sample preparation.
Figure 9B:
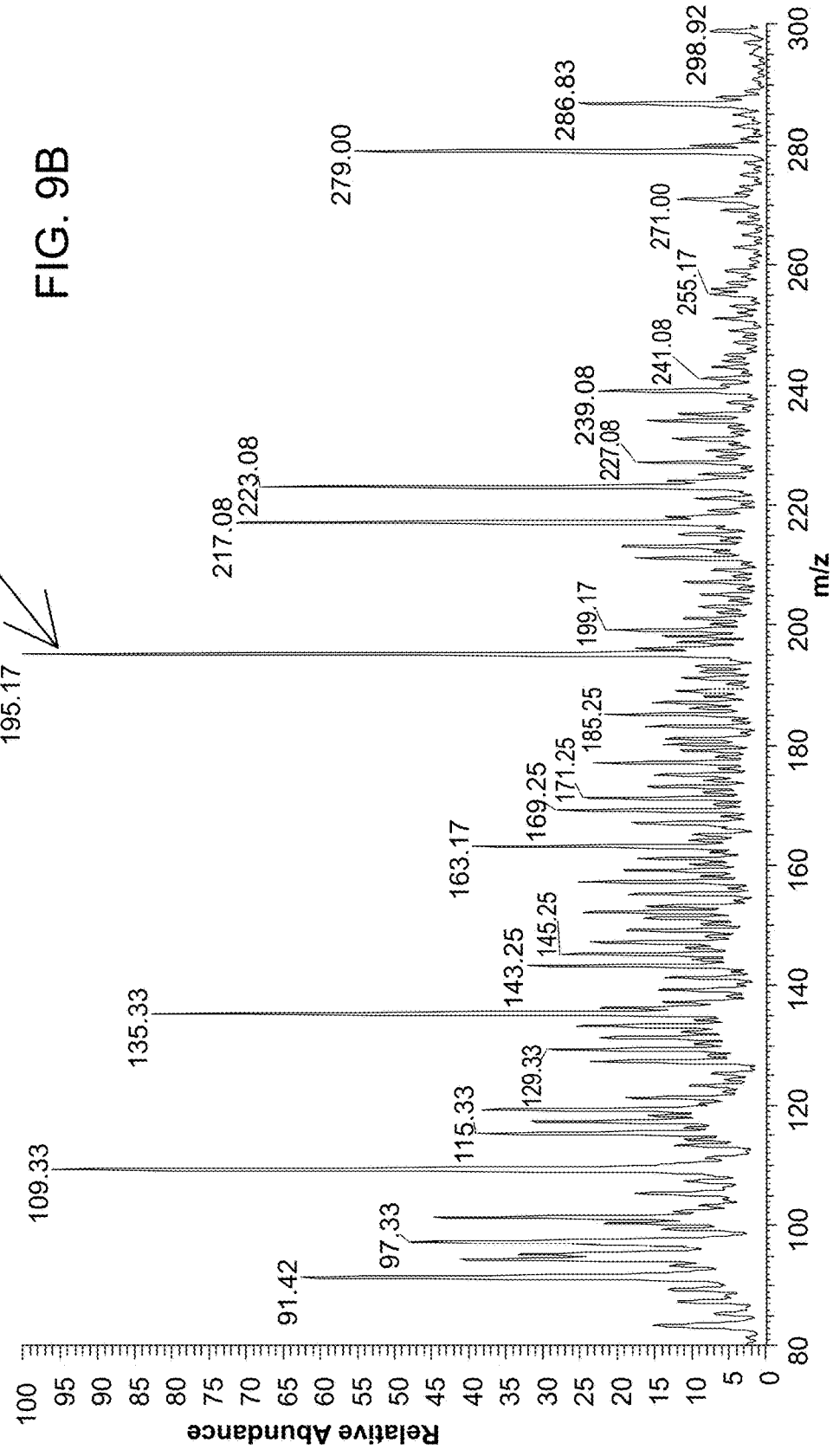
FIG. 9B is a MS spectrum showing caffeine detected from coffee powder. A paper slice was used to collect the coffee powder from a coffee bag by swabbing the surface.

FIG. 9A is an MS spectrum showing that caffeine was detected from a cola drink without sample preparation. FIG. 9B is an MS spectrum showing that caffeine was detected from coffee powder. A paper triangle was used to collect the coffee powder from a coffee bag by swabbing the surface.

Figure 22A:
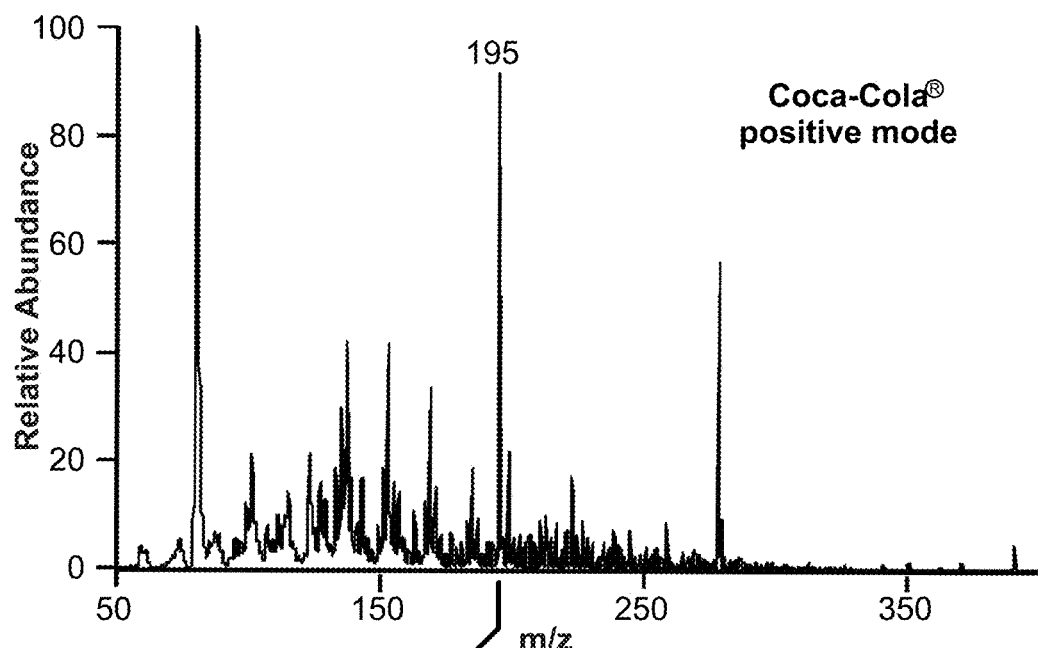
FIGS. 22A-G are a set of mass spectra showing analysis of chemicals from complex mixtures and direct analysis from surfaces without sample preparation.
Figure 22C:
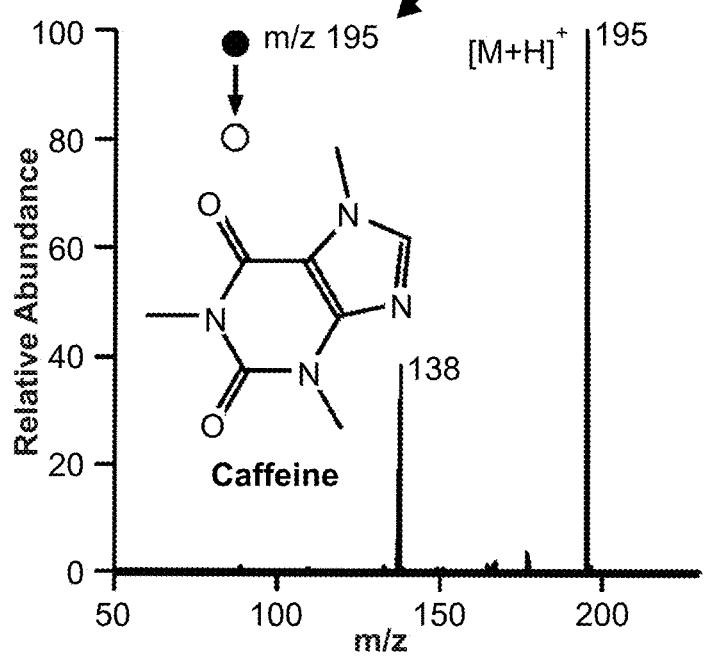
Figure 22B:
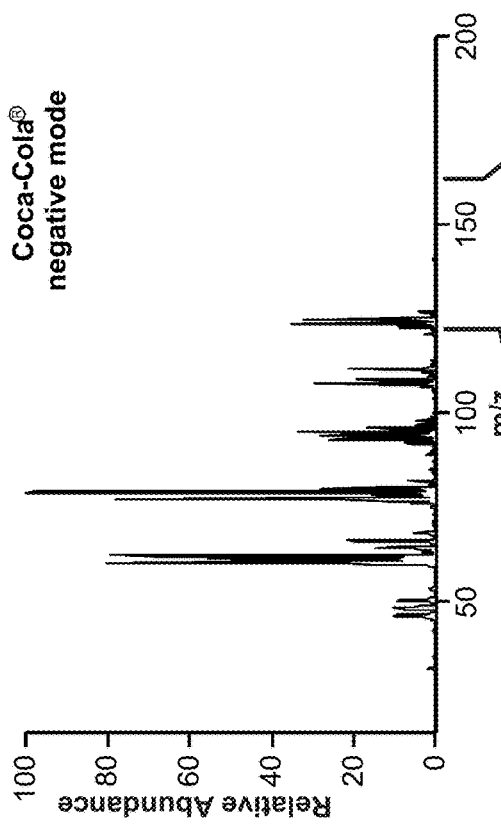
Figure 22E:
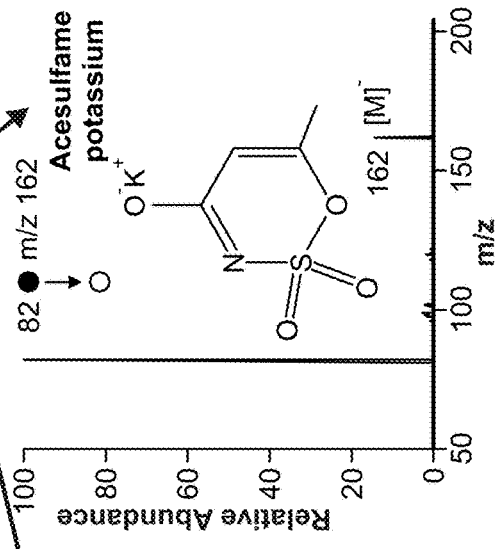
Figure 22D:
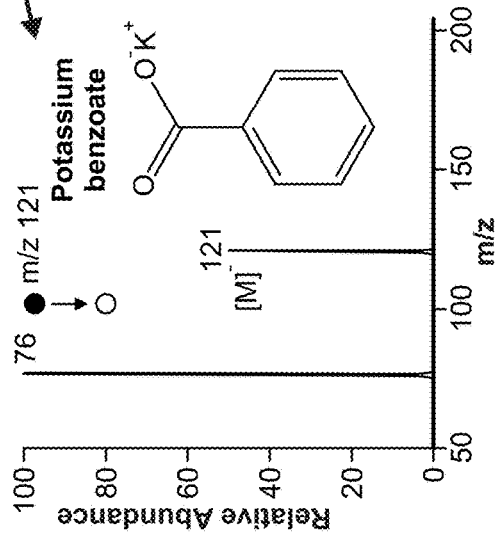

FIGS. 22A-B show the spectra of COCA-COLA (cola drink), analyzed in positive mode and negative mode, respectively. The peak of protonated caffeine, m/z 195, identified in MS/MS spectrum, was dominated in the mass spectrum in positive mode due to the high concentration of caffeine (100 ug/mL) in this drink (FIG. 22C). Two high concentrated compounds, potassium benzoate and acesulfame potassium were identified in the MS/MS spectrum in negative mode (FIGS. 22D-E).

Figure 22F:
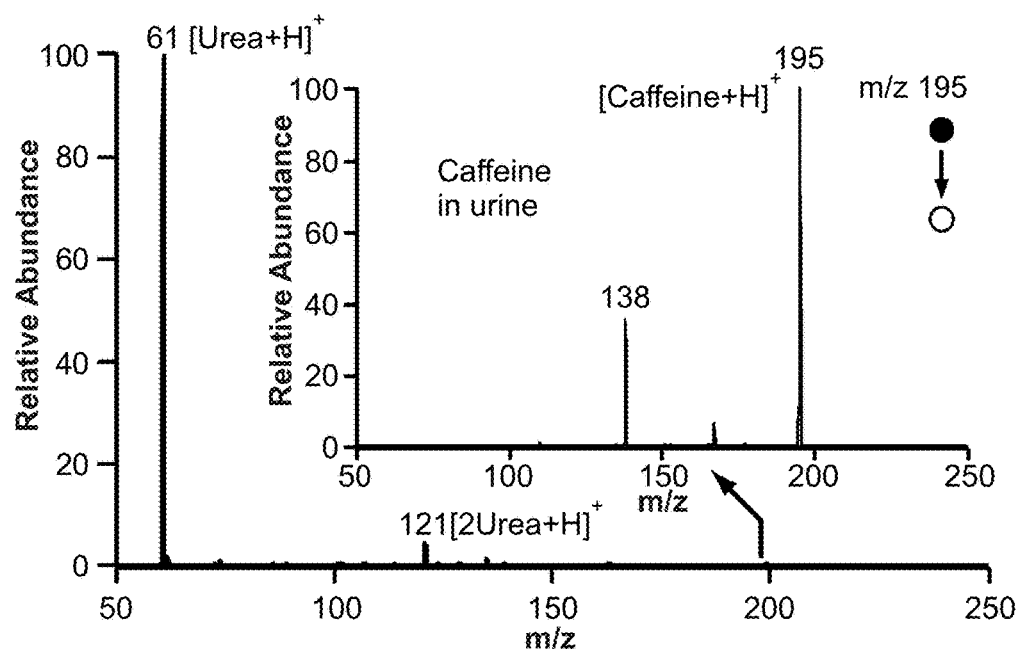

FIG. 22F shows spectra of caffeine in urine from a person who had drunk COCA-COLA (cola drink) two hours before the urine collection. Urine typically contains urea in very high concentration, which is also easily ionized. Therefore, protonated urea [m/z, 61] and urea dimmer [m/z, 121] dominated the MS spectrum. However, the protonated caffeine was identified in the MS/MS spectrum, which showed good signal to noise ratio in the urine sample.

Figure 10A:
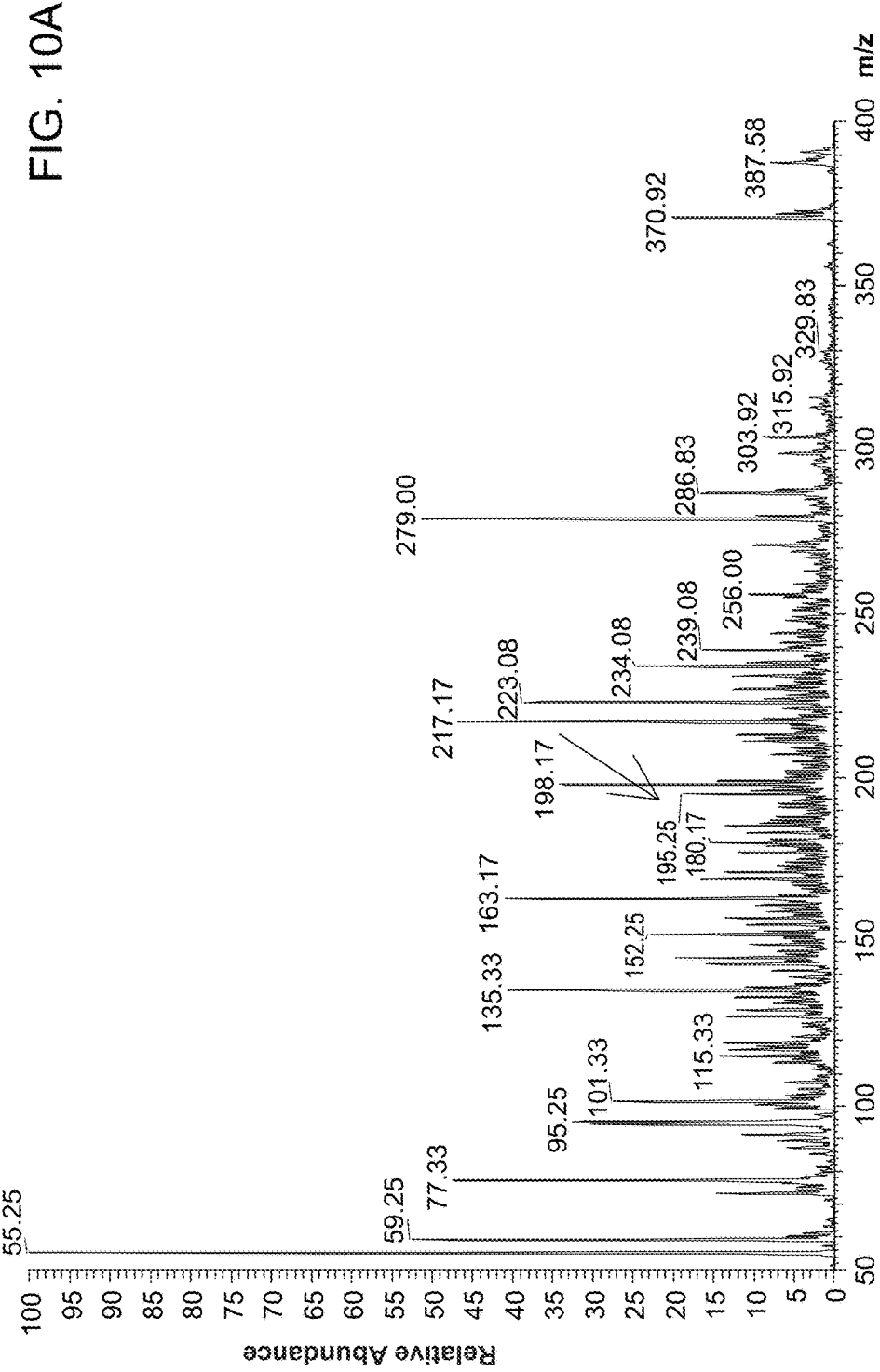
FIGS. 10A-B show MS spectra of urine analysis without sample preparation.
Figure 10B:
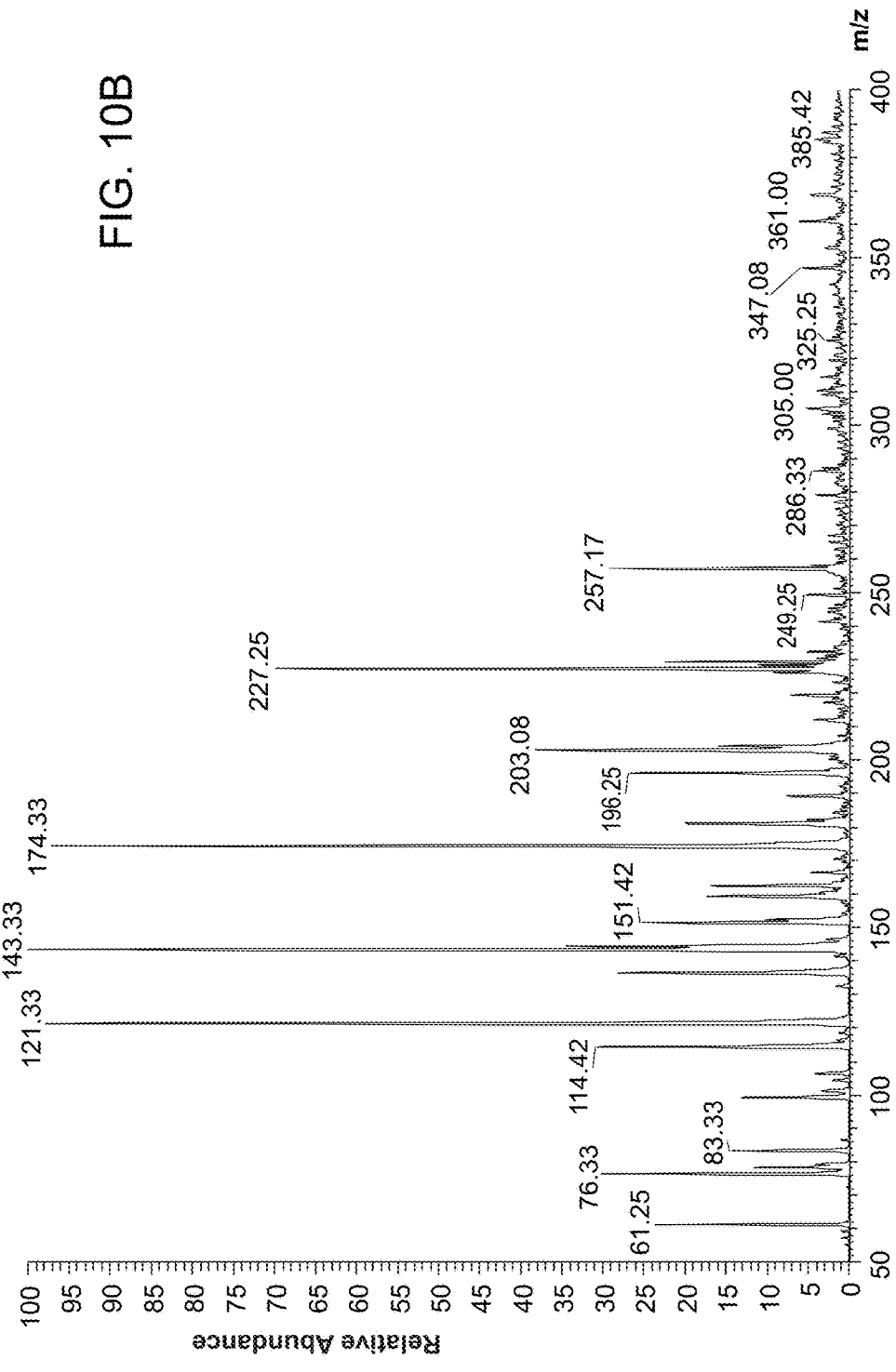

FIGS. 10A-B show MS spectra of urine taken for analysis without sample preparation. FIG. 10A is a mass spectra of caffeine that was detected in urine from a person who had consumed coffee. FIG. 10B is a mass spectra showing that caffeine was not detected in urine from a person who had not consumed any coffee.

Figure 22G:
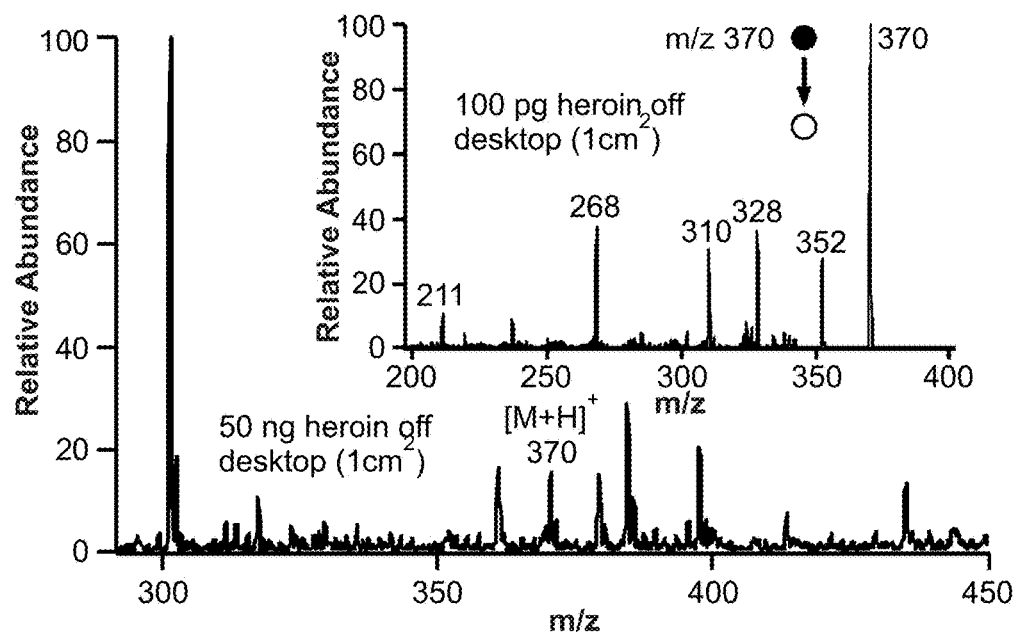

FIG. 22G shows the MS spectrum of heroin (m/z, 370) collected as a swabbed sample. A 5 uL solution containing 50 ng heroin was spotted on a 1 cm$^2$ area of a desktop. The paper triangle was wetted and used to swab the surface of the desktop. The paper triangle was then connected to the high voltage source for mass detection. This data shows that probes of the invention can have dual roles of ionization source as well as a sampling device for mass detection. Trace sample on solid surface could be simply collected by swabbing the surface using probes of the invention. Dust and other interferences were also collected on the paper triangle, but the heroin could be directly detected from this complex matrix.

Example 8: Plant Tissue Direct Analysis by ESI without Extraction

Figure 12A:
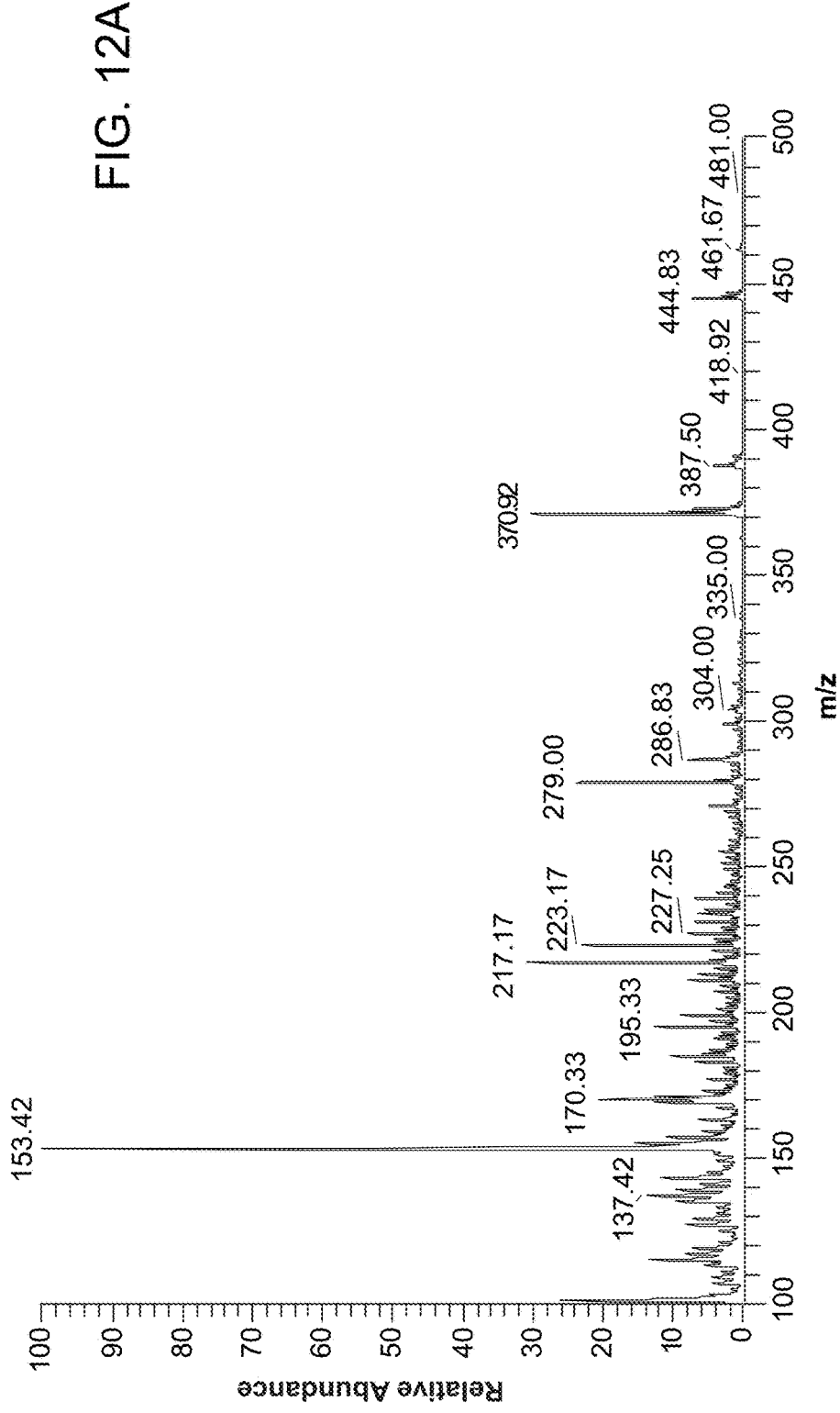
Figure 12C:
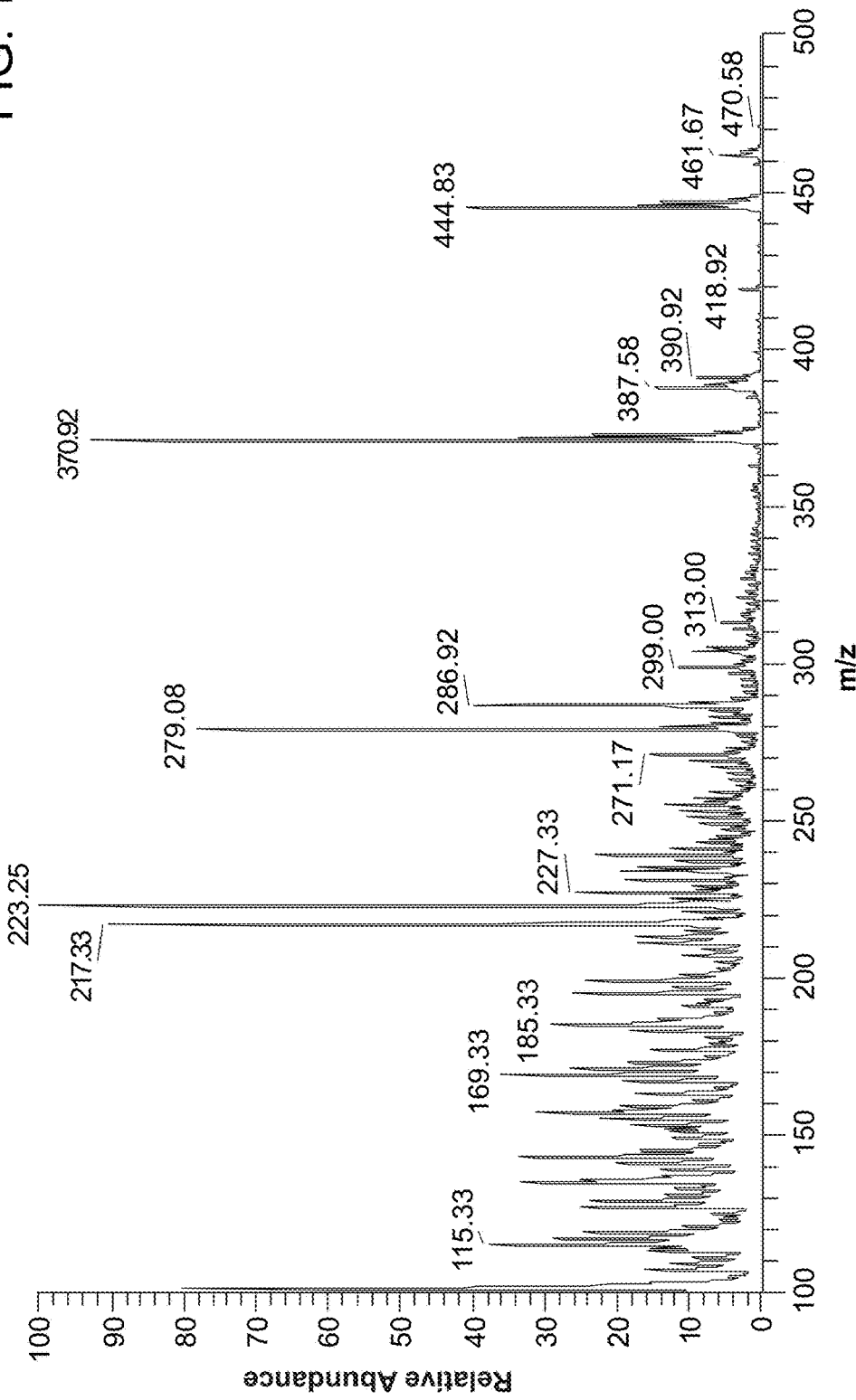
Figure 12D:
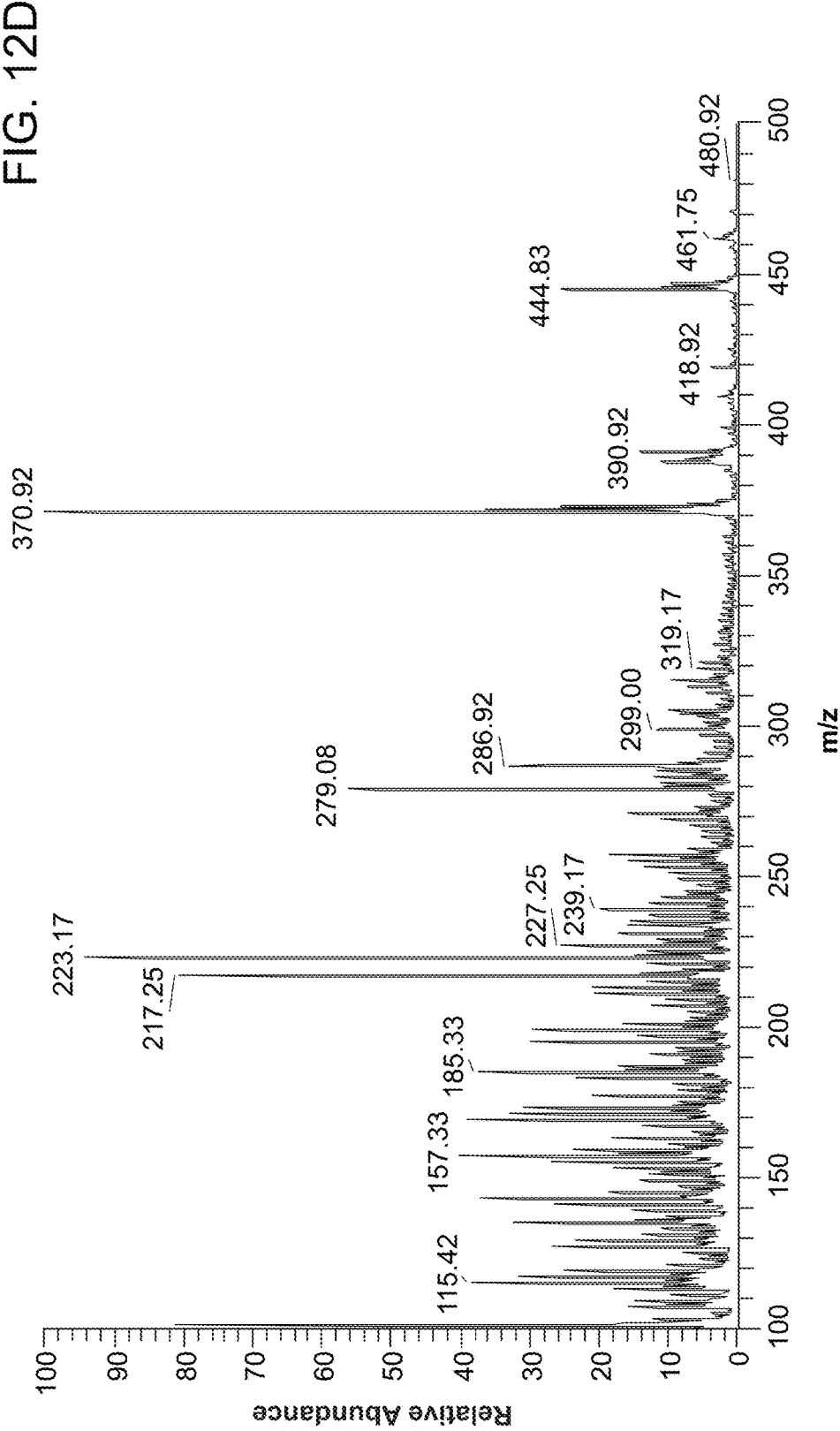

FIGS. 12A-D shows direct MS spectra of plant tissues using sliced tissues of four kinds of plants. (FIG. 12A) Onion, (FIG. 12B) Spring onion, and two different leaves (FIG. 12C) and (FIG. 12D).

Figure 13A:
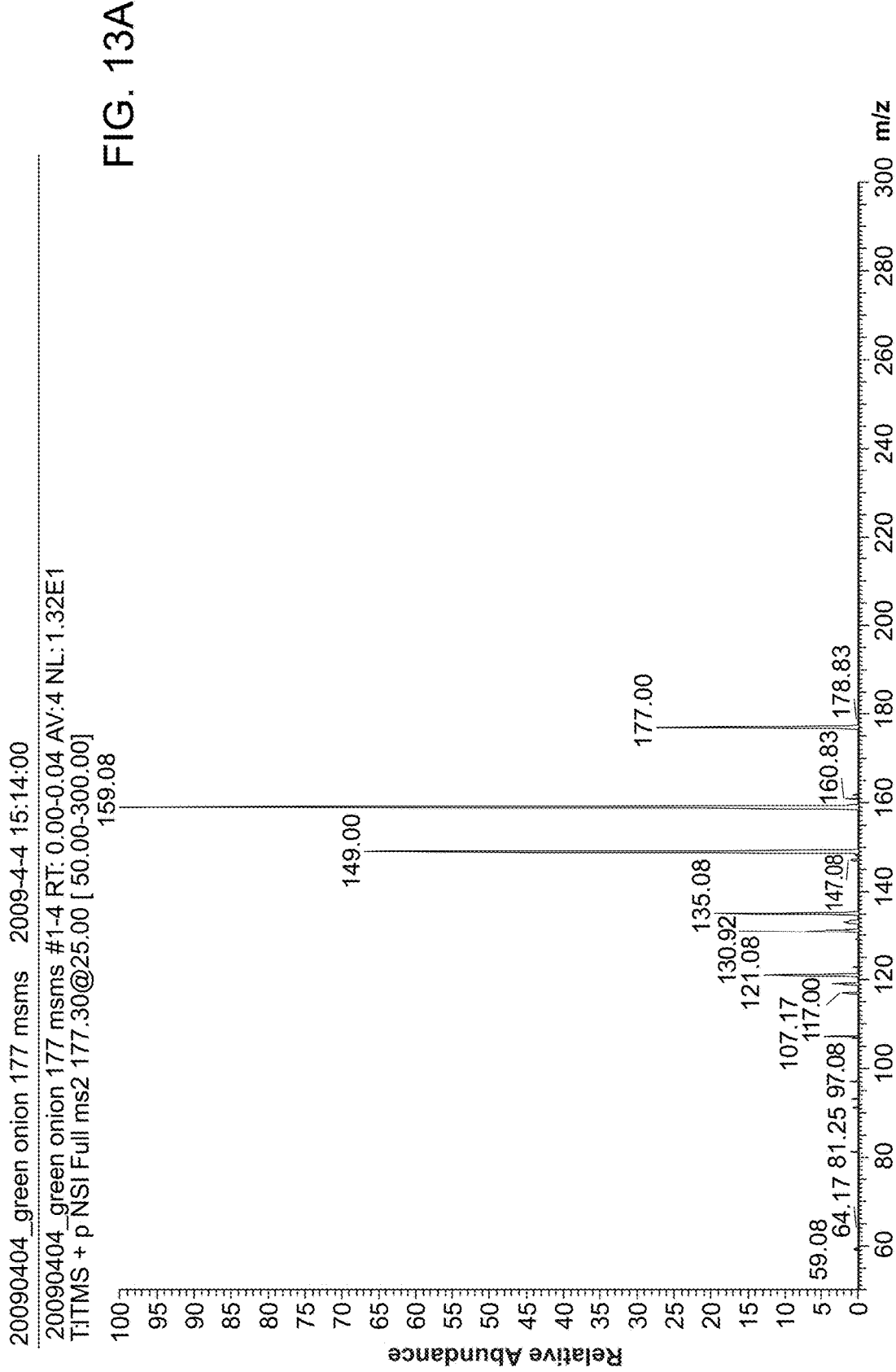
FIGS. 13A-B show MS/MS spectra of Vitamin C.
Figure 13B:
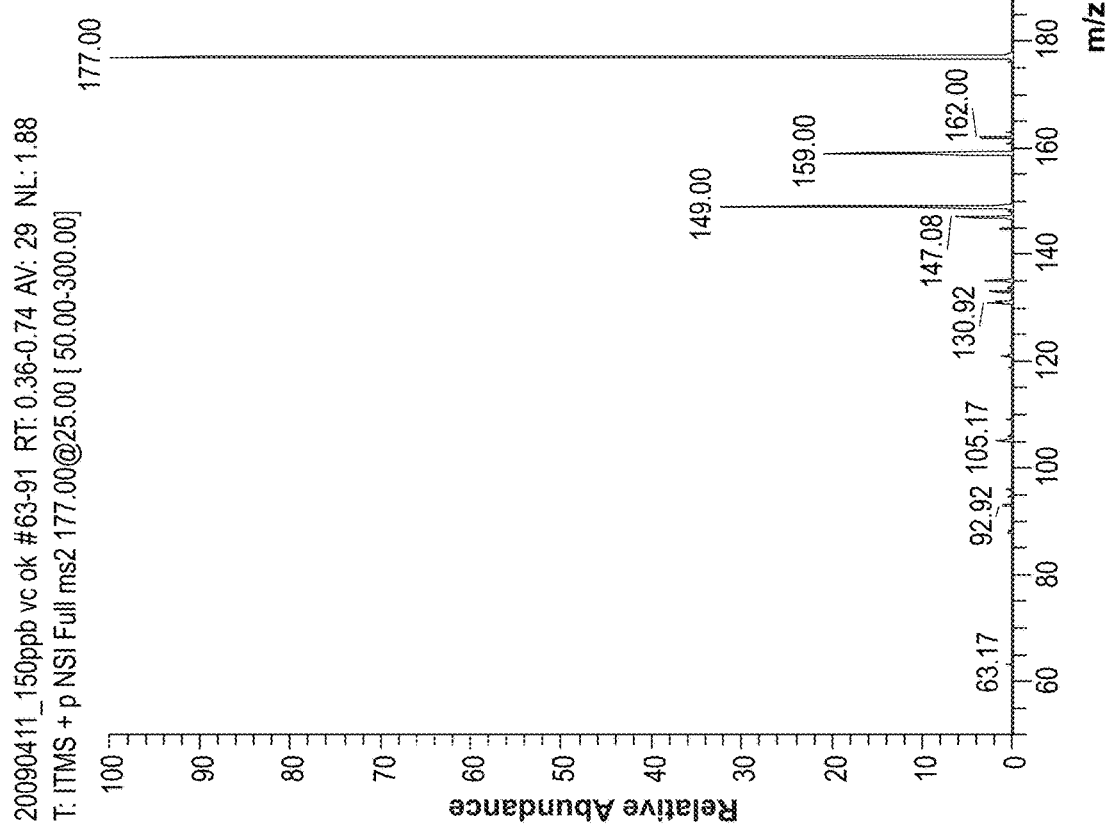

FIGS. 13A-B shows an MS/MS spectra of Vitamin C analysis (FIG. 13A) direct analysis of onion without sample preparation, (FIG. 13B) using standard solution.

Example 9: Whole Blood and Other Biofluids

Body fluids, such as plasma, lymph, tears, saliva, and urine, are complex mixtures containing molecules with a wide range of molecular weights, polarities, chemical properties, and concentrations. Monitoring particular chemical components of body fluids is important in a number of different areas, including clinical diagnosis, drug development, forensic toxicology, drugs of abuse detection, and therapeutic drug monitoring. Tests of blood, including the derived fluids plasma and serum, as well as on urine are particularly important in clinical monitoring.

A wide variety of chemicals from blood are routinely monitored in a clinical setting. Common examples include a basic metabolic panel measuring electrolytes like sodium and potassium along with urea, glucose, and creatine and a lipid panel for identifying individuals at risk for cardiovascular disease that includes measurements of total cholesterol, high density lipoprotein (HDL), low density lipoprotein (LDL), and triglycerides. Most laboratory tests for chemicals in blood are actually carried out on serum, which is the liquid component of blood separated from blood cells using centrifugation. This step is necessary because many medical diagnostic tests rely on colorimetric assays and therefore require optically clear fluids. After centrifugation, detection of the molecule of interest is carried in a number of ways, most commonly by an immunoassay, such as an enzyme-linked immunosorbent assay (ELISA) or radioimmunoas say (RIA), or an enzyme assay in which the oxidation of the molecule of interest by a selective enzyme is coupled to a reaction with a color change, such as the tests for cholesterol (oxidation by cholesterol oxidase) or glucose (oxidation by glucose oxidase).

There is considerable interest in the pharmaceutical sciences in the storage and transportation of samples of whole blood as dried blood spots on paper (N. Spooner et al. *Anal Chem.*, 2009, 81, 1557). Most tests for chemicals found in blood are carried out on a liquid sample, typically serum or plasma isolated from the liquid whole blood. The required storage, transportation, and handling of liquid blood or blood components present some challenges. While blood in liquid form is essential for some tests, others can be performed on blood or other body fluids that have been spotted onto a surface (typically paper) and allowed to dry.

Probes and methods of the invention can analyze whole blood without the need for any sample preparation. The sample was prepared as follows. 0.4 uL blood was directly applied on the center of paper triangle and left to dry for about 1 min. to form a dried blood spot (FIG. 23A). 10 uL methanol/water (1:1, v/v) was applied near the rear end of the paper triangle. Driven by capillary action, the solution traveled across the paper wetting it throughout its depth. As the solution interacted with the dried blood spot, the analytes from the blood entered the solution and were transported to the tip of the probe for ionization (FIG. 23A). The process of blood sample analysis was accomplished in about 2 min.

Different drugs were spiked into whole blood and the blood was applied to probes of the invention as described above. Detection of different drugs is described below.

Figure 14C:
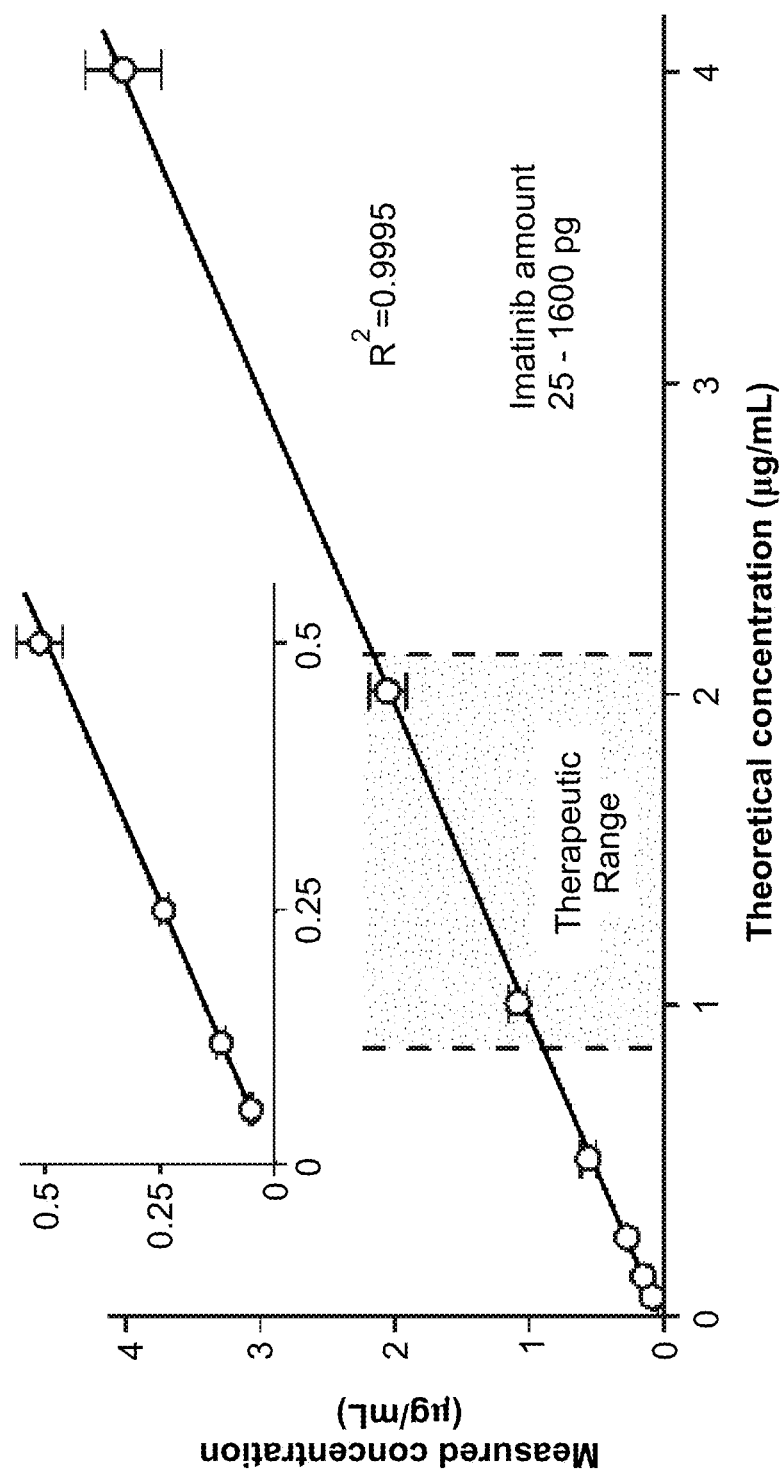
FIG. 14C shows a quantitative analysis of whole blood spiked with imatinib (62.5-4 µg/mL) and its isotopomers imatinib-d8 (1 µg/mL). Inset plot shows low concentration range.

Imatinib (GLEEVEC), a 2-phenylaminopyrimidine derivative, approved by the FDA for treatment of chronic myelogenous leukemia, is efficacious over a rather narrow range of concentrations. Whole human blood, spiked with imatinib at concentrations including the therapeutic range, was deposited on a small paper triangle for analysis (FIG. 14A). The tandem mass spectrum (MS/MS, FIG. 14B) of protonated imatinib, m/z 494, showed a single characteristic fragment ion. Quantitation of imatinib in whole blood was achieved using this signal and that for a known concentration of imatinib-d8 added as internal standard. The relative response was linear across a wide range of concentrations, including the entire therapeutic range (FIG. 14C).

Figure 23B:
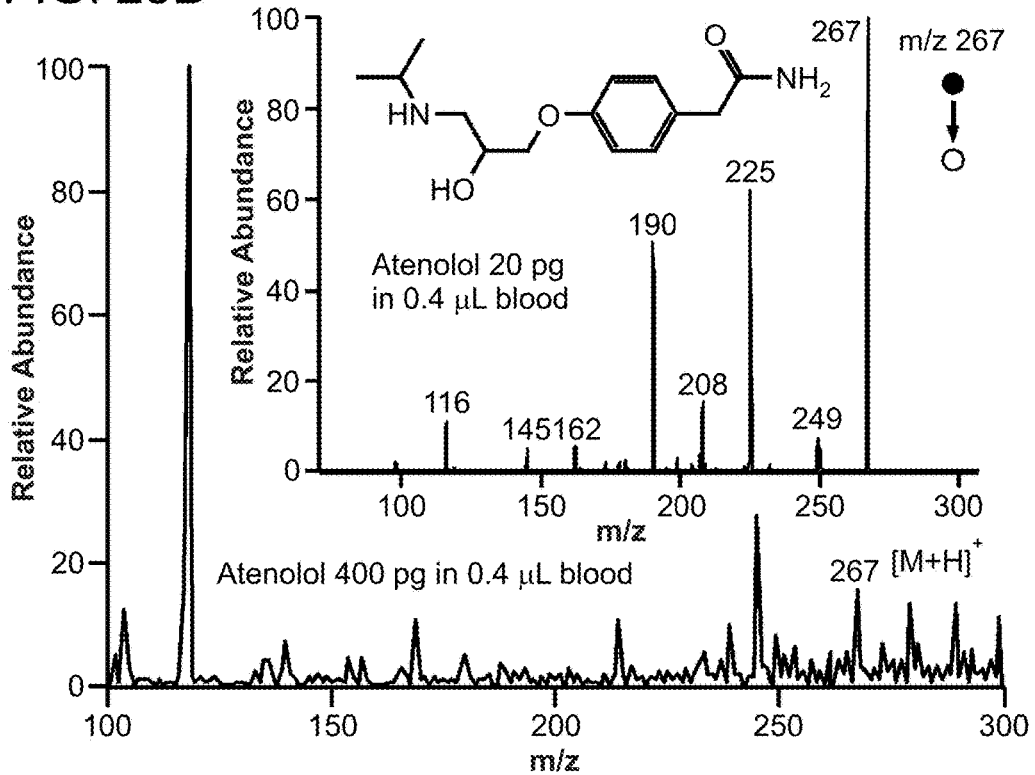
FIG. 23B is a mass spectrum of Atenolol from whole blood.

Atenolol, a β-blocker drug used in cardiovascular diseases, was tested using the dried blood spot method to evaluate paper spray for whole blood analysis. Atenolol was directly spiked into whole blood at desired concentrations and the blood sample was used as described above for paper spray. The protonated atenolol of 400 pg (1 ug/mL atenolol in 0.4 uL whole blood) in dried blood spot was shown in mass spectra, and the MS/MS spectra indicated that even 20 pg of atenolol (50 ug/mL atenolol in 0.4 uL whole blood) could be identified in the dried blood spot (FIG. 23B).

Figure 23C:
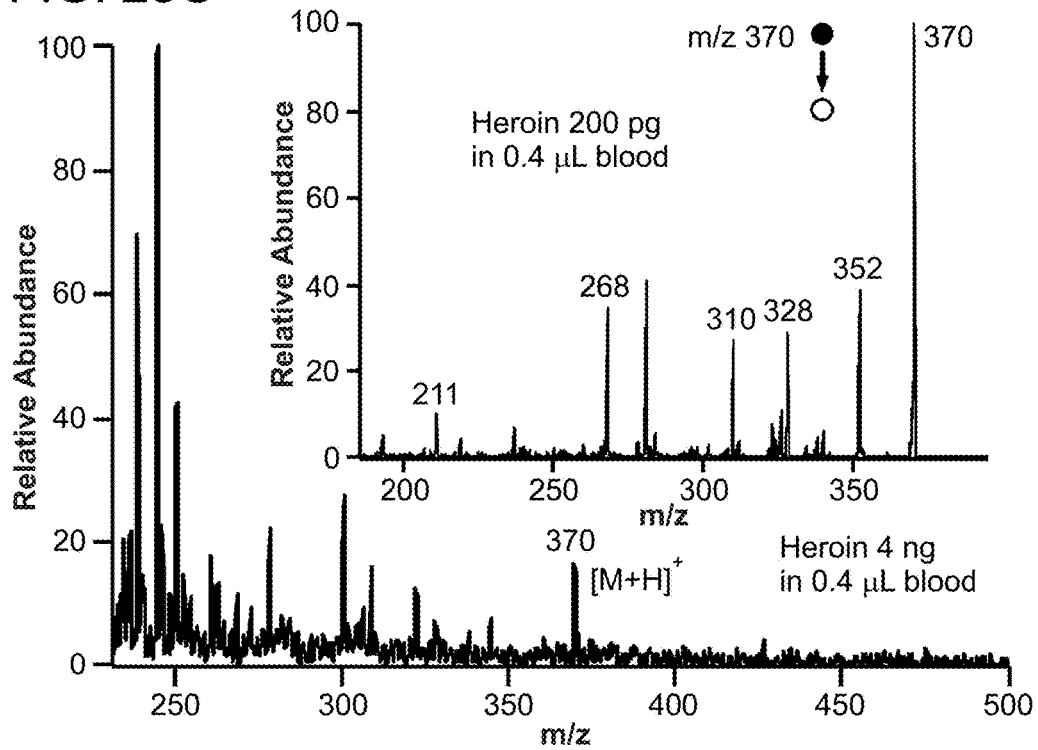
FIG. 23C is a mass spectrum of heroin from whole blood.

FIG. 23C is a mass spectra of heroin in whole blood. Data herein show that 200 pg heroin in dried blood spot could be detected using tandem mass.

Figure 18:
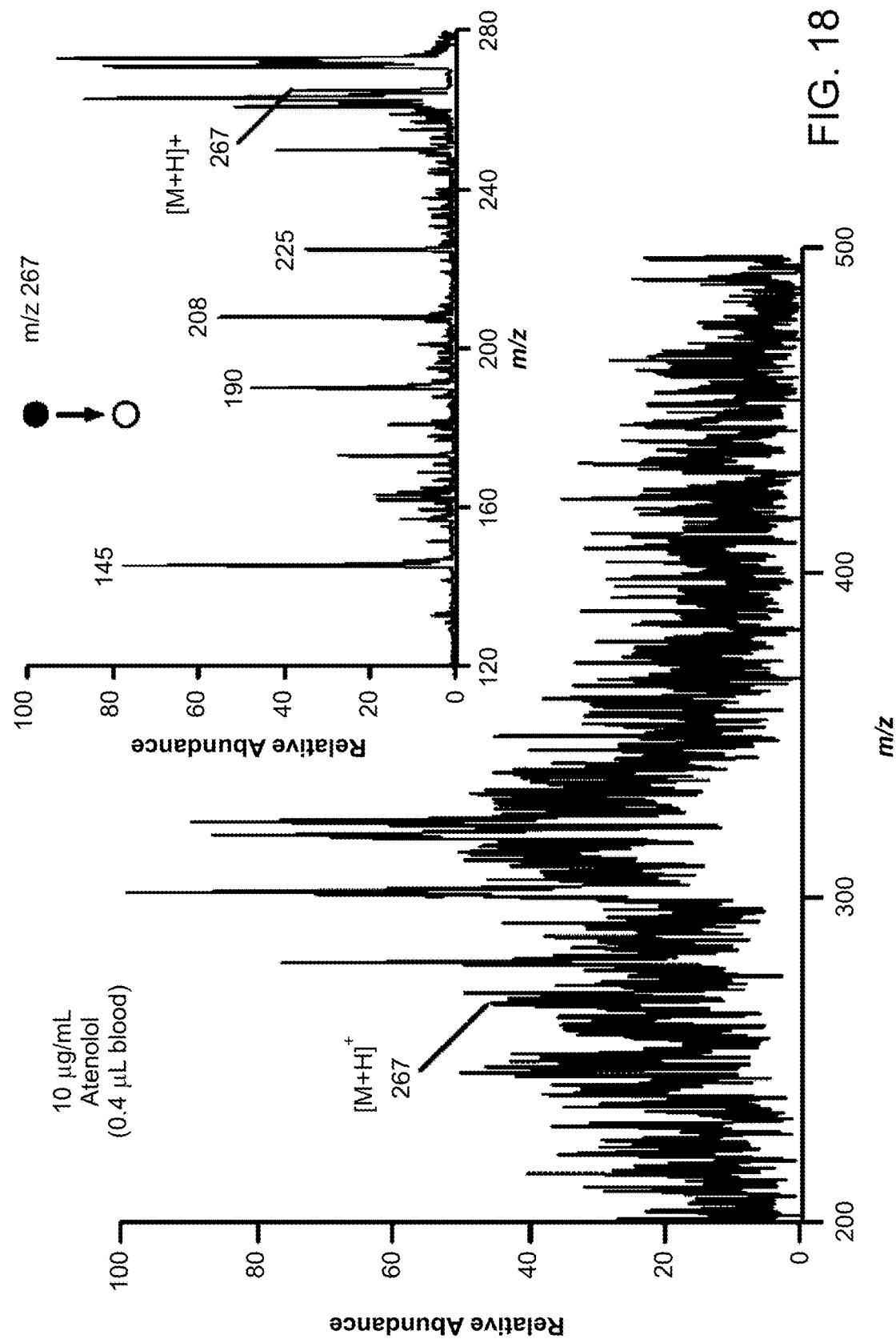
FIG. 18 is a mass spectrum of whole blood spiked with 10 µg/mL atenolol. The data was obtained by combining systems and methods of the invention with a handheld mass spectrometer.

It was also observed that the paper medium served a secondary role as a filter, retaining blood cells. Significantly, samples were analyzed directly on the storage medium rather than requiring transfer from the paper before analysis. All experiments were done in the open lab environment. Two additional features indicated that the methodology had the potential to contribute to increasing the use of mass spectrometry in primary care facilities: blood samples for analysis were drawn by means of a pinprick rather than a canula; and the experiment was readily performed using a handheld mass spectrometer (FIG. 18 and Example 10 below).

Example 10: Handheld Mass Spectrometer

Systems and methods of the invention were compatible with a handheld mass spectrometer. Paper spray was performed using a handheld mass spectrometer (Mini 10, custom made at Purdue University). Analysis of whole blood spiked with 10 μg/mL atenolol. Methanol/water (1:1; 10 μL) was applied to the paper after the blood (0.4 uL) had dried (~1 min) to generate spray for mass detection (FIG. 18). The inset shows that atenolol could readily be identified in whole blood using tandem mass spectrum even when the atenolol amount is as low as 4 ng.

Example 11: Angiotensin I

Figure 15:
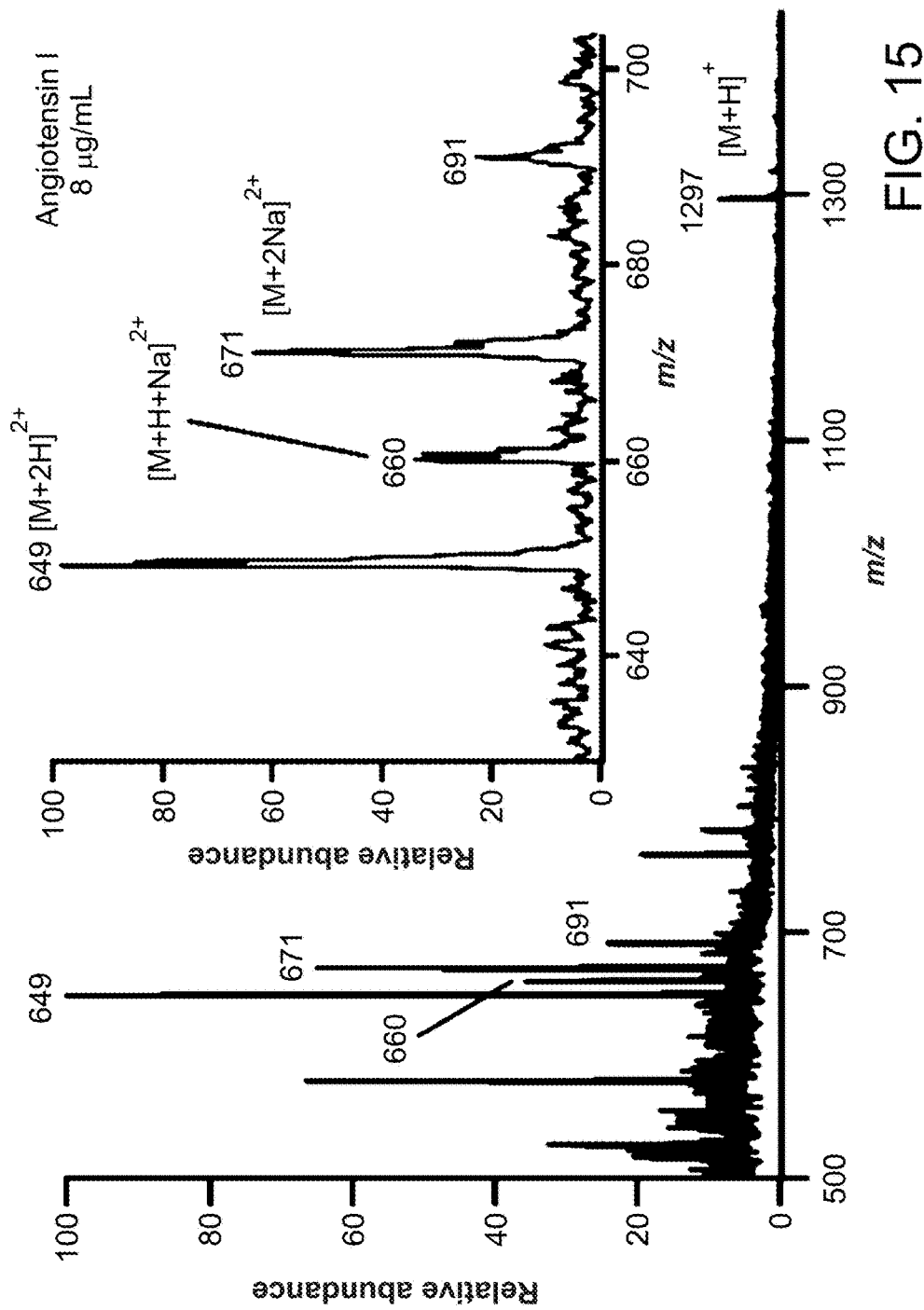
FIG. 15 is a paper spray mass spectrum of angiotensin I solution. The inset shows an expanded view over the mass range 630-700.

FIG. 15 is a paper spray mass spectrum of angiotensin I solution (Asp-Arg-Val-Tyr-Ile-His-Pro-Phe-His-Leu (SEQ ID NO: 1), 10 μL, 8 μg/mL in methanol/water, 1:1, v/v) on chromatography paper (spray voltage, 4.5 kV). The inset shows an expanded view over the mass range 630-700. The protonated ($[M+2H]^{2+}$) and sodium-adduct ions ($[M+H+Na]^{2+}$, $[M+2Na]^{2+}$) are the major ionic species.

Example 12: Agrochemicals on Fruit

Figure 34A:
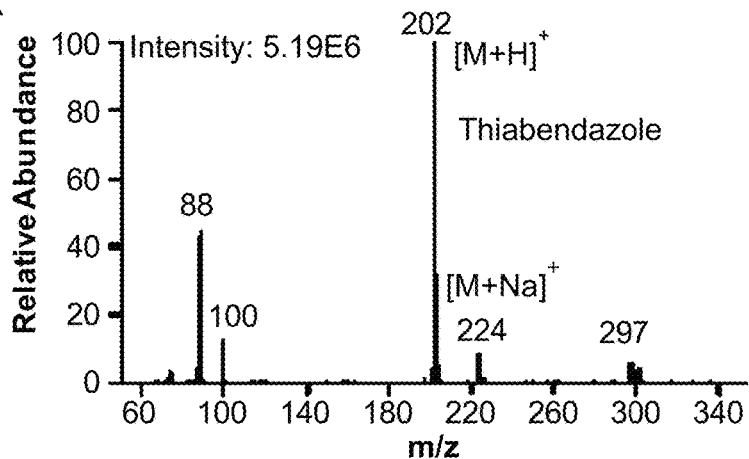
FIGS. 34A-B show mass spectra of agrochemicals that are present on a lemon peel purchased from a grocery store and swabbed with paper.
Figure 34B:
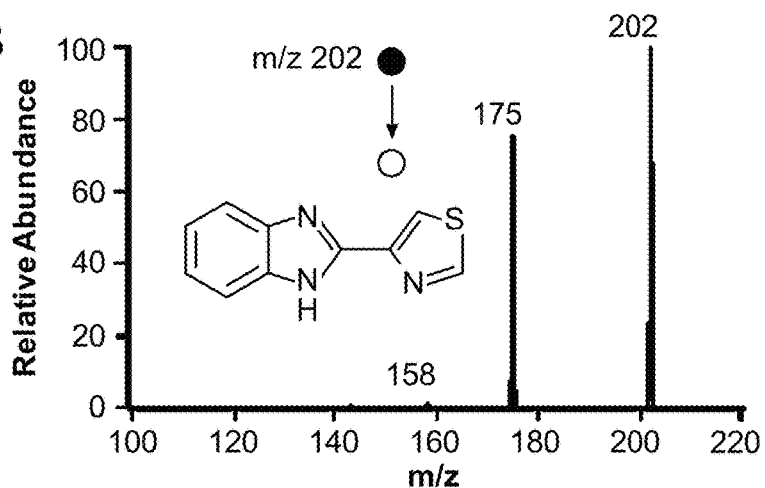
Figure 35:
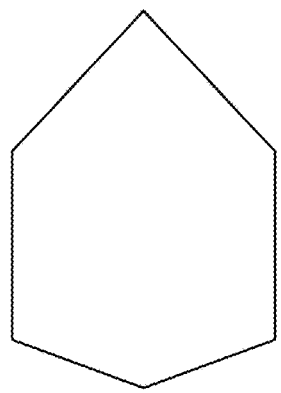
FIG. 35 shows a design of a substrate for paper spray with multiple corners. The angle of the corner to be used for spray is smaller than that of other corners.
Figure 36A:
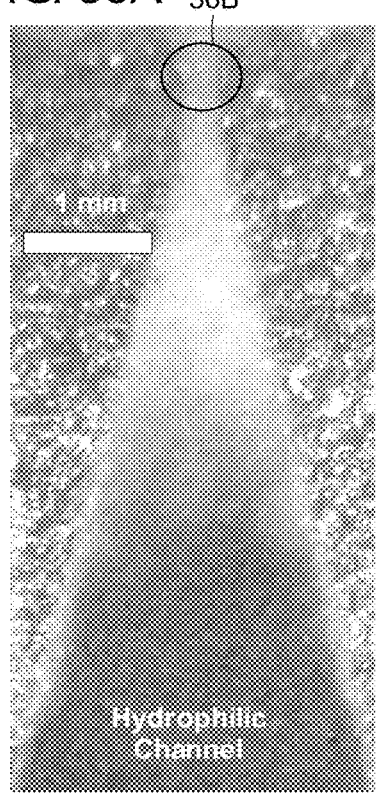
FIGS. 36A-B show a spray tip fabricated on a piece of chromatography paper using SU-8 2010 photoresist.
Figure 36B:
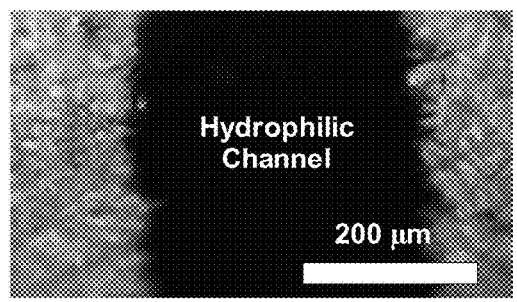
Figure 36C:
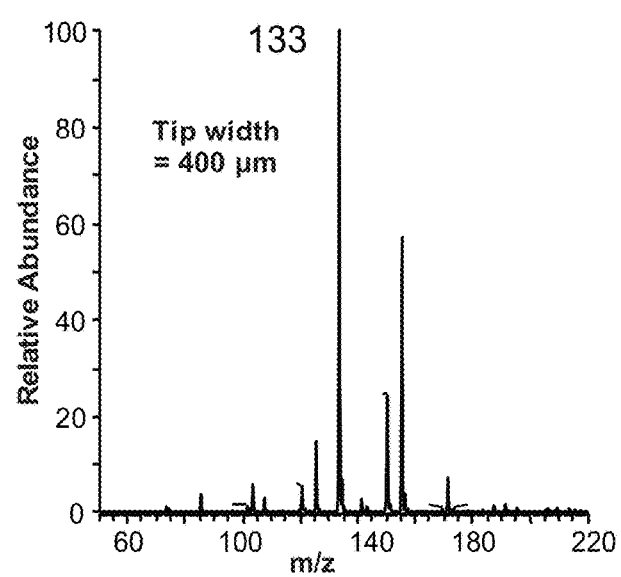
FIG. 36C shows a MS spectrum of methanol/water solution containing a mixture of asparagines.

Sample collection by paper wiping followed by analysis using probes of the invention was used for fast analysis of agrochemicals on fruit. Chromatography paper (3×3 cm) wetted with methanol was used to wipe a 10 cm² area on the peel of a lemon purchased from a grocery store. After the methanol had dried, a triangle was cut from the center of the paper and used for paper spray by applying 10 μL methanol/water solution. The spectra recorded (FIGS. 34A-B) show that a fungicide originally on the lemon peel, thiabendazole (m/z 202 for protonated molecular ion and m/z 224 for sodium adduct ion), had been collected onto the paper and could be identified easily with MS and confirmed using MS/MS analysis. Another fungicide imazalil (m/z 297) was also observed to be present.

Example 13: Tumor Sample

Systems and methods of the invention were used to analyze human prostate tumor tissue and normal tissue. Tumor and adjacent normal tissue sections were 15 µm thick and fixed onto a glass slide for an imaging study using desorption electrospray ionization (DESI). A metal needle was used to remove a 1 mm$^2$×15 µm volume of tissue from the glass slide from the tumor region and then from the normal region and place them onto the surface of the paper triangle for paper spray analysis.

Figure 17A:
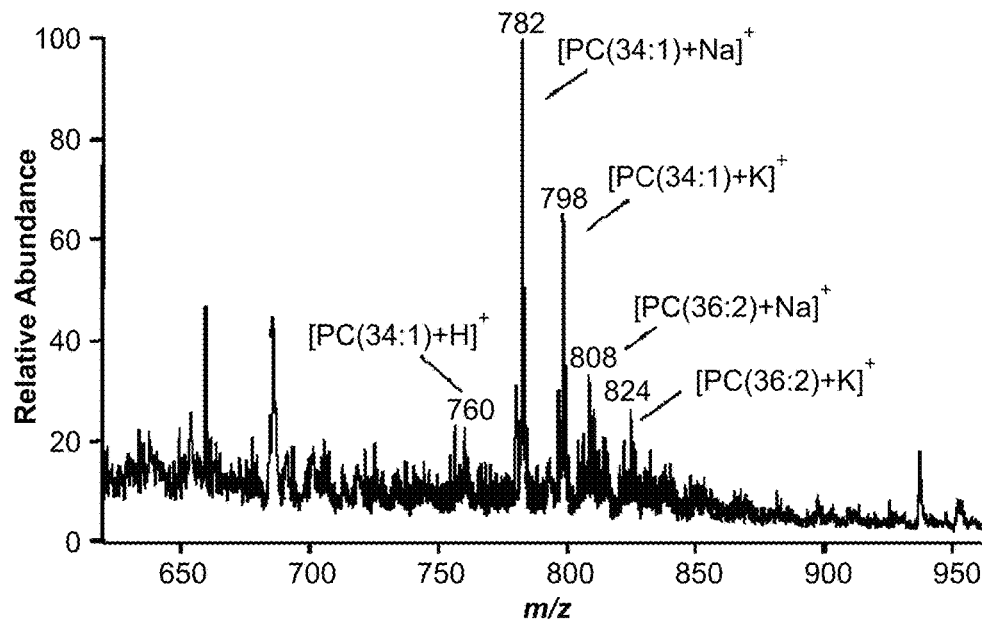
FIGS. 17A-B are mass spectra showing direct analysis of human prostate tumor tissue and normal tissue.
Figure 17B:
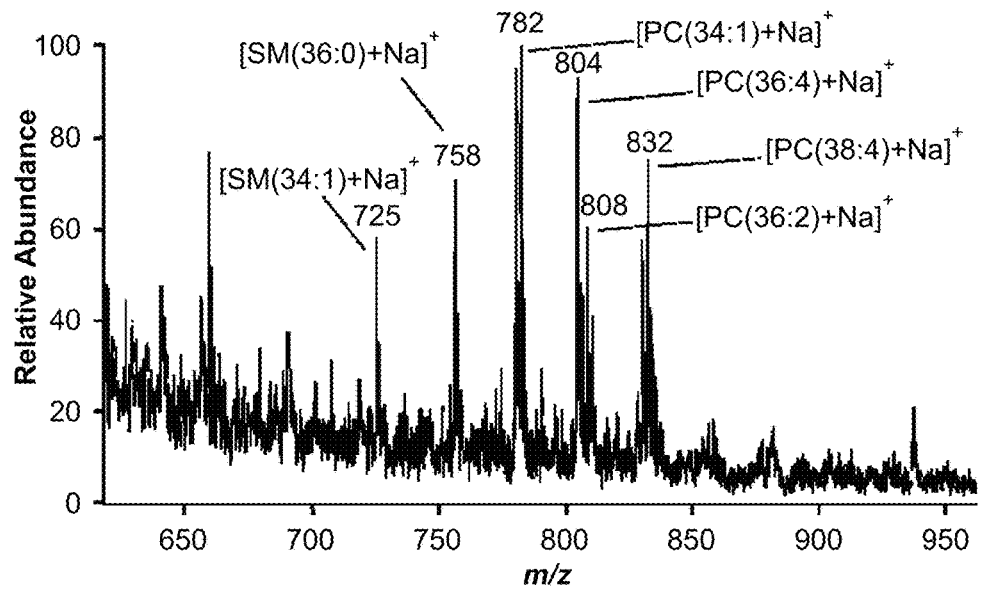

A droplet of methanol/water (1:1 v:v; 10 µl) was added to the paper as solvent and then 4.5 kV positive DC voltage applied to produce the spray. Phospholipids such as phosphatidylcholine (PC) and sphingomyelin (SM) were identified in the spectrum (FIGS. 17A-B). The peak of [PC(34:1)+K]$^+$ at m/z 798 was significantly higher in tumor tissue and peaks [SM(34:1)+Na]$^+$ at m/z 725, [SM(36:0)+Na]$^+$ at m/z 756, and [SM(36:4)+Na]$^+$ at m/z 804 were significantly lower compared with normal tissue.

Example 14: Therapeutic Drug Monitoring

The administration of a drug depends on managing the appropriate dosing guidelines for achievement of a safe and effective outcome. This guideline is established during clinical trials where the pharmacokinetics (PK) and pharmacodynamics (PD) of the drug are studied. Clinical trials use PK-PD studies to establish a standard dose, which may be fixed or adjusted according formulas using variables like body mass, body surface area, etc. However, the drug exposure, i.e. the amount of drug circulating over time, is influenced by a number of factors that vary from patient to patient. For example, an individuals' metabolic rate, the type and level of plasma proteins, and pre-existing conditions such as renal and/or hepatic impairment all play a role in affecting the exposure of the drug in vivo. Further, administration of a drug in combination with other medications may also affect exposure. As a result, it is often difficult to predict and prescribe an optimum regimen of drug administration.

Over- or underexposure to a drug can lead to toxic effects or decreased efficacy, respectively. To address these concerns, therapeutic drug monitoring (TDM) can be employed. TDM is the measurement of active drug levels in the body followed by adjustment of drug dosing or schedules to increase efficacy and/or decrease toxicity. TDM is indicated when the variability in the pharmacokinetics of a drug is large relative to the therapeutic window, and there is an established relationship between drug exposure and efficacy and/or toxicity. Another requirement for TDM is that a sufficiently precise and accurate assay for the active ingredient must be available. Immunoassays and liquid chromatography mass spectrometry (LC-MS) are commonly used methods for TDM. In comparison with immunoassay, LC-MS has advantages which include wide applicability, high sensitivity, good quantitation, high specificity and high throughput. Probes of the invention may be coupled with standard mass spectrometers for providing point-of-care therapeutic drug monitoring.

The drug Imatinib (GLEEVEC in USA and GLIVEC in Europe/Australia, for the treatment of chronic myelogenous leu-kemia) in a dried blood spot was analyzed using paper spray and a lab-scale LTQ mass spectrometer. Quantitation of Imatinib in whole blood was achieved using the MS/MS spectra with a known concentration of Imatinib-d8 being used as the internal standard (FIG. 14C). The relative response was linear across a wide range of concentrations, including the entire therapeutic range (FIG. 14C).

Example 15: High-Throughout Detection

Figure 28A:
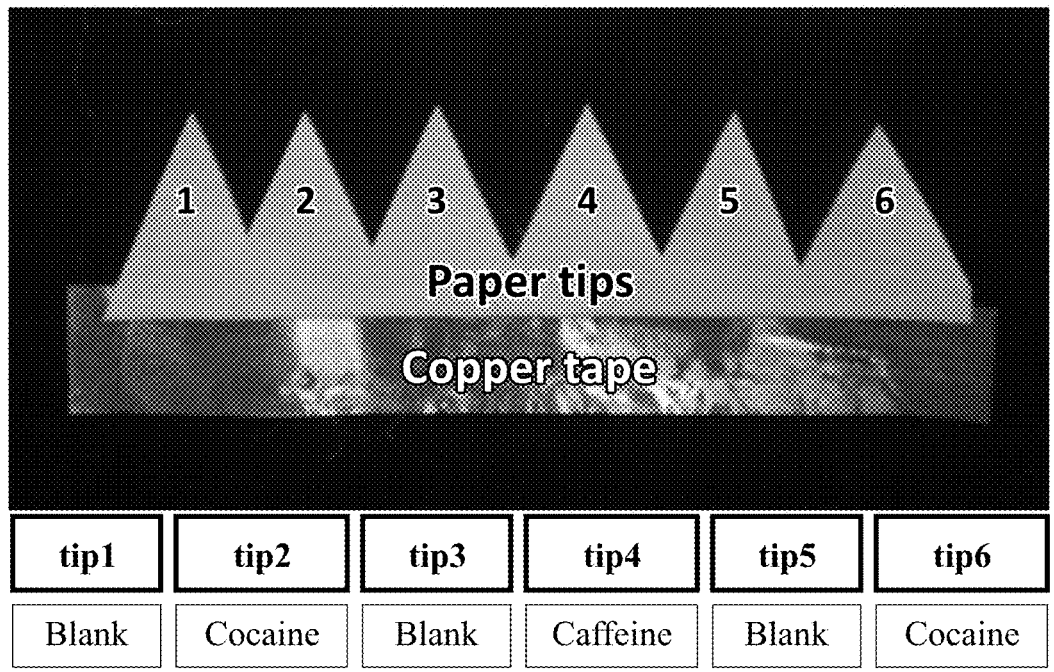
FIG. 28A is a picture of a high-throughput probe device of the invention.
Figure 28B:
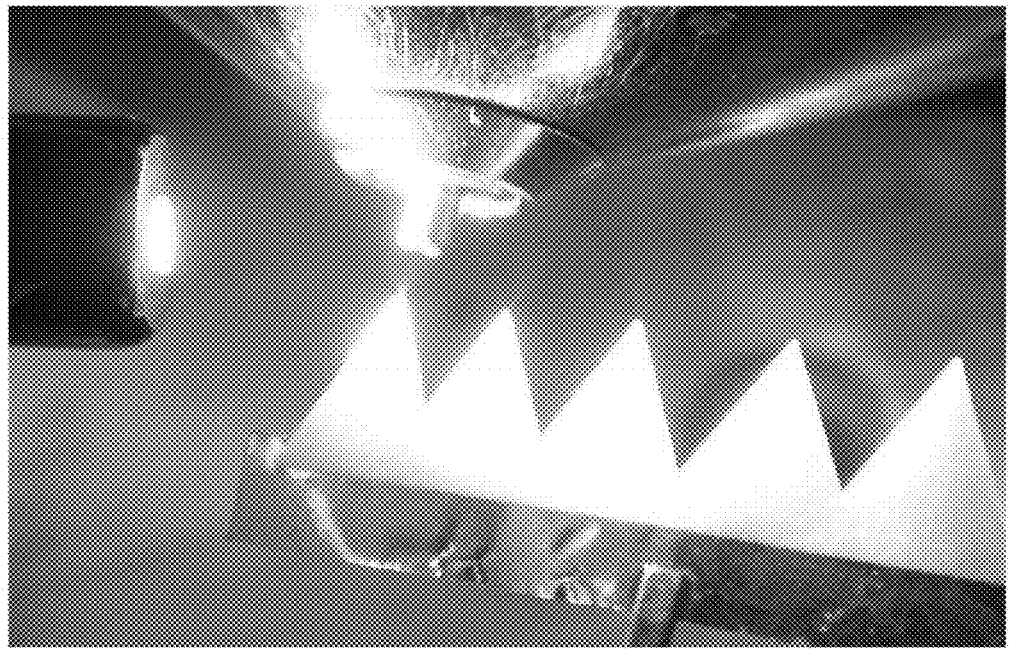
FIG. 28B shows spray from a single tip of the device into an inlet of a mass spectrometer.
Figure 28C:
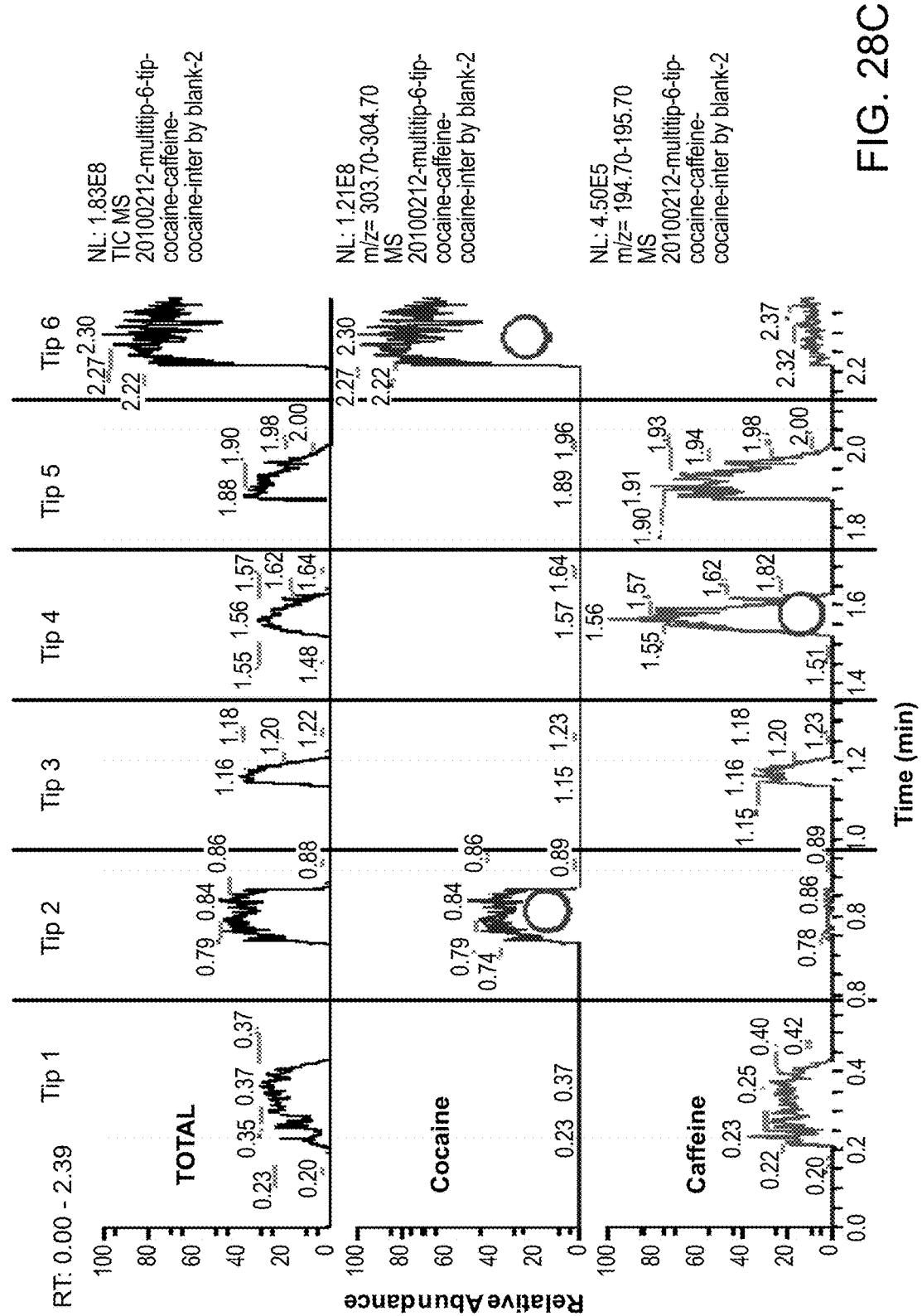
FIG. 28C is a set of mass spectra showing MS signal intensity in high-throughput mode.

Multiple-tip devices were fabricated and applied for high throughput analysis (FIG. 28A). The multiple-tip device was a set of paper triangles all connected to a single copper strip (FIG. 28A). An electrode was connected to the copper strip. Multiple samples were put on a single paper substrate and analyzed in series using the multiple-tip probe (FIGS. 28B-C). Each tip was pre-loaded with 0.2 uL methanol/water containing 100 ppm sample (cocaine or caffeine) and dried. Then the whole multiple-tip device was moved on a moving stage from left to right with constant velocity and 7 uL methanol/water was applied from the back part for each tip during movement.

To prevent the contaminant during spray, blanks were inserted between two sample tips. FIG. 28C shows the signal intensity for the whole scanning. From total intensity, six tips gave six individual high signal peaks. For cocaine, peaks only appeared when tip 2 and tip 6 were scanned. For caffeine, the highest peak came from tip 4, which was consistent with the sample loading sequence.

Example 16: Tissue Analysis

Figure 16:
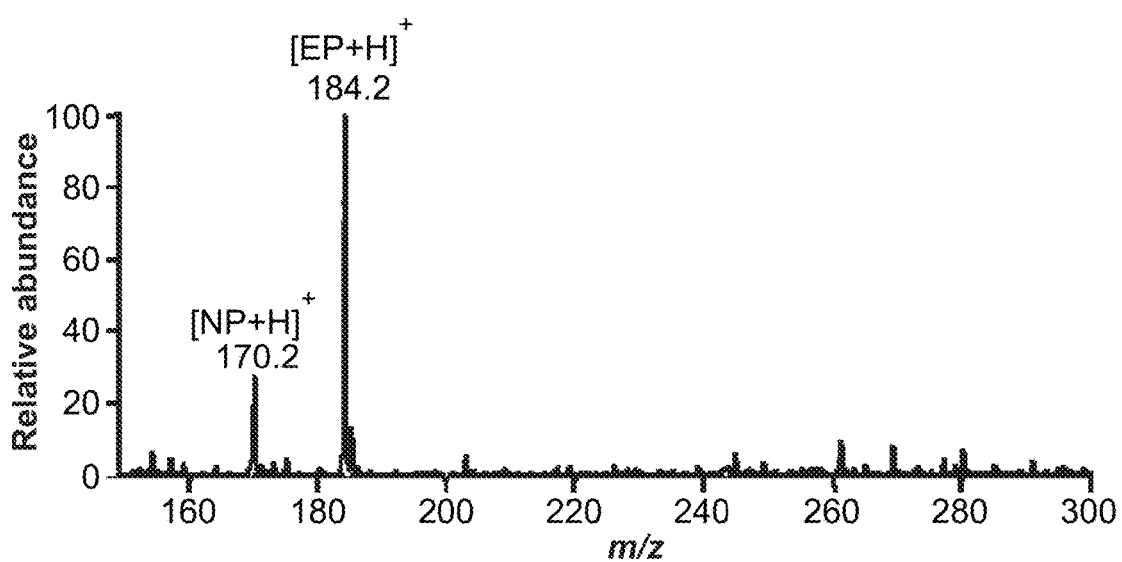
FIG. 16 is a mass spectrum showing direct analysis of hormones in animal tissue by probes of the invention.
Figure 29A:
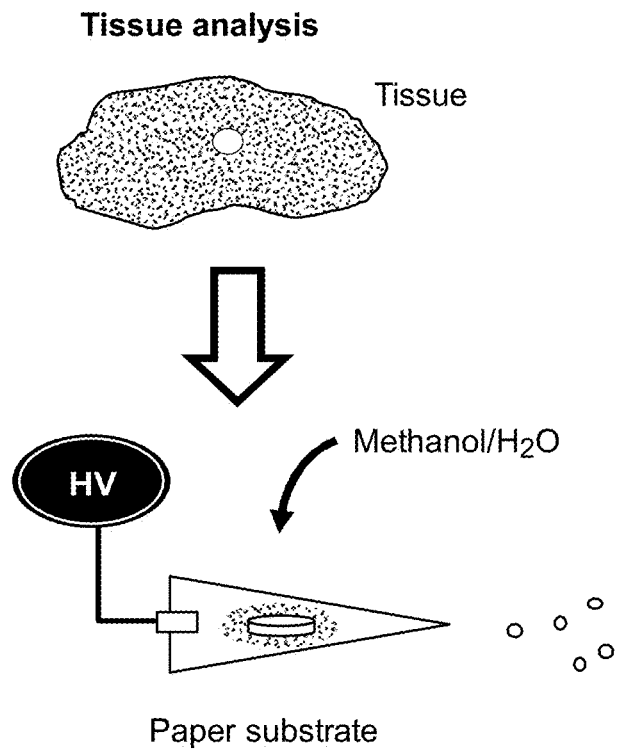
FIG. 29A is a schematic depicting a protocol for direct analysis of animal tissue using probes of the invention.
Figure 29B:
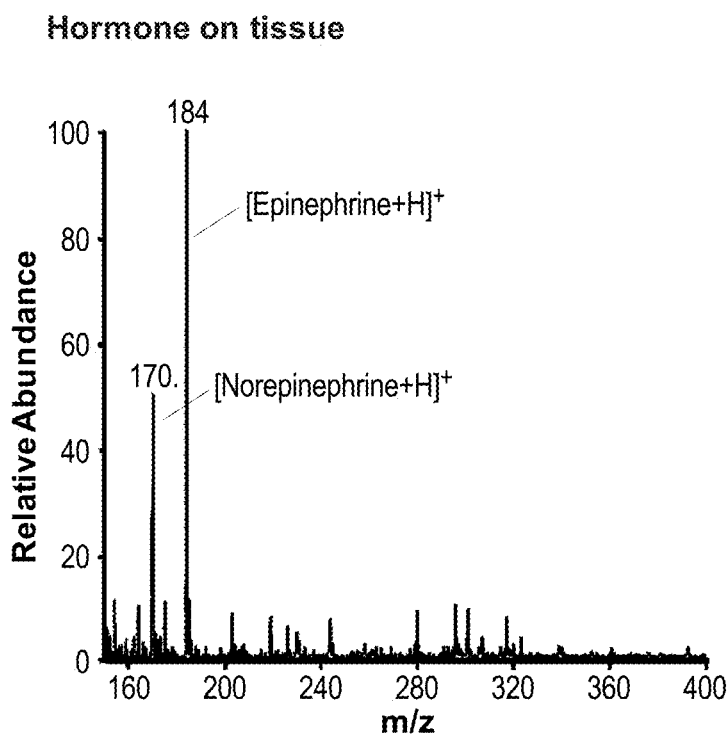

Direct analysis of chemicals in animal tissue using probes of the invention was performed as shown in FIG. 29A. A small sections of tissue were removed and placed on a paper triangle. Methanol/water (1:1 v:v; 10 µl) was added to the paper as solvent and then 4.5 kV positive DC voltage was applied to produce the spray for MS analysis. Protonated hormone ions were observed for porcine adrenal gland tissue (1 mm$^3$, FIG. 29B). FIG. 16 is a mass spectrum showing direct analysis of hormones in animal tissue by paper spray. A small piece of pig adrenal gland tissue (1 mm×1 mm×1 mm) was placed onto the paper surface, MeOH/water (1:1 v:v; 10 µl) was added and a voltage applied to the paper to produce a spray. The hormones epinephrine and norepinephrine were identified in the spectrum; at high mass the spectrum was dominated by phospolipid signals.

Lipid profiles were obtained for human prostate tissues (1 mm$^2$×15 µm, FIGS. 29C-D) removed from the tumor and adjacent normal regions. Phospholipids such as phosphatidylcholine (PC) and sphingomyelin (SM) were identified in the spectra. The peak of [PC(34:1)+K]$^+$ at m/z 798 was significantly more intense in tumor tissue (FIG. 29C) and peaks [SM(34:1)+Na]$^+$ at m/z 725, [SM(36:0)+Na]$^+$ at m/z 756, and [SM(36:4)+Na]$^+$ at m/z 804 were significantly lower compared with normal tissue (FIG. 29D).

Example 17: On-Line Derivatization

For analysis of target analytes which have relatively low ionization efficiencies and relatively low concentrations in mixtures, derivatization is often necessary to provide adequate sensitivity. On-line derivatization can be implemented by adding reagents into the spray solution, such as methanol/water solutions containing reagents appropriate for targeted analytes. If the reagents to be used are stable on paper, they can also be added onto the porous material when the probes are fabricated.

As a demonstration, 5 μL methanol containing 500 ng betaine aldehyde chloride was added onto a paper triangle and allowed to dry to fabricate a sample substrate preloaded with a derivatization reagent for the analysis of cholesterol in serum. On-line charge labeling with betaine aldehyde (BA) through its reaction with hydroxyl groups has been demonstrated previously to be very effective for the identification of cholesterol in tissue (Wu et al., *Anal Chem.* 2009, 81:7618-7624). When the paper triangle was used for analysis, 2 μL human serum was spotted onto the paper to form a dried spot and then analyzed by using paper spray ionization. A 10 μL ACN/CHCl$_3$ (1:1 v:v) solution, instead of methanol/water, was used for paper spray to avoid reaction between the betaine aldehyde and methanol.

Figure 30A:
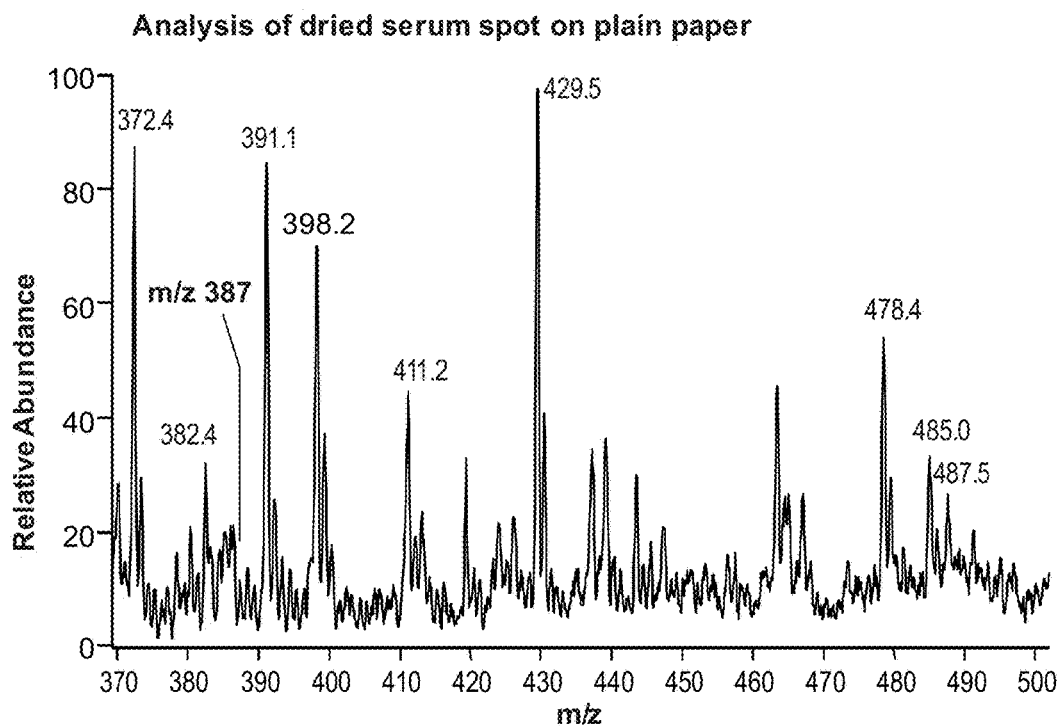
FIG. 30A shows a mass spectral analysis of a dried serum spot on plain paper.
Figure 30B:
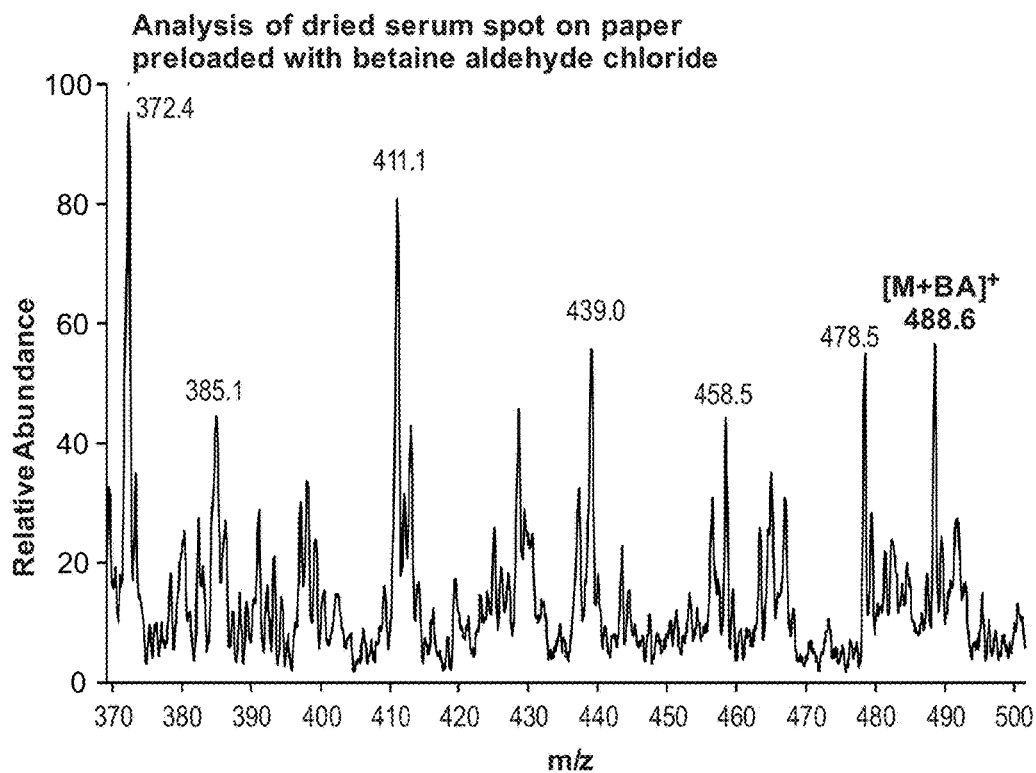
FIG. 30B shows a mass spectrum analysis of a dried serum sport on paper preloaded with betaine aldehyde (BA) chloride.
Figure 30C:
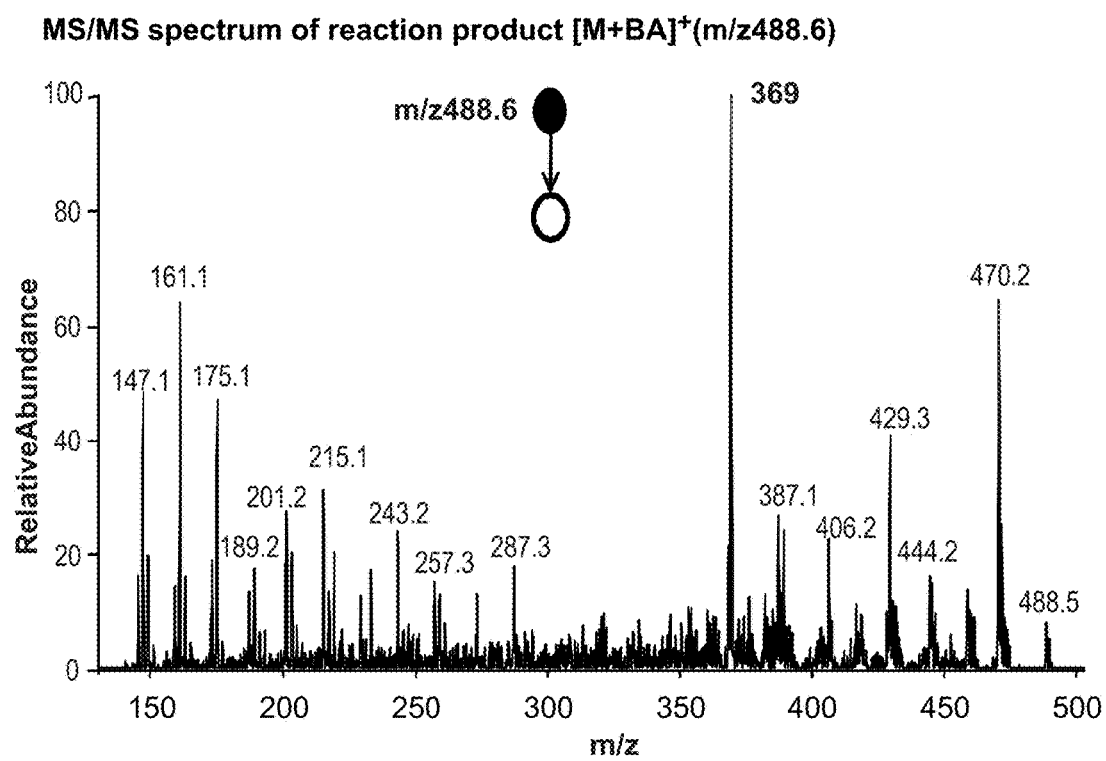
FIG. 30C shows a MS/MS analysis of reaction product $[M+BA]^+$ (m/z 488.6).

The comparison between analysis using a blank and a reagent-preloaded paper triangle is shown in FIGS. 30A-B. Without the derivatization reagent, cholesterol-related peaks, such as protonated ion [Chol+H]$^+$ (m/z 387), water loss [Chol+H–H$_2$O]$^+$ (m/z 369), and sodium adduction [Chol+Na]$^+$ (m/z 409), were not observed (FIG. 30A). With the derivatization reagent, the ion [Chol+BA]$^+$ was observed at m/z 488.6 (FIG. 30B). MS/MS analysis was performed for this ion and a characteristic fragment ion m/z 369 was observed (FIG. 30C).

Example 18: Peptide Pre-Concentration Using Modified Paper Spray Substrate

Pre-concentration of chemicals on the paper surface using photoresist treatment. Chromatography paper was rendered hydrophobic by treatment with SU-8 photoresist as described previously (Martinez et al., *Angew Chem Int. Ed.*, 2007, 46:1318-1320). Then 5 μl bradykinin 2-9 solution (100 ppm in pure H$_2$O) was applied on the paper surface. When the solution was dry, the paper was put into water and washed for 10 s. After washing, the paper triangle was held in front of the MS inlet, 10 μl pure MeOH was applied as solvent and the voltage was set at 4.5 kV for paper spray. The same experiment was done with untreated paper substrate for comparison.

Figure 31A:
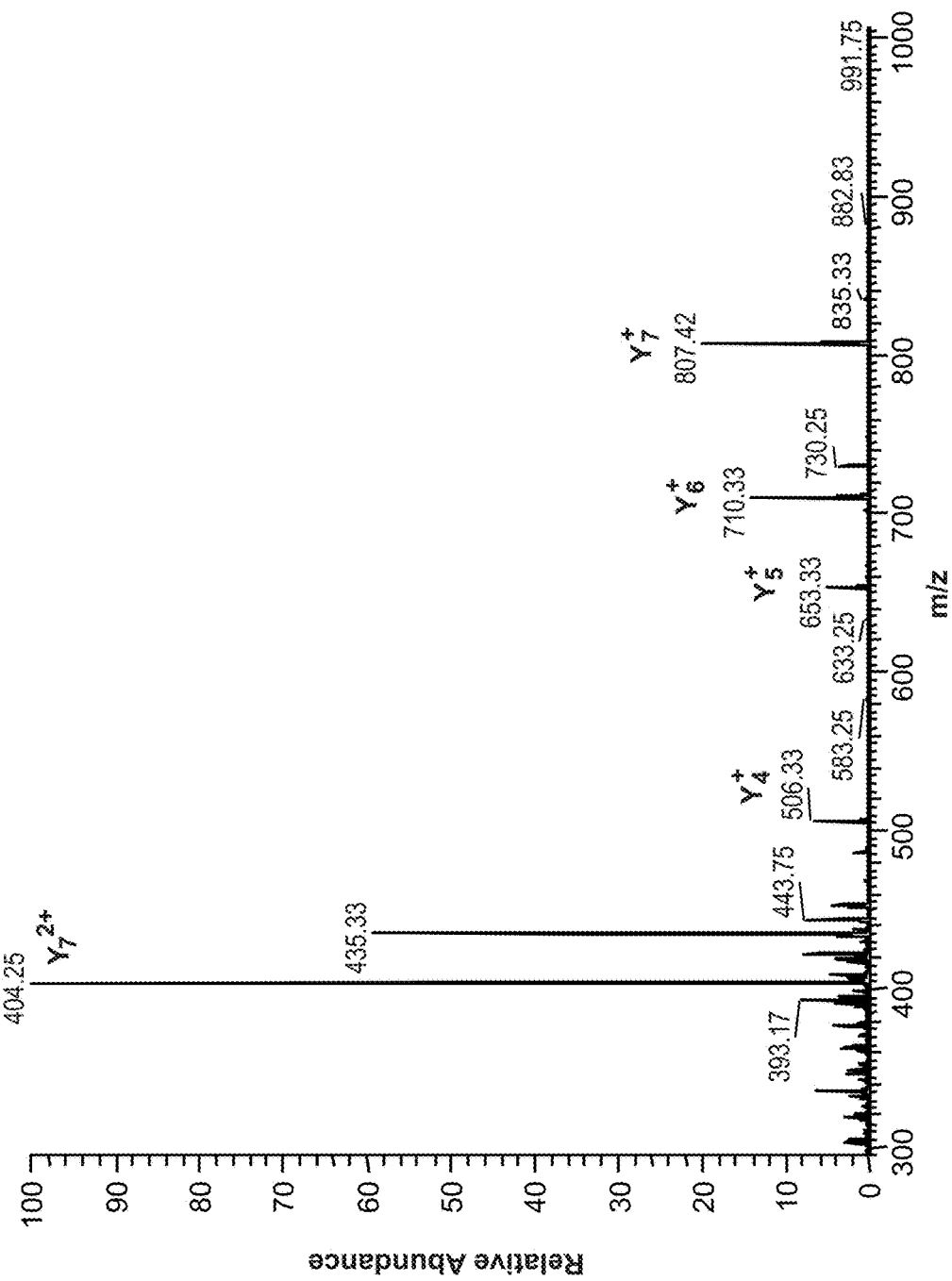
FIGS. 31A-B show MS/MS spectra recorded with modified (FIG. 31A) and unmodified (FIG. 31B) paper substrates.
Figure 31B:
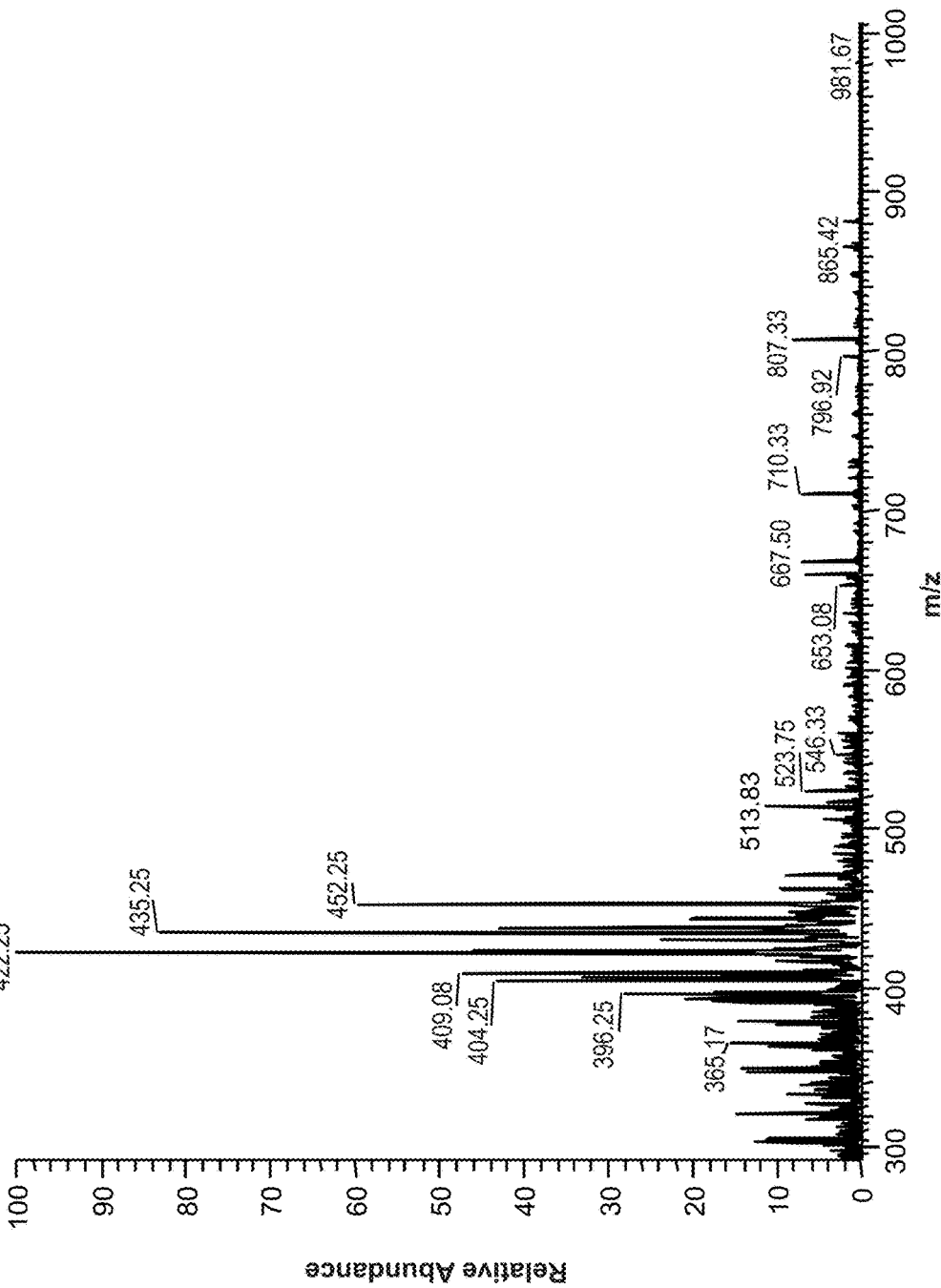

FIG. 31A shows the tandem MS spectrum of bradykinin 2-9 from paper with photoresist treatment. The intensity of the most intense fragment ion 404 is 5.66E3. FIG. 31B shows the tandem MS spectrum of bradykinin 2-9 from normal chromatography paper without photoresist treatment. The intensity of the most intense fragment ion 404 is only 1.41E1. These data show that the binding affinity between photoresist-treated chromatography paper and peptide is much higher than that between normal chromatography paper and peptide, thus more peptide can be kept on the paper surface after washing by water. When pure methanol is applied, these retained peptides will be desorbed and detected by MS. This method can be used to pre-concentrate hydrophobic chemicals on the paper surface, and other hydrophilic materials (e.g. salts) can also be removed from the paper surface.

Example 19: Inverted Polarities

The polarity of the voltage applied to the probe need not match that used in the mass analyzer. In particular, it is possible to operate the probes of the invention with a negative potential but to record the mass spectrum of the resulting positively changed ions. In negative ion mode, a large current of electrons (or solvated electrons) is produced in paper spray. These electrons, if of suitable energy, can be captured by molecules with appropriate electron affinities to generate radical anions.

Alternatively, these electrons might be responsible for electron ionization of the analyte to generate the radical cation or alternatively ESI might involve a solvent molecule which might then undergo charge exchange with the analyte to again generate the radical cation. If this process occurs with sufficient energy, characteristic fragment ions might be produced provided the radical cation is not collisionally deactivated before fragmentation can occur.

Figure 32:
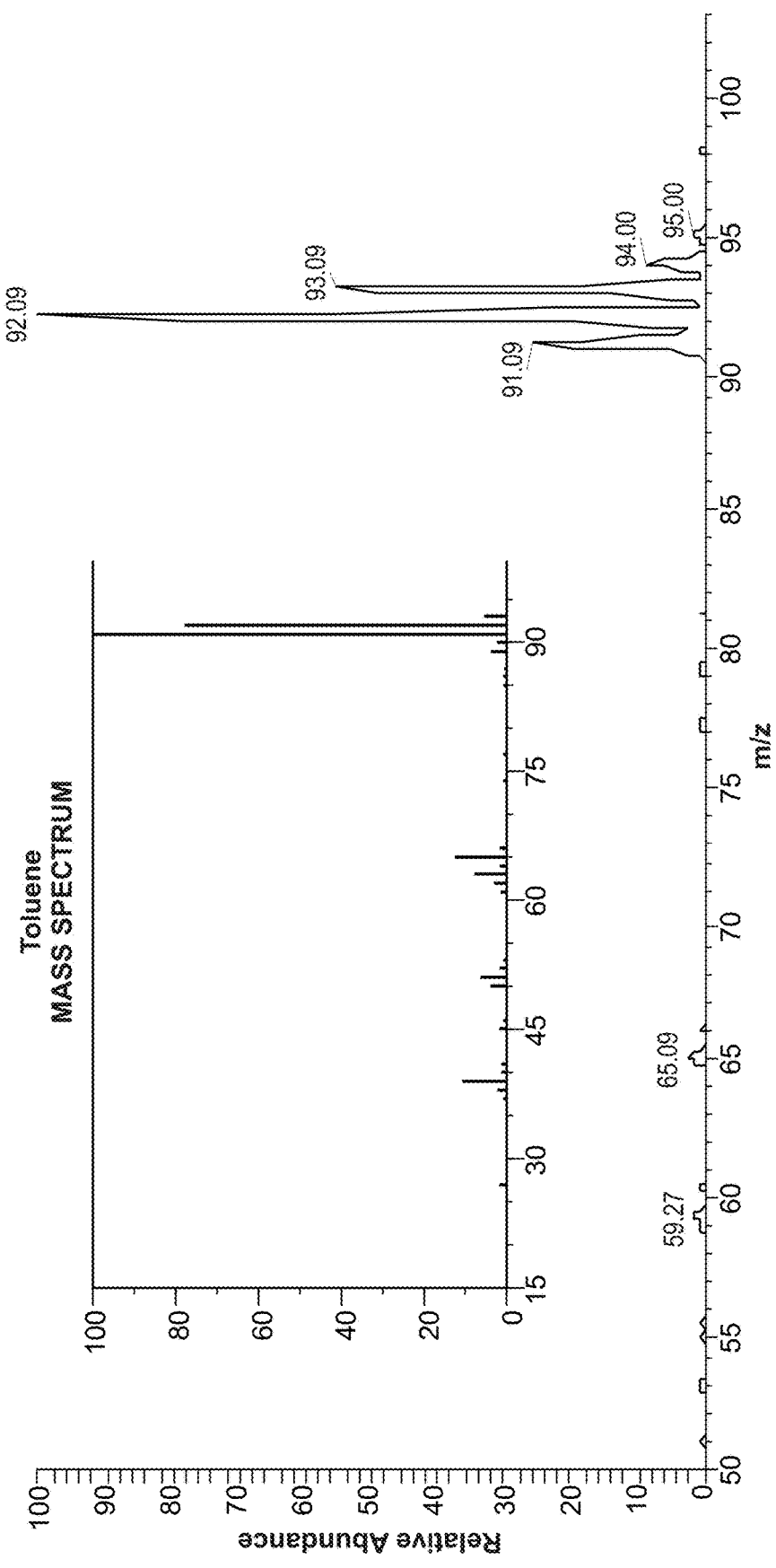
FIG. 32 is a mass spectrum showing that ions can be generated using a negative ion source potential but positively charged ions are mass-analyzed.

An experiment was done on a benchtop LTP using toluene vapor, with a probe of the invention conducted at −4.5 kV with methanol:water as solvent applied to the paper. The spectrum shown in FIG. 32 was recorded. One notes that ion/molecule reactions to give the protonated molecule, m/z 93 occur as expected at atmospheric pressure. One also notes however, the presence of the radical cation, m/z 92 and its characteristic fragments at m/z 91 and 65.

An interesting note is that the "EI" fragment ions were most easily produced when the source of toluene vapor was placed close to the MS inlet; i.e., in the cathodic region of the discharge between the paper tip and MS inlet. This suggests that direct electron ionization by energetic electrons in the "fall" region might be at least partly responsible for this behavior.

Example 20: Cartridge for Blood Analysis

Figure 33A:
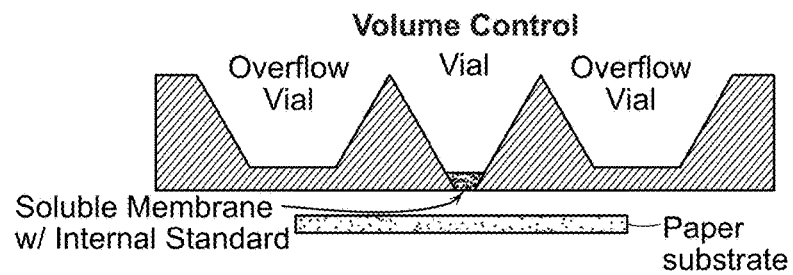
FIG. 33A is a schematic showing the design of a sample cartridge with volume control and overflowing vials. A soluble plug with internal standard chemical is used to block the bottom of the volume control vial.
Figure 33B:
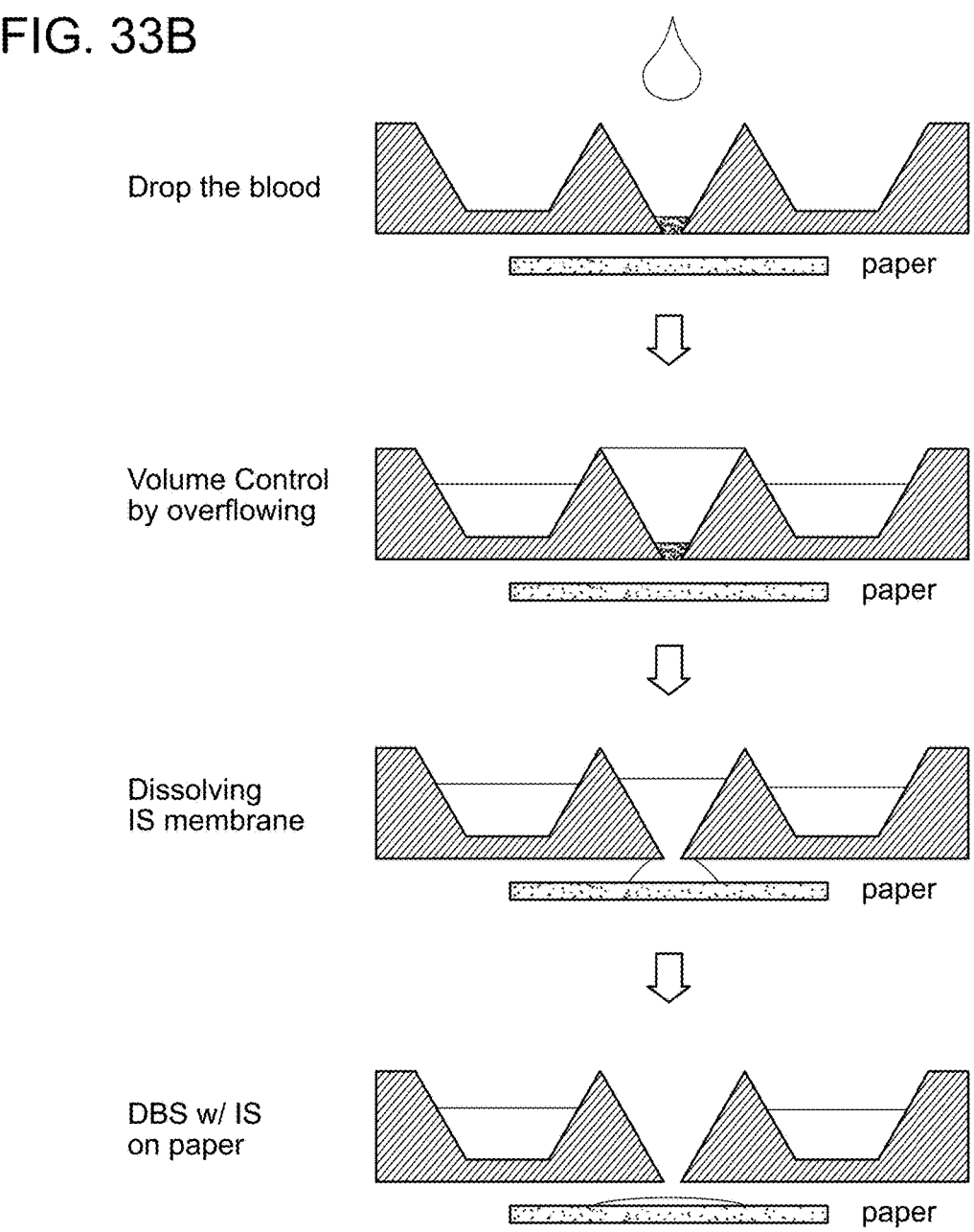
FIG. 33B shows a step-by-step process of applying blood samples onto the cartridge to prepare a dried blood spot on paper from a controlled volume of blood.

FIG. 33A shows an exemplary case for spotting blood onto porous material that will be used for mass spectral analysis. The cartridge can have a vial with a volume at the center and vials for overflows. A plug, such as a soluble membrane containing a set amount of internal standard chemical, is used to block the bottom of the vial for volume control. A drop of blood is placed in the vial (FIG. 33B). The volume of the blood in the vial is controlled by flowing the extra blood into the overflow vials (FIG. 33B). The blood in the vial is subsequently dissolved in the membrane at the bottom, mixing the internal standard chemical into the blood (FIG. 33B). Upon dissolution of the plug, blood flows to the paper substrate, and eventually forms a dried blood spot having a controlled amount of sample and internal standard (FIG. 33B).

Example 21: Microorganism Analysis and Identification

In certain aspects, probes of the invention can be used to analyze one or more microorganisms (e.g., bacteria, viruses, protozoans (also spelled protozoon), or fungi) in a sample. An exemplary method involves contacting a sample including a microorganism to a porous material, in which the porous material is kept separate from a flow of solvent. The method further involves applying high voltage to the porous material to generate ions of the microorganism that are expelled from the porous material, and analyzing the expelled ions, thereby analyzing the microorganism. Methods of the invention may also involve applying a solvent to the porous material. Any mass spectrometer known in the art may be used, and in certain embodiments, the mass spectrometer is a miniature mass spectrometer, such as that described for example in Gao et al. (Anal. Chem., 80:7198-7205, 2008) and Hou et al. (Anal. Chem., 83:1857-1861, 2011), the content of each of which is incorporated herein by reference herein in its entirety.

The sample may be any type of sample and may be in any form, for example, a solid, a liquid, or a gas. In certain embodiments, the sample is a human tissue or body fluid. The sample may be an in vivo sample or an extracted sample. In certain embodiments, the methods of the invention are sensitive enough to analyze and identify microorganisms without first culturing the microorganism. In some embodiments, the microorganism is cultured prior to analysis, however, methods of the invention allow for decreased culture time over that used in standard procedures.

FIG. 37 shows an exemplary method of collecting microorganisms onto probes of the invention when the sample is a gas/aerosol. The figure shows a probe of the invention housed within a cartridge. Such cartridges are described for example in PCT/US12/40513, the content of which is incorporated by reference herein in its entirety. Air is flowed through the cartridge, which causes, under appropriate fluid flow conditions, any microorganisms in the air to flow onto the substrate housed in the cartridge. Once collected, voltage and a discrete amount of solvent is applied to the probe, and ions of the microorganism are generated and expelled into a mass spectrometer for analysis.

Figure 38:
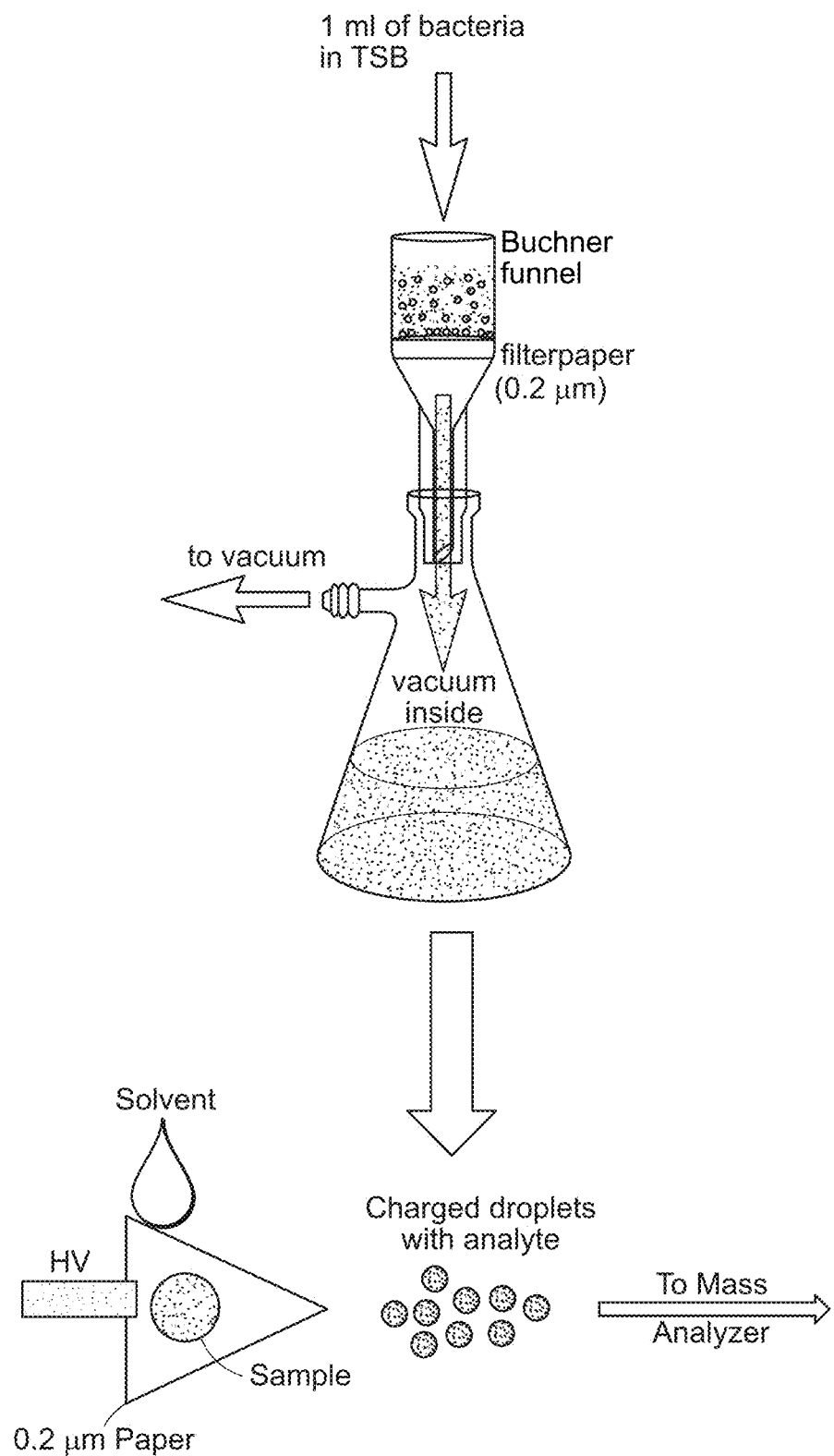
FIG. 38 shows an exemplary method of collecting microorganisms onto probes of the invention when the sample is a liquid.
Figure 39A:
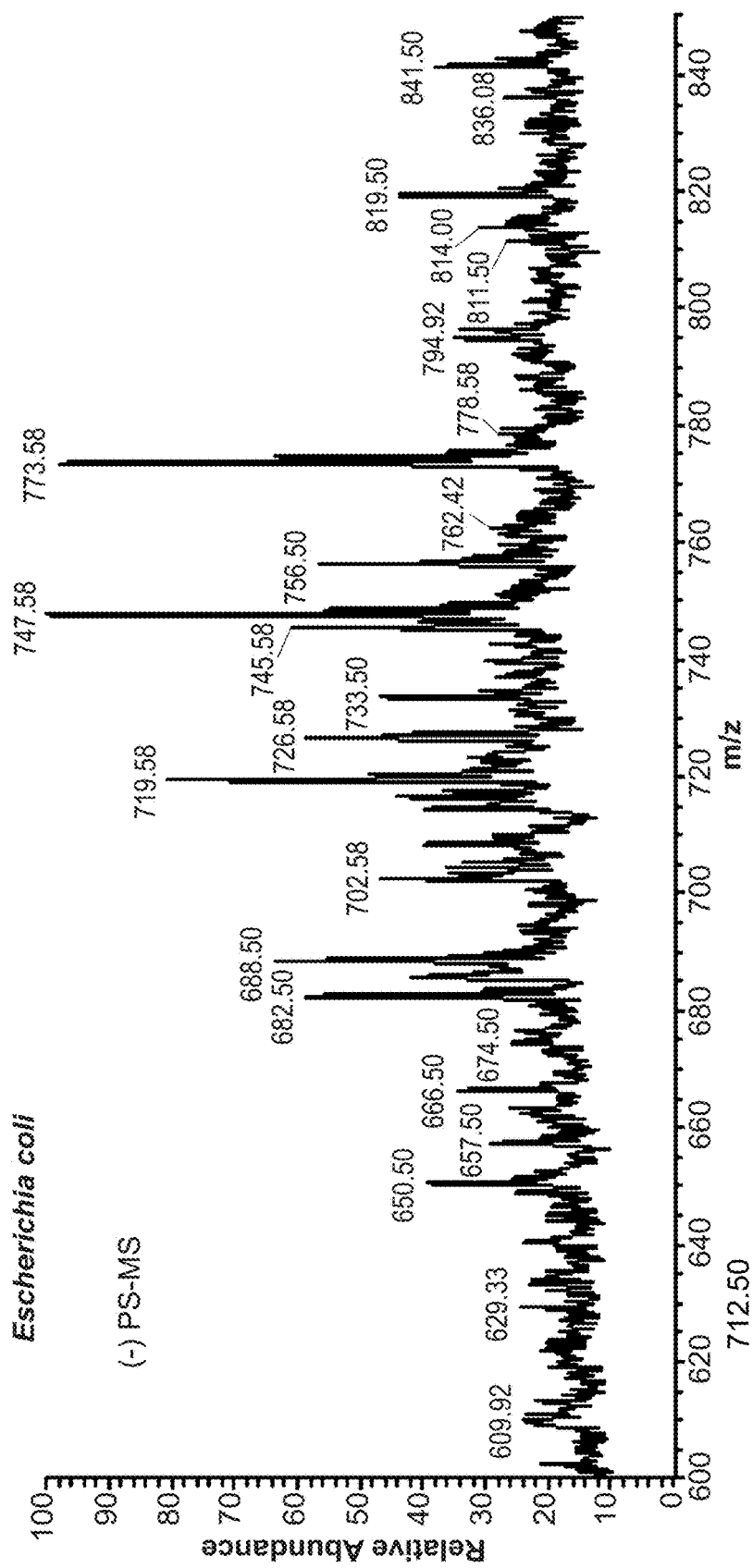
FIGS. 39A-B show mass spectra of *E. coli*.
Figure 39B:
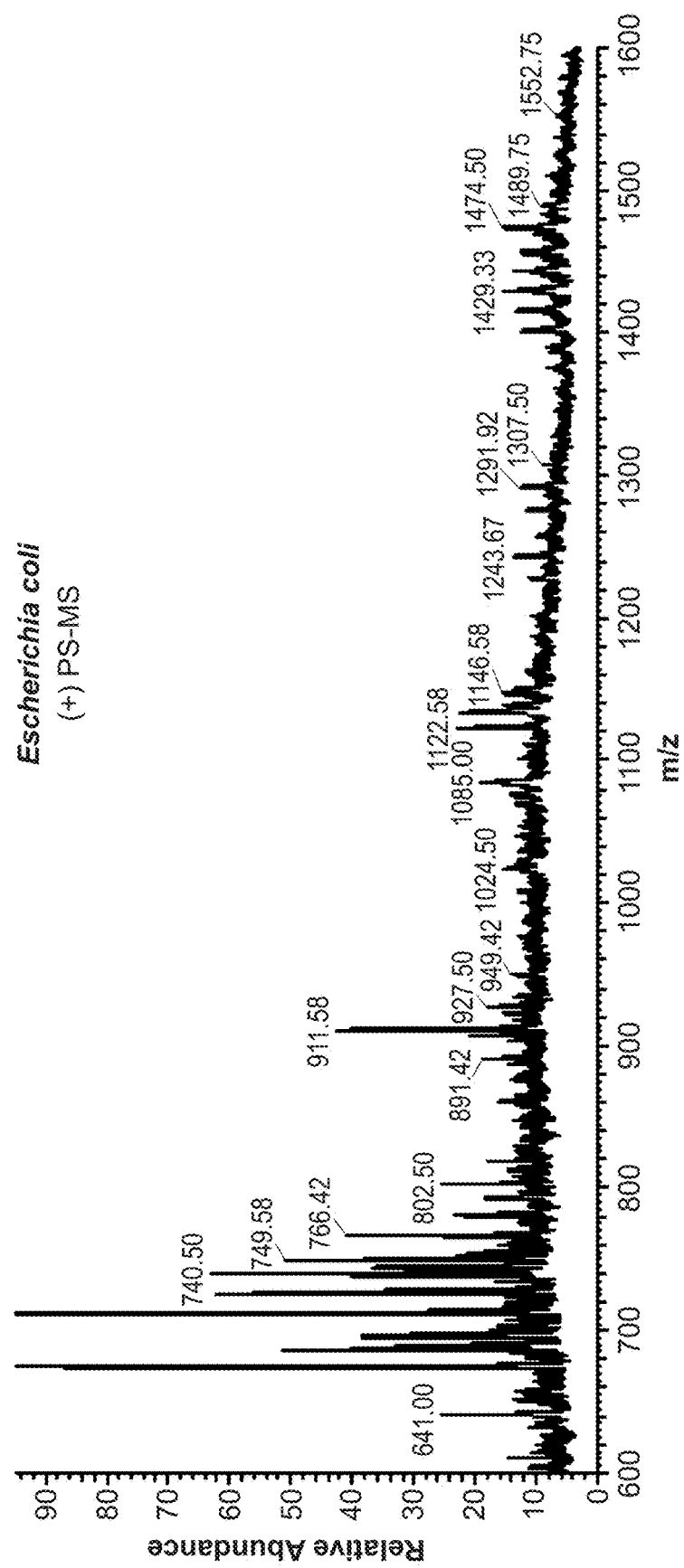

FIG. 38 shows an exemplary method of collecting microorganisms onto probes of the invention when the sample is a liquid. As shown in the figure, a porous substrate is loaded into the funnel. A liquid sample containing bacteria poured into the funnel and vacuum is used to pull the sample through the porous substrate and into a collection vessel. As the sample passes through the porous substrate, the microorganism is retained on the porous substrate. Once collected, voltage and a discrete amount of solvent is applied to the probe, and ions of the microorganism are generated and expelled into a mass spectrometer for analysis. FIGS. 39A-B show mass spectra of *E. coli* generated using the set-up as described in FIG. 38. FIG. 39A is negative ion mode and FIG. 39B is positive ion mode.

If the sample is a solid, as in the case of a microorganism grown on agar in a petri dish for example, the porous substrate can be contacted to the solid and swapped or moved across the surface such that microorganisms in the sample are retained by the porous substrate. There are other methods for collecting microorganisms from solid samples. For example, for colonies on petri dishes, a sterile inoculation loop is used to transfer one or more colonies to the porous substrate. Once collected, voltage and a discrete amount of solvent is applied to the probe, and ions of the microorganism are generated and expelled into a mass spectrometer for analysis.

Figure 40:
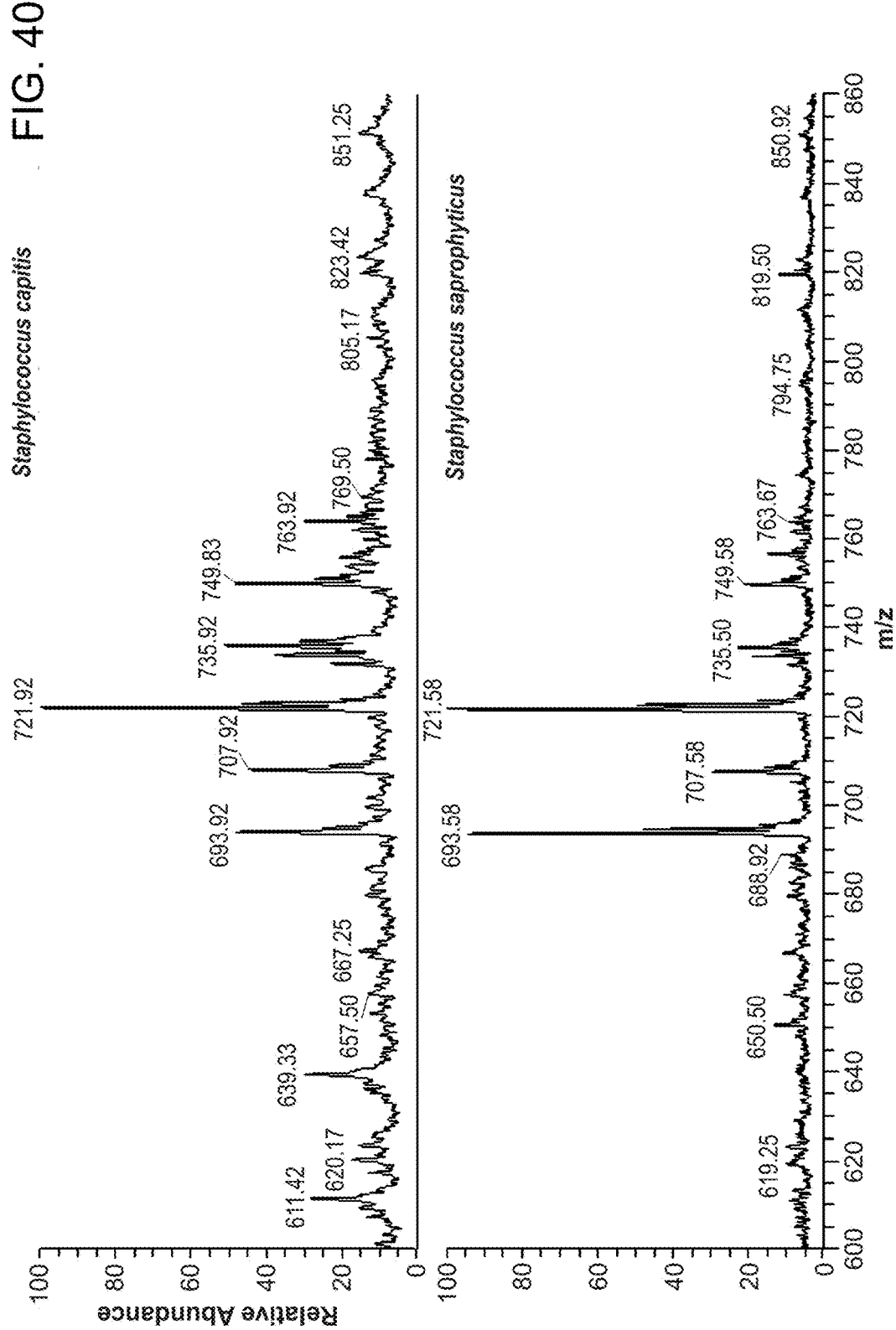
FIG. 40 show a mass spectra of different microorganisms. The top panel is a mass spectrum of *staphylococcus capitis*. The bottom panel is a mass spectrum of *staphylococcus saprophyticus*
Figure 41:
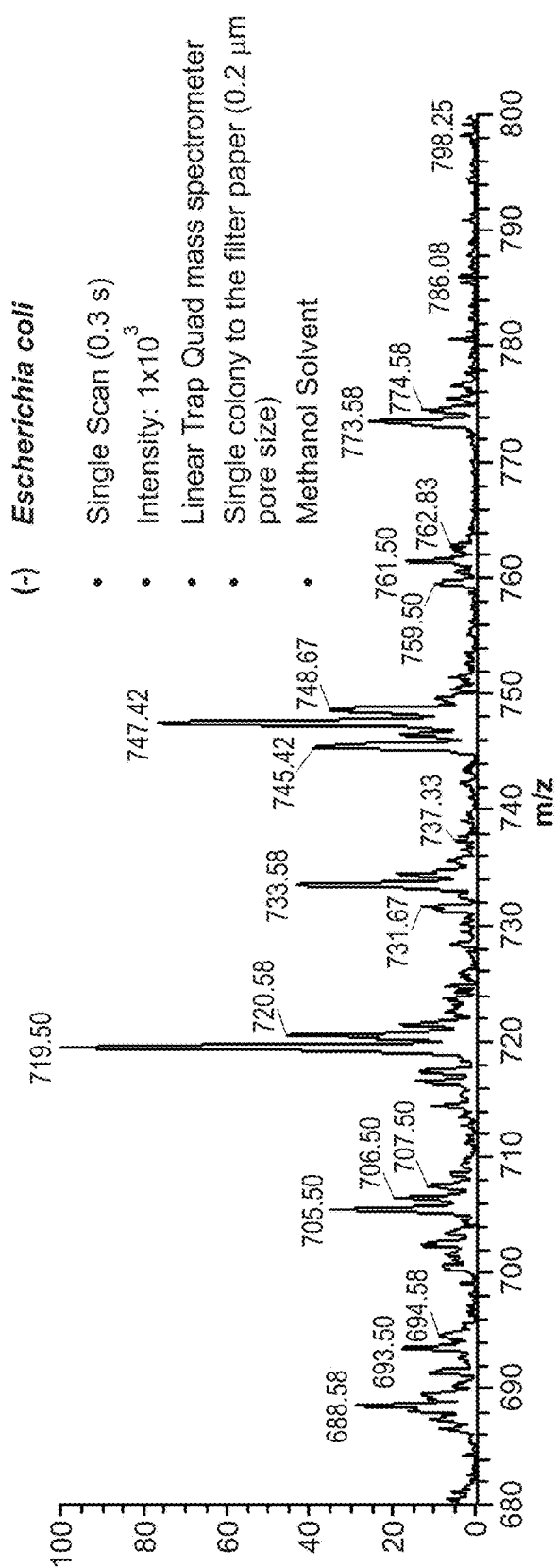
FIG. 41 shows a mass spectrum of *E. coli* acquired in negative mode.
Figure 42:
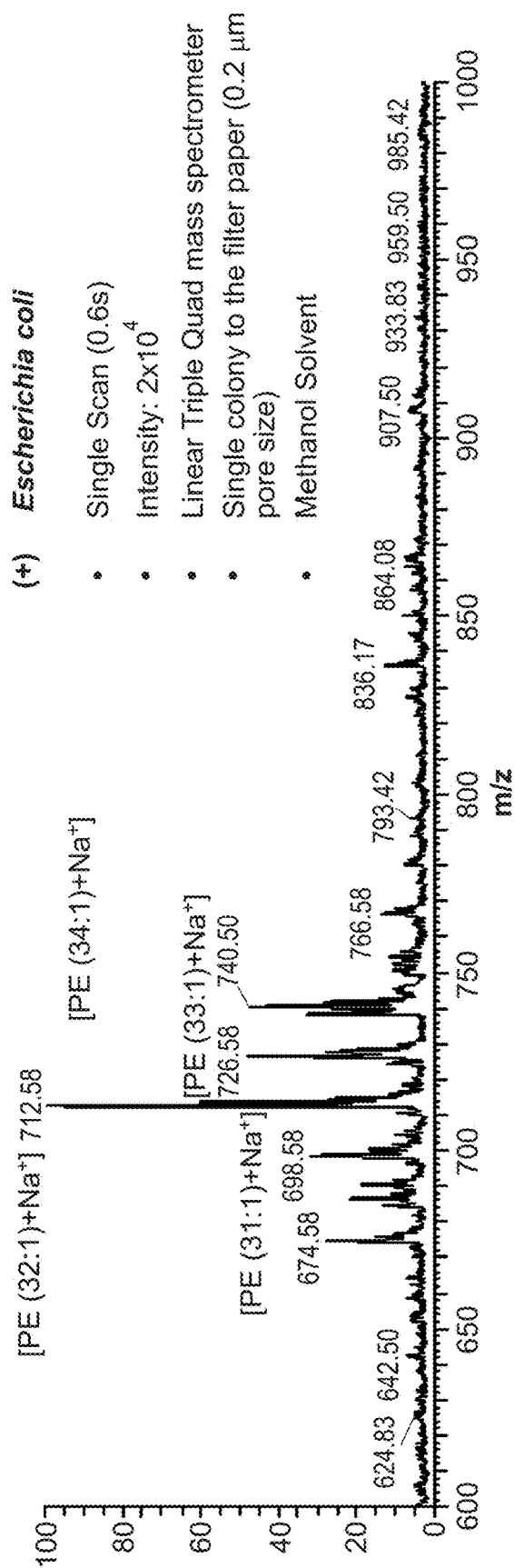
FIG. 42 shows a mass spectrum of *E. coli* acquired in positive mode.

Regardless of the collection method, voltage, and optionally a discrete amount of solvent, is applied to the probe, and ions of the microorganism are generated and expelled into a mass spectrometer for analysis. FIGS. 40-42 shows mass spectra of microorganisms analyzed using probes and methods of the invention.

Aspects of the invention also provide methods of identifying an organism, e.g., a microorganism. The methods include obtaining a mass spectrum of an organism using porous substrate probes of the invention and correlating/comparing the mass spectra with a database that includes mass spectra of known organisms (FIGS. 43-45A-F). With use of methods of the invention, the organism can be identified and classified not just at a genus and species level, but also at a sub-species (strain), a sub-strain, and/or an isolate level. The featured methods offer fast, accurate, and detailed information for identifying organisms. The methods can be used in a clinical setting, e.g., a human or veterinary setting; or in an environmental, industrial or forensic/public safety setting (e.g., clinical or industrial microbiology, food safety testing, ground water testing, air testing, contamination testing, and the like). In essence, the invention is useful in any setting in which the detection and/or identification of a microorganism is necessary or desirable.

A database for use in the invention can include a similarity cluster. The database can be used to establish, through linear discriminant analysis and related methods, a quantitative measure of the similarity of any two spectra, a similarity index. The database can include a mass spectrum from at least one member of the Clade of the organism. The database can include a mass spectrum from at least one subspecies of the organism. The database can include a mass spectrum from a genus, a species, a strain, a sub-strain, or an isolate of the organism. The database can include a mass spectrum with motifs common to a genus, a species, a strain, a sub-strain, or an isolate of the organism.

Figure 43:
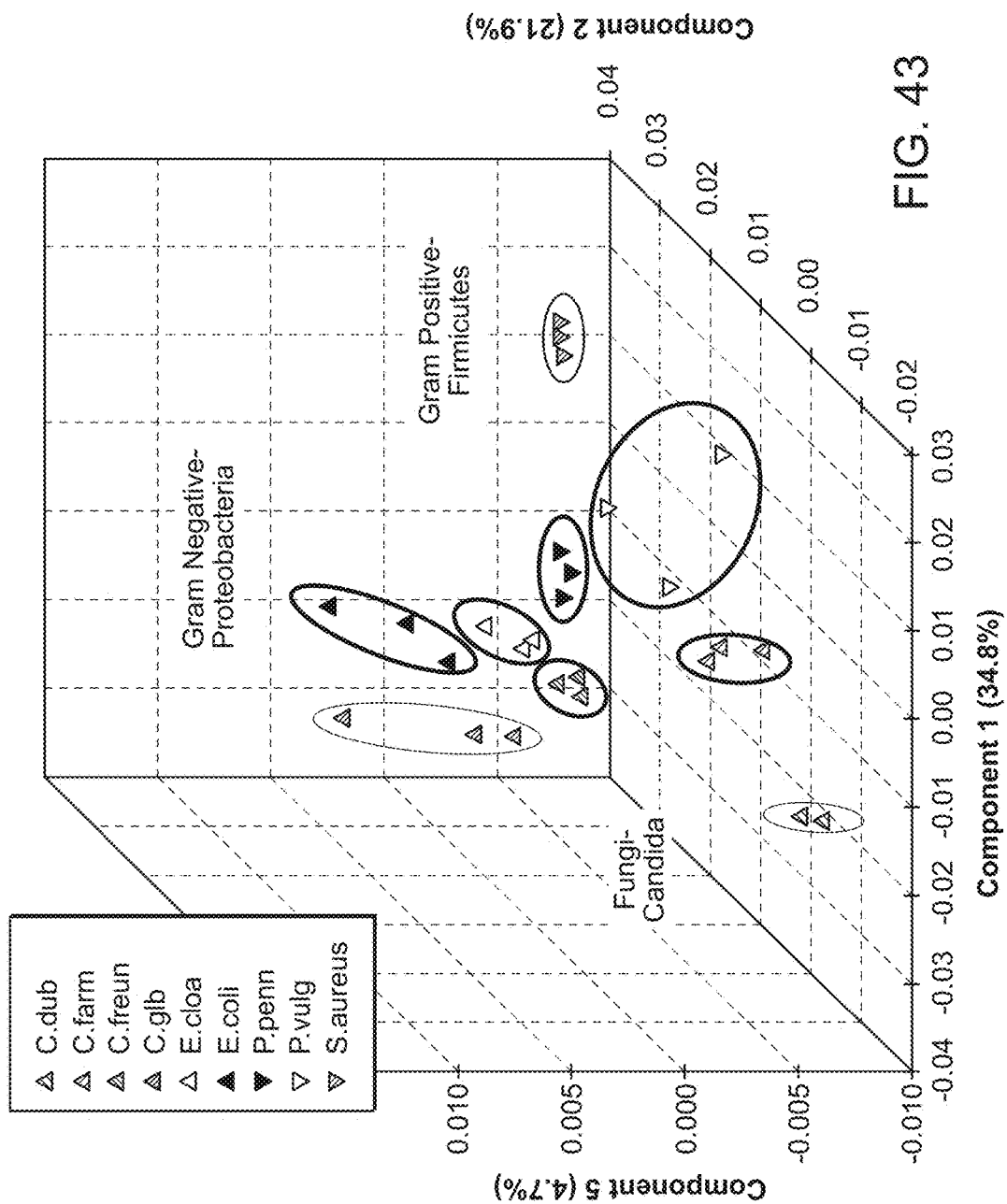
FIG. 43 is a graph showing a principal component analysis of different microorganisms.

The database(s) used with the methods described herein includes mass spectra associated with known organisms (FIGS. 45A-F). The mass spectra are typically annotated to show if they were acquired in positive or negative mode. The database(s) can contain information for a large number of isolates, e.g., about 200, about 300, about 400, about 500, about 600, about 700, about 800, about 900, about 1,000, about 1,500, about 2,000, about 3,000, about 5,000, about 10,000 or more isolates. In addition, the mass spectra of the database contain annotated information (a similarity index or cluster, see FIGS. 43-44) regarding motifs common to genus, species, sub-species (strain), sub-strain, and/or isolates for various organisms. The large number of the isolates and the information regarding specific motifs allows for accurate and rapid identification of an organism. The data in FIG. 43 show that there is separation of fungi and bacteria, a separation between gram negative and gram positive bacteria, and a separation of gram negative species.

Figure 44:
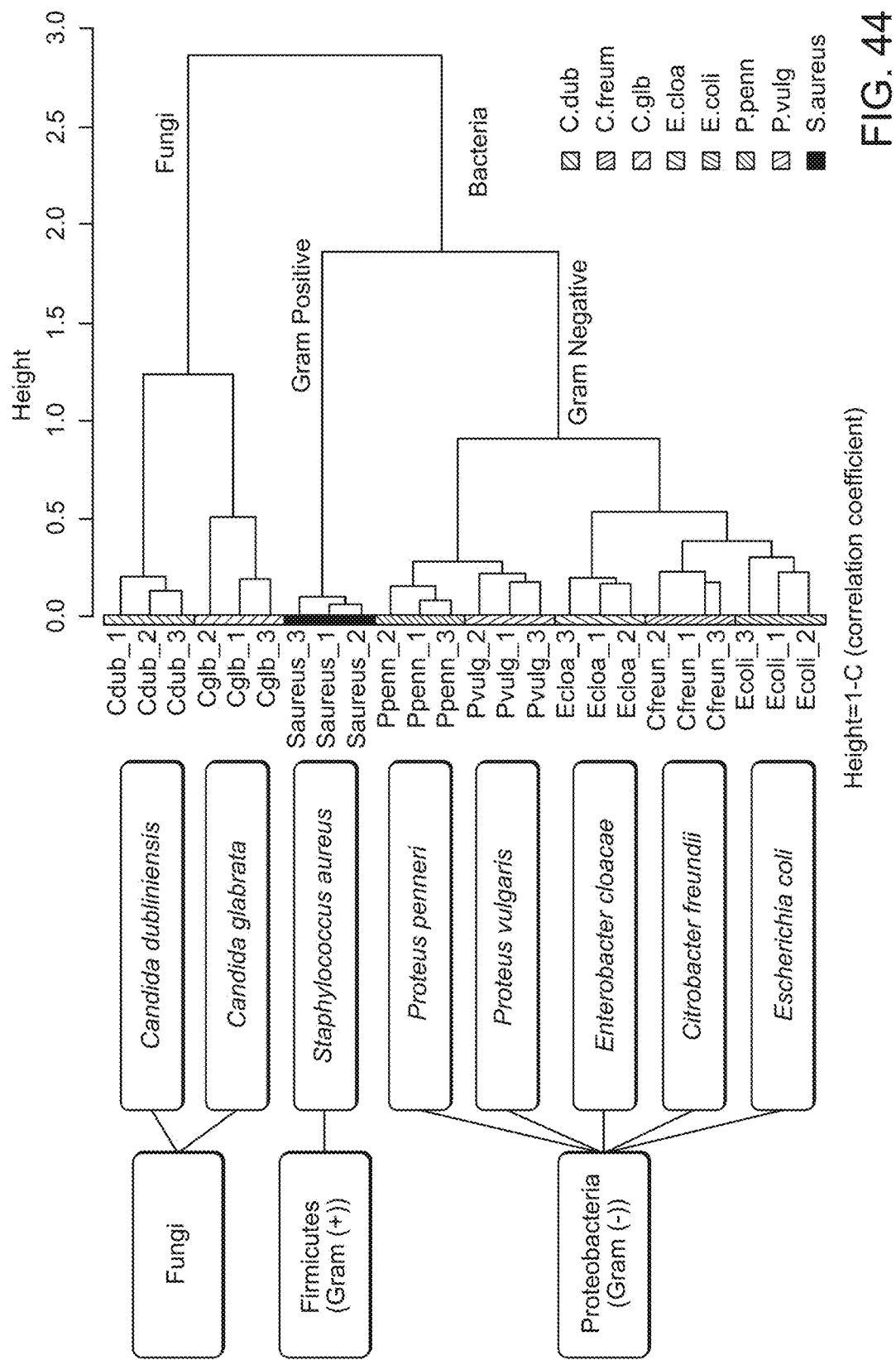
FIG. 44 is a similarity comparison of different organisms.
Figure 45A:
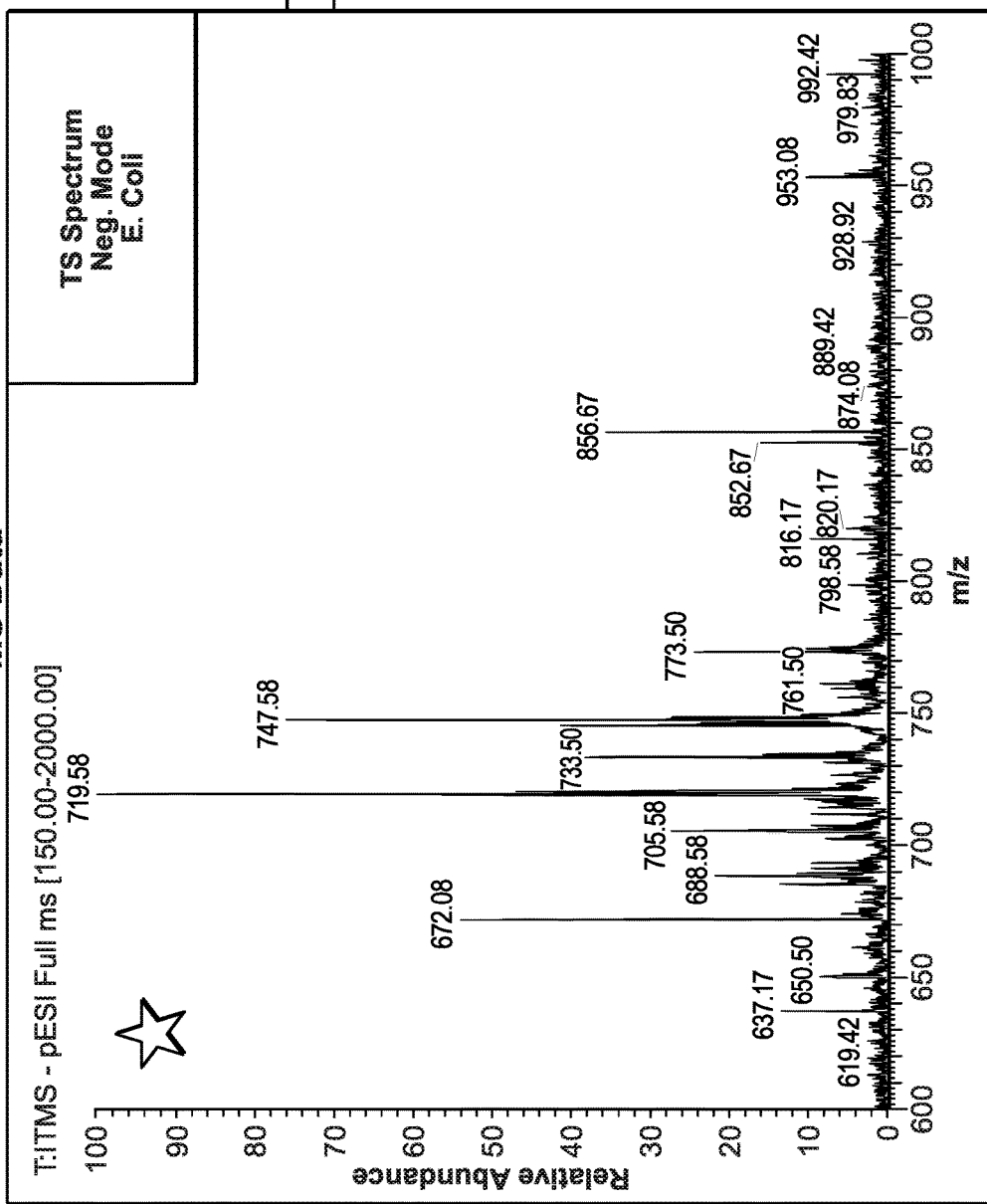
FIGS. 45A-F show a workflow for comparing a mass spectrum of an unknown microorganism to a database including mass spectra of known microorganisms to identify the unknown microorganism.
Figure 45B:
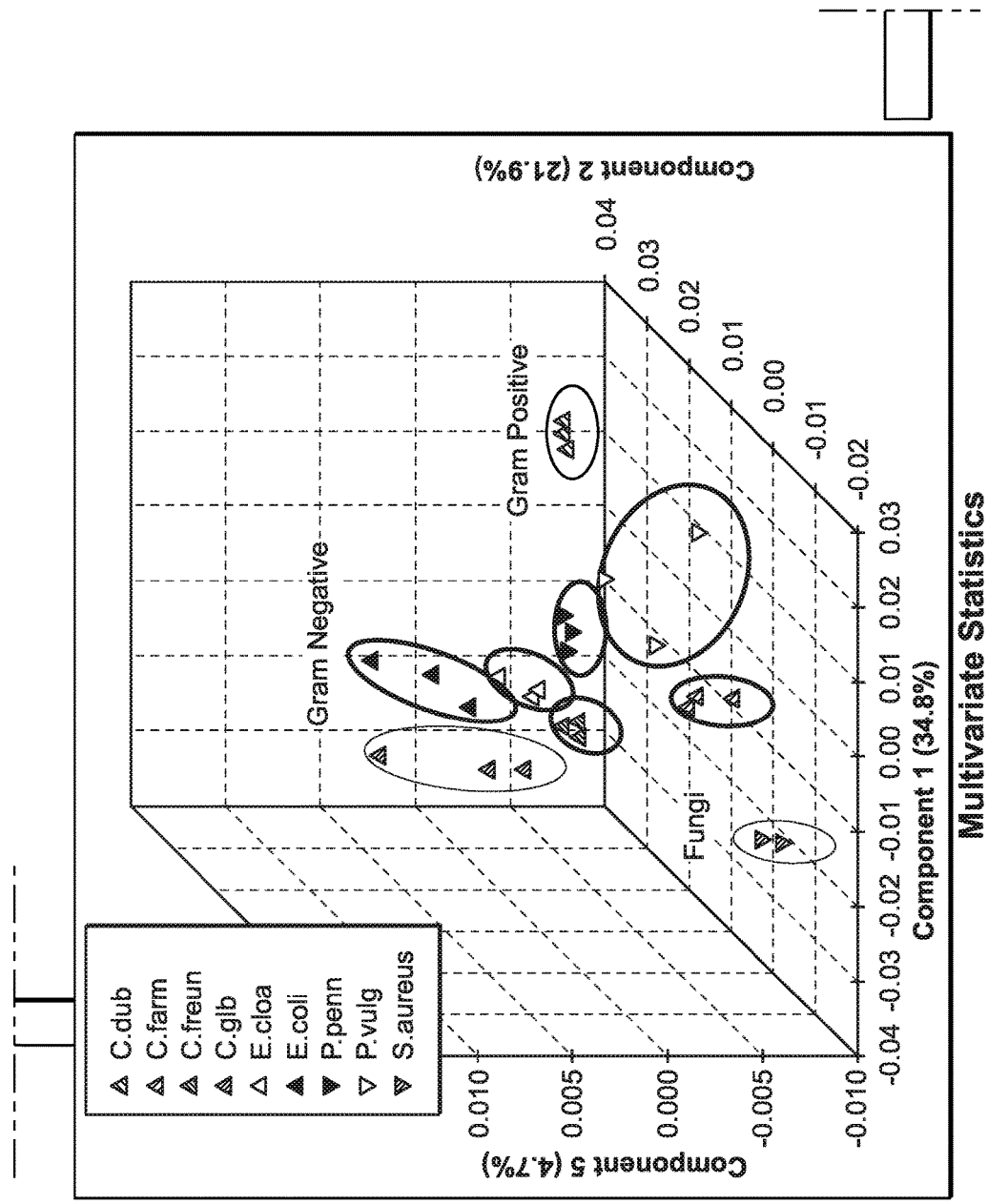
Figure 45C:
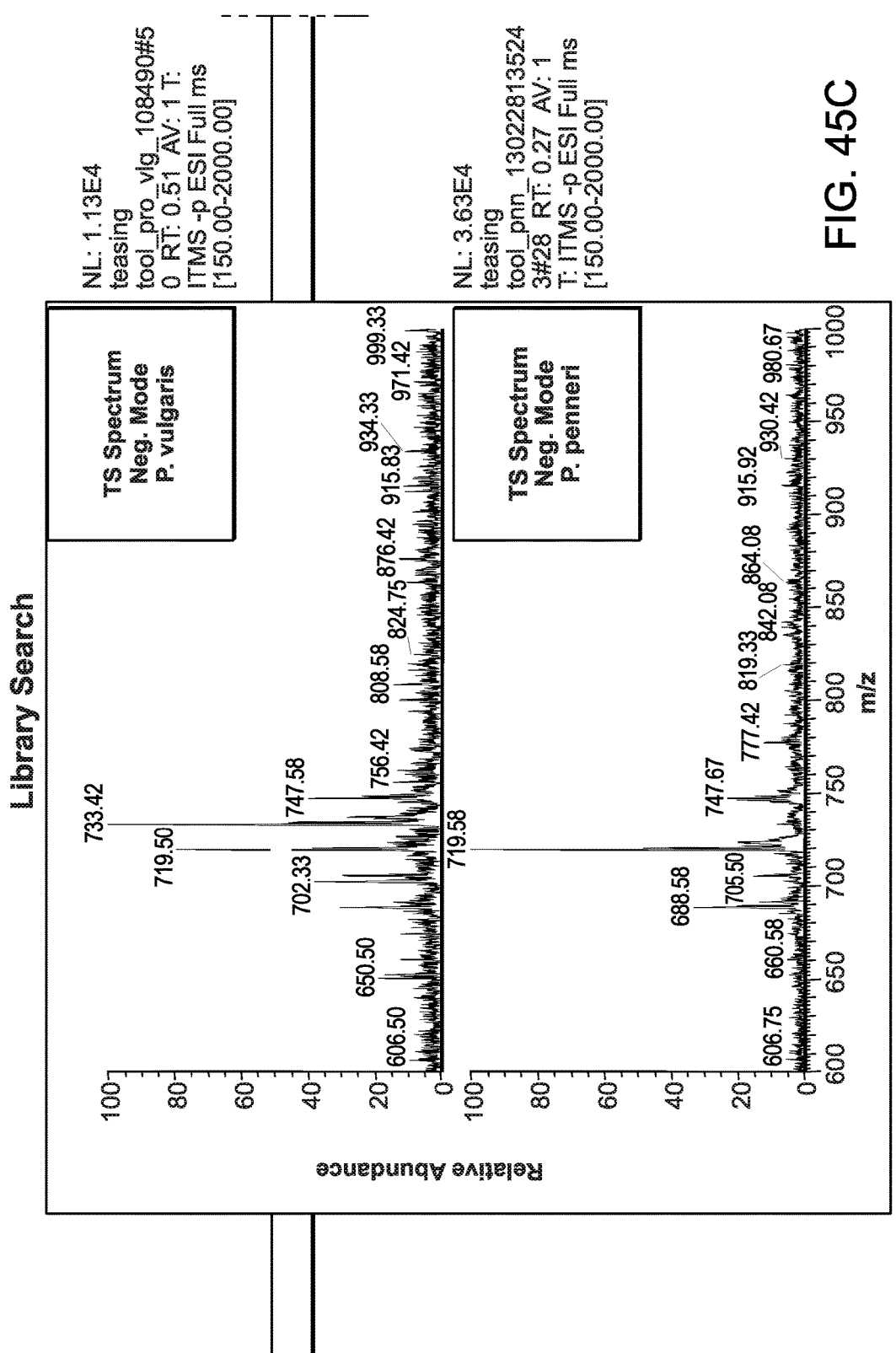
Figure 45D:
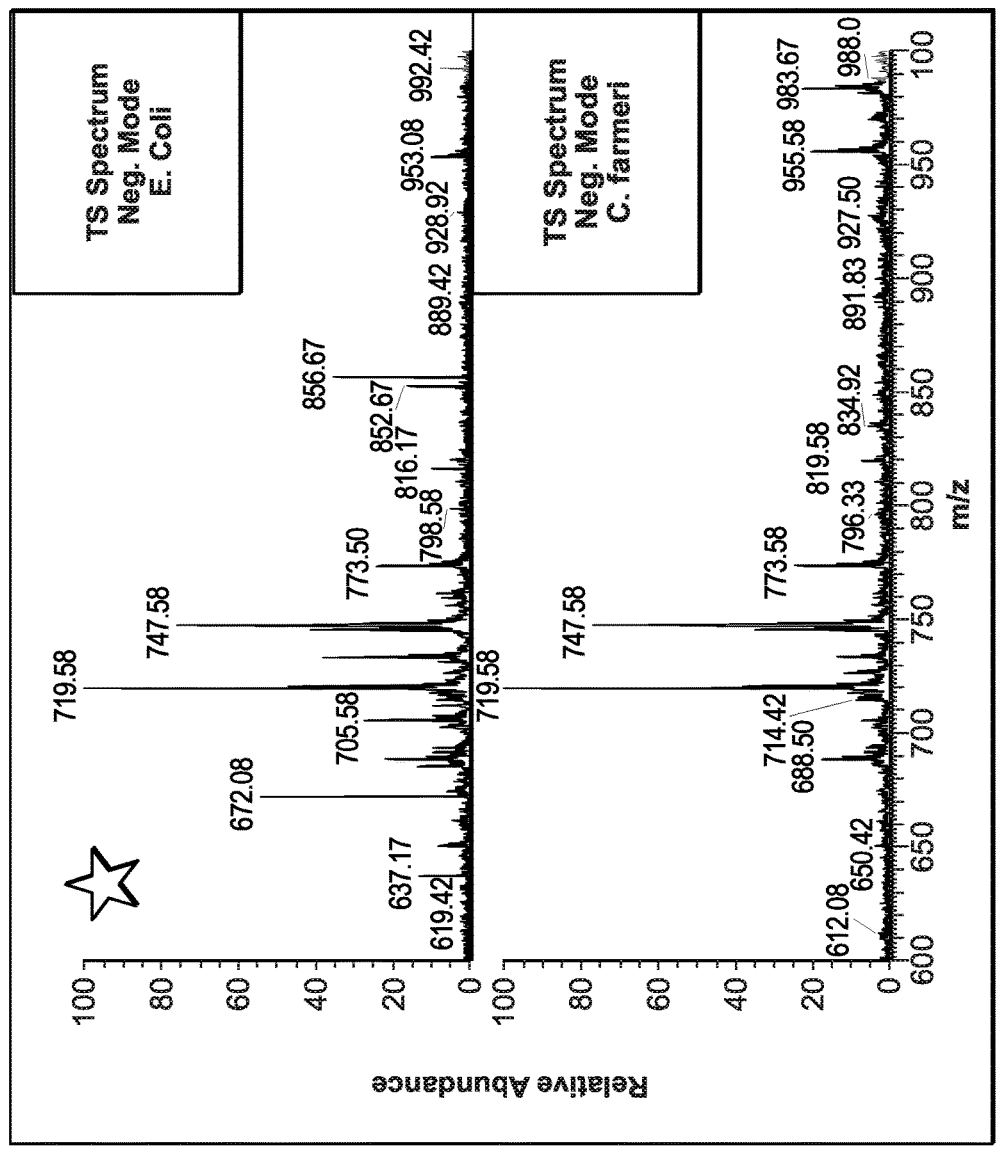
Figure 45E:
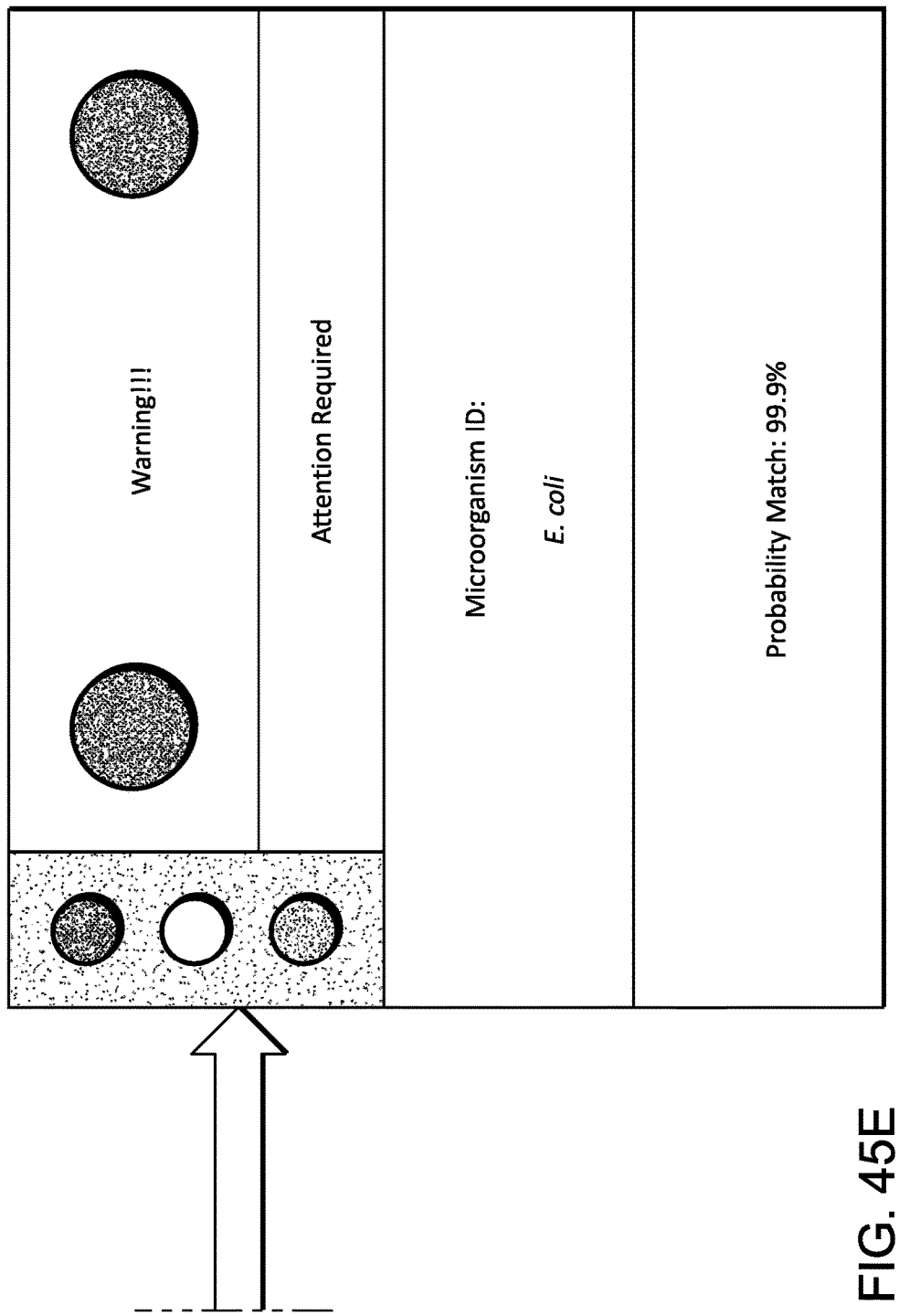
Figure 45F:
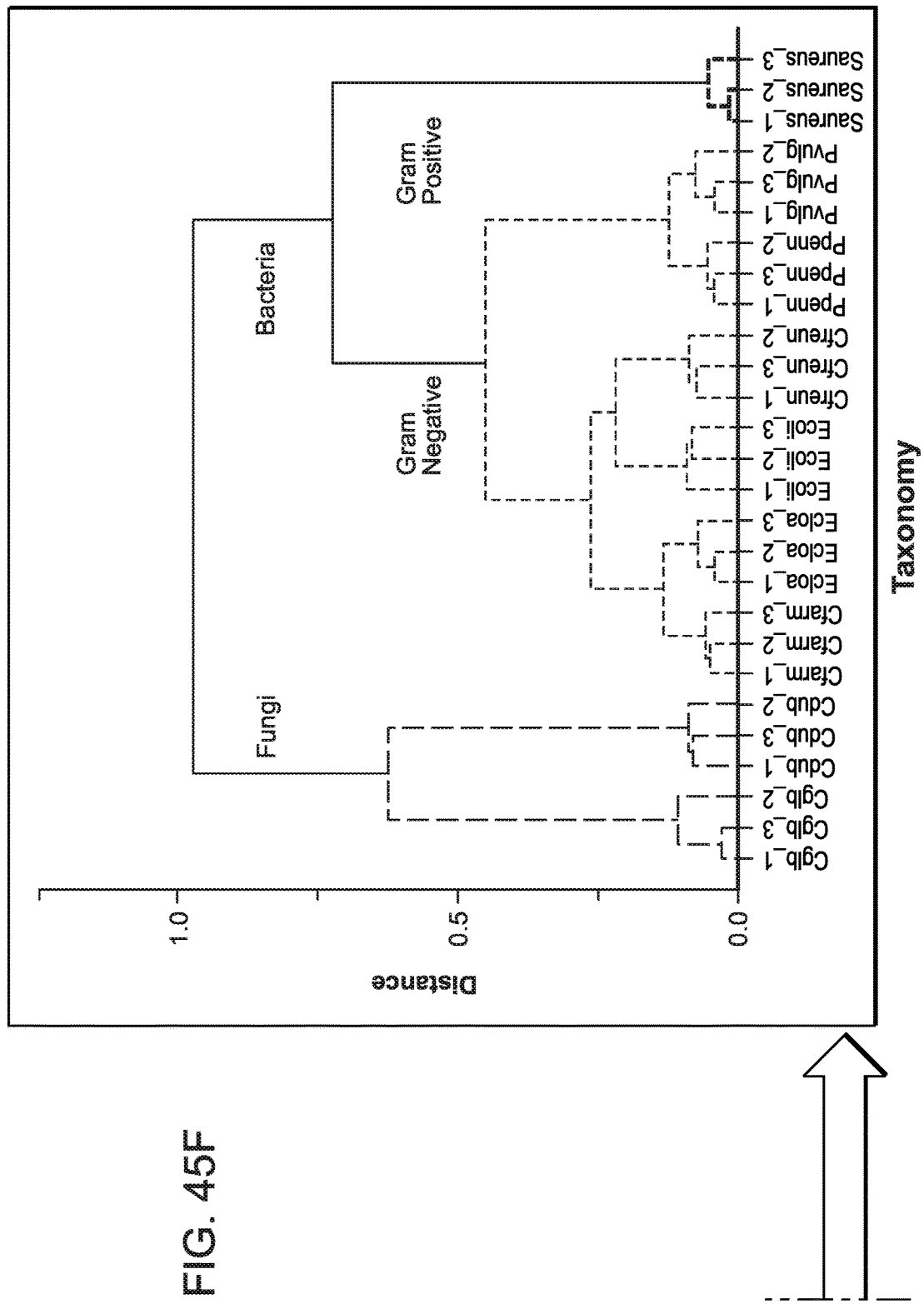

To generate similarity clusters, each mass spectrum is aligned against every other mass spectrum. From these alignments, a pair-wise alignment analysis is performed to determine "percent dissimilarity" between the members of the pair (FIG. 44). Briefly, this clustering method works by initially placing each entry in its own cluster, then iteratively joining the two nearest clusters, where the distance between two clusters is the smallest dissimilarity between a point in one cluster and a point in the other cluster.

Various organisms, e.g., viruses, and various microorganisms, e.g., bacteria, protists, and fungi, can be identified with the methods featured herein. The sample containing the organism to be identified can be a human sample, e.g., a tissue sample, e.g., epithelial (e.g., skin), connective (e.g., blood and bone), muscle, and nervous tissue, or a secretion sample, e.g., saliva, urine, tears, and feces sample. The sample can also be a non-human sample, e.g., a horse, camel, llama, cow, sheep, goat, pig, dog, cat, weasel, rodent, bird, reptile, and insect sample. The sample can also be from a plant, water source, food, air, soil, plants, or other environmental or industrial sources.

The methods described herein include correlating the mass spectrum from the unknown organism with a database that includes mass spectra of known organisms. The methods involve comparing each of the mass spectra from the unknown organism from a sample against each of the entries in the database, and then combining match probabilities across different spectra to create an overall match probability (FIGS. 45A-F).

What is claimed is:

1. A system for analyzing a contaminant from an industrial liquid or gas sample, the system comprising:
  a capture module, the module configured to capture a contaminant from an industrial liquid or gas sample in an ambient environment and generate ions of the contaminant, wherein the capture module comprises a porous substrate connected to a voltage source; and
  a mass analyzer operably coupled to the capture module to receive the generated ions of the contaminant.

2. The system according to claim 1, wherein the porous substrate is discrete from a flow of solvent.

3. The system according to claim 1, wherein the porous substrate tapers to a distal tip.

4. The system according to claim 1, wherein the capture module further comprises a gas-flow generating device that directs flow of the gas through the porous substrate.

5. The system according to claim 1, further comprising a solvent applied to the porous substrate.

6. The system according to claim 5, wherein the solvent comprises an internal standard.

7. The system according to claim 1, wherein the mass analyzer is for a mass spectrometer or a handheld mass spectrometer.

8. The system according to claim 7, wherein the mass analyzer is selected from the group consisting of: a quadrupole ion trap, a rectalinear ion trap, a cylindrical ion trap, a ion cyclotron resonance trap, an orbitrap, a time of flight, a Fourier Transform ion cyclotron resonance, and sectors.

9. The system according to claim 1, wherein the porous substrate is filter paper.

10. The system according to claim 9, wherein the filter paper tapers to a distal tip.

11. A method for analyzing a contaminant from an industrial liquid or gas sample, the system comprising:
  providing a capture module, the module configured to capture a contaminant from an industrial liquid or gas sample in an ambient environment and generate ions of the contaminant, wherein the capture module comprises a porous substrate connected to a voltage source;
  capturing the contaminant from the industrial liquid or gas sample to the porous substrate of the capture module;
  generating ions of the contaminant held by the porous substrate via the voltage source that is coupled to the porous substrate; and
  analyzing the generated ions of the contaminant in a mass analyzer that is operably coupled to the capture module.

12. The method according to claim 11, wherein the porous substrate is discrete from a flow of solvent.

13. The method according to claim 11, wherein the porous substrate tapers to a distal tip.

14. The method according to claim 11, wherein the capture module further comprises a gas-flow generating device that directs flow of the gas through the porous substrate.

15. The method according to claim 11, further comprising applying a solvent to the porous substrate.

16. The method according to claim 15, wherein the solvent comprises an internal standard.

17. The method according to claim 11, wherein the mass analyzer is for a mass spectrometer or a handheld mass spectrometer.

18. The method according to claim 17, wherein the mass analyzer is selected from the group consisting of: a quadrupole ion trap, a rectalinear ion trap, a cylindrical ion trap, a ion cyclotron resonance trap, an orbitrap, a time of flight, a Fourier Transform ion cyclotron resonance, and sectors.

19. The system according to claim 11, wherein the porous substrate is filter paper.

20. The system according to claim 19, wherein the filter paper tapers to a distal tip.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Homo sapiens

<400> SEQUENCE: 1

Asp Arg Val Tyr Ile His Pro Phe His Leu
1               5                   10